(12) United States Patent
Belhocine et al.

(10) Patent No.: US 10,927,370 B2
(45) Date of Patent: *Feb. 23, 2021

(54) SINGLE CELL ANALYSIS OF TRANSPOSASE ACCESSIBLE CHROMATIN

(71) Applicant: 10X GENOMICS, INC., Pleasanton, CA (US)

(72) Inventors: Zahra Kamila Belhocine, Fremont, CA (US); Geoffrey McDermott, Livermore, CA (US); Francesca Meschi, Menlo Park, CA (US); Xinying Zheng, San Jose, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/419,630

(22) Filed: May 22, 2019

(65) Prior Publication Data

US 2019/0376058 A1 Dec. 12, 2019

Related U.S. Application Data

(63) Continuation of application No. 16/206,168, filed on Nov. 30, 2018, which is a continuation of application No. 15/842,687, filed on Dec. 14, 2017, now Pat. No. 10,400,235, application No. 16/419,630, which is a continuation-in-part of application No. PCT/US2018/034774, filed on May 25, 2018.

(60) Provisional application No. 62/511,905, filed on May 26, 2017, provisional application No. 62/527,529, filed on Jun. 30, 2017, provisional application No. 62/650,223, filed on Mar. 29, 2018.

(51) Int. Cl.
*C12N 15/10* (2006.01)

(52) U.S. Cl.
CPC ..... *C12N 15/1065* (2013.01); *C12N 15/1068* (2013.01); *C12N 15/1075* (2013.01); *C12N 15/1096* (2013.01)

(58) Field of Classification Search
None
See application file for complete search history.

(56) References Cited

U.S. PATENT DOCUMENTS

| | | |
|---|---|---|
| 2,797,149 A | 6/1957 | Skeggs |
| 3,047,367 A | 7/1962 | Kessler |
| 3,479,141 A | 11/1969 | William et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,695,940 A | 12/1997 | Drmanac et al. |
| 5,700,642 A | 12/1997 | Monforte et al. |
| 5,705,628 A | 1/1998 | Hawkins et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |

(Continued)

FOREIGN PATENT DOCUMENTS

| | | |
|---|---|---|
| CN | 102292455 A | 12/2011 |
| CN | 103202812 A | 7/2013 |
| EP | 0249007 A2 | 12/1987 |
| EP | 0271281 A2 | 6/1988 |
| EP | 0637996 B1 | 7/1997 |

(Continued)

OTHER PUBLICATIONS

10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.

(Continued)

*Primary Examiner* — Christopher M Gross
(74) *Attorney, Agent, or Firm* — Benjamin C. Pelletier; Venable LLP

(57) ABSTRACT

Methods and systems for sample preparation techniques that allow amplification (e.g., whole genome amplification) and sequencing of chromatin accessible regions of single cells are provided. The methods and systems generally operate by forming or providing partitions (e.g., droplets) including a single biological particle and a single bead comprising a barcoded oligonucleotide. The preparation of barcoded next-generation sequencing libraries prepared from a single cell is facilitated by the transposon-mediated transposition and fragmentation of a target nucleic acid sequence. The methods and systems may be configured to allow the implementation of single-operation or multi-operation chemical and/or biochemical processing within the partitions.

30 Claims, 42 Drawing Sheets

Specification includes a Sequence Listing.

(56) References Cited

U.S. PATENT DOCUMENTS

| | | |
|---|---|---|
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 8,986,628 B2 | 3/2015 | Stone et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |

(56) References Cited

U.S. PATENT DOCUMENTS

| | | |
|---|---|---|
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,436,088 B2 | 9/2016 | Seul et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,017,759 B2 | 7/2018 | Kaper et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 | 3/2019 | Hindson et al. |
| 10,227,648 B2 | 3/2019 | Hindson et al. |
| 10,253,364 B2 | 4/2019 | Hindson et al. |
| 10,273,541 B2 | 4/2019 | Hindson et al. |
| 10,400,235 B2 * | 9/2019 | Belhocine ........ C12Q 2563/179 |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |

(56) References Cited

U.S. PATENT DOCUMENTS

| | | |
|---|---|---|
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2008/0268507 A1 | 10/2008 | Xu et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0062129 A1 | 3/2009 | McKernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov et al. |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0206554 A1 | 7/2014 | Hindson et al. |

(56) References Cited

U.S. PATENT DOCUMENTS

| | | |
|---|---|---|
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0031037 A1 | 1/2015 | Li et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0211056 A1 | 7/2015 | Um et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0247182 A1 | 9/2015 | Faham et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0201125 A1 | 7/2016 | Samuels et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244811 A1 | 8/2016 | Edwards |
| 2016/0244825 A1 | 8/2016 | Vigneault et al. |
| 2016/0251697 A1 | 9/2016 | Nolan et al. |
| 2016/0281160 A1 | 9/2016 | Jarosz et al. |
| 2016/0289769 A1 | 10/2016 | Schwartz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0211127 A1 | 7/2017 | Mikkelsen et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2018/0008984 A1 | 1/2018 | Bharadwaj et al. |
| 2018/0016634 A1 | 1/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0080021 A1* | 3/2018 | Reuter ............... C12N 15/1065 |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094313 A1 | 4/2018 | Hindson |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0216162 A1 | 8/2018 | Belhocine et al. |
| 2018/0237951 A1 | 8/2018 | Bock et al. |
| 2018/0258466 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0327839 A1 | 11/2018 | Hindson et al. |
| 2018/0335424 A1 | 11/2018 | Chen et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0363029 A1 | 12/2018 | Hindson et al. |
| 2018/0371538 A1 | 12/2018 | Blauwkamp et al. |
| 2018/0371540 A1 | 12/2018 | Hindson et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0127731 A1 | 5/2019 | McDermott |
| 2019/0136316 A1 | 5/2019 | Hindson et al. |
| 2019/0136317 A1 | 5/2019 | Hindson et al. |
| 2019/0136319 A1 | 5/2019 | Hindson et al. |

FOREIGN PATENT DOCUMENTS

| | | |
|---|---|---|
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |

(56) References Cited

FOREIGN PATENT DOCUMENTS

| | | |
|---|---|---|
| EP | 2635679 A1 | 9/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| WO | WO-8402000 A1 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006071770 A2 | 7/2006 |
| WO | WO-2006078841 A1 | 7/2006 |
| WO | WO-2006086210 A2 | 8/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | 2008/135512 A2 | 11/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | 2009147386 A1 | 12/2009 |
| WO | WO-2009147386 A1 | 12/2009 |
| WO | WO-2010004018 A2 | 1/2010 |
| WO | WO-2010009735 A1 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011106314 A2 | 9/2011 |
| WO | WO-2011140627 A1 | 11/2011 |
| WO | WO-2011156529 A2 | 12/2011 |
| WO | WO-2012012037 A1 | 1/2012 |
| WO | WO-2011140510 A3 | 3/2012 |
| WO | WO-2012047889 A2 | 4/2012 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012087736 A1 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012150317 A1 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014018460 A1 | 1/2014 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |

(56) References Cited

FOREIGN PATENT DOCUMENTS

| | | |
|---|---|---|
| WO | WO-2014150931 A1 | 9/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015031691 A1 | 3/2015 |
| WO | WO-2015044428 A1 | 4/2015 |
| WO | WO-2015164212 A1 | 10/2015 |
| WO | WO-2015185067 A1 | 12/2015 |
| WO | WO-2015188839 A2 | 12/2015 |
| WO | WO-2015200893 A2 | 12/2015 |
| WO | WO-2016040476 A1 | 3/2016 |
| WO | WO-2016033251 A3 | 4/2016 |
| WO | WO-2016061517 A2 | 4/2016 |
| WO | WO-2016100976 A2 | 6/2016 |
| WO | WO-2016126871 A2 | 8/2016 |
| WO | WO-2016138496 A1 | 9/2016 |
| WO | WO-2016149661 A1 | 9/2016 |
| WO | WO-2016168584 A1 | 10/2016 |
| WO | WO-2016187256 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017079593 A1 | 5/2017 |
| WO | WO-2017096158 A1 | 6/2017 |
| WO | WO-2017117358 A1 | 7/2017 |
| WO | WO-2017156336 A1 | 9/2017 |
| WO | WO-2018031631 A1 | 2/2018 |
| WO | WO-2018039969 A1 | 3/2018 |
| WO | WO-2018045186 A1 | 3/2018 |
| WO | WO-2018058073 A2 | 3/2018 |
| WO | WO-2018103025 A1 | 6/2018 |
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018172726 A1 | 9/2018 |
| WO | WO-2018174827 A1 | 9/2018 |
| WO | WO-2018191701 A1 | 10/2018 |
| WO | WO-2019028166 A1 | 2/2019 |
| WO | 2019/099751 A1 | 5/2019 |
| WO | WO-2019084328 A1 | 5/2019 |

OTHER PUBLICATIONS

Abate, et al. Beating Poisson encapsulation statistics using close-packed ordering. Lab Chip. Sep. 21, 2009;9(18):2628-31. doi: 10.1039/b909386a. Epub Jul. 28, 2009.

Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.

Abate et al., Valve-based flow focusing for drop formation. Appl Phys Lett. 2009;94. 3 pages.

Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.

Adamson et al., "Production of arrays of chemically distinct nanolitre plugs via repeated splitting in microfluidic devices", Lab Chip 6(9): 1178-1186 (Sep. 2006).

Adey, et al. Rapid, low-input, low-bias construction of shotgun fragment libraries by high-density in vitro transposition. Genome Biology 11:R119 (2010).

Adey, et al., "Ultra-low-input, tagmentation-based whole-genome bisulfite sequencing", Genome Research, 2012, 22 ;6): 1139-1143.

Agasti, et al. Photocleavable DNA barcode-antibody conjugates allow sensitive and multiplexed protein analysis in single cells. J Amer Chem Soc ePub, Nov. 2, 2012, vol. 134, No. 45, pp. 18499-18502.

Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.

AH006633.3 (*Homo sapiens* clone P1 and PAC max interactor 1 (MXI1) gene, complete cds, NCBI Reference Sequence, priority to Jun. 10, 2016, 5 pages) (Year:2016).

Ahern, "Biochemical, Reagents Kits Offer Scientists Good Return on Investment" The Scientist (1995) 9(15):1-7.

Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).

Aitman, et al. Copy number polymorphism in Fcgr3 predisposes to glomerulonephritis in rats and humans. Nature. Feb. 16, 2006;439(7078):851-5.

Akselband, "Enrichment of slow-growing marine microorganisms from mixed cultures using gel microdrop (GMD) growth assay and fluorescence-activated cell sorting", J. Exp. Marine Bioi., 329: 196-205 (2006).

Akselband, "Rapid mycobacteria drug susceptibility testing using gel microdrop (GMD) growth assay and flow cytometry", J. Microbiol. Methods, 62:181-197 (2005).

Altemos et al., "Genomic Characterization of Large Heterochromatic Gaps in the Human Genome Assembly," PLOS Computational Biology, May 15, 2014, vol. 10, Issue 5, 14 pages.

Amini, S. et al. "Haplotype-resolved whole-genome sequencing by contiguity-preserving transposition and combinatorial indexing" Nature Genetics (2014) 46:1343-1349 doi:10.1038/ng.3119.

Anna, S.L., et al., "Formation of dispersions using "flow focusing" in microchannels," Applied Physics Letters, vol. 82, No. 3, pp. 364-366 (2003).

Anonymous, "Oligo(dT)25 cellulose beads" NEB (2012) Retrieved from the Internet:https://www.neb.com/~/media/Catalog/All-Products/286CA51268E24DE1B06F1CB2886981354/Datacards%20or%Manuals/S1408Datasheet-Lot0011205.pdf.

Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.

Anonymous: "TCEP=HCI" Thermo Scientific, Dec. 31, 2013 (Dec. 31, 2018), XP055508461, Retrieved from the Internet: URL:https://assets.thermofisher.com/TFS-Assets/LSG/manuals/MAN0011306_TCEP_HCl_UG.pdf.

Anonymous: "Three Ways to Get Intimate with Epigenetic Marks". Oct. 24, 2012. Retrieved from Internet: https://epigenie.com/three-ways-to-get-intimate-with-epigenetic-marks/.

Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.

Ason et al. DNA sequence bias during Tn5 transposition. Journal of molecular biology 335.5 (2004): 1213-1225.

Attia, et al. Micro-injection moulding of polymer microfluidic devices. Microfluidics and nanofluidics. 2009; 7(1):1-28.

Balikova, et al. Autosomal-dominant microtia linked to five tandem copies of a copy-number-variable region at chromosome 4p16. Am J Hum Genet. Jan. 2008;82(1):181-7. doi: 10.1016/j.ajhg.2007.08.001.

Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.

Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.

(56) References Cited

OTHER PUBLICATIONS

BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentley, et al. 2008. Supplementary Information. pp. 1-55 Nature. Nov. 6, 2008; 456(7218):53-9.
Bentolila, et al. Single-step multicolor fluorescence in situ hybridization using semiconductor quantum dot-DNA conjugates. Cell Biochem Biophys. 2006;45(1):59-70.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al, "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. Pcr Methods Appl. Aug. 1993; 3(1):28-31.
Buenrostro, et al. ATAC-seq: A Method for Assaying Chromatin Accessibility Genome-Wide. Curr Protoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.

Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Bystrykh, et al. Generalized DNA barcode design based on Hamming codes. PLoS One. 2012;7(5):e36852. doi: 10.1371/journal.pone.0036852. Epub May 17, 2012.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Casbon, et al, "Reflex: intramolecular barcoding of long-range PCR products for sequencing multiple pooled DNAs", Nucleic Acids Res., pp. 1-6, 2013.
Cejas, P. et al. "Chromatin immunoprecipitation from fixed clinical tissues reveals tumor-specific enhancer profiles" Nature Med (2016) 22(6):685-691.
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.

(56) References Cited

OTHER PUBLICATIONS

Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/170,980, filed Oct. 25, 2018.
Co-pending U.S. Appl. No. 16/206,168, filed Nov. 30, 2018.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/294,769, filed Mar. 6, 2019.
Co-pending U.S. Appl. No. 16/395,090, filed Apr. 25, 2019.
Co-pending U.S. Appl. No. 16/419,428, filed May 22, 2019.
Co-pending U.S. Appl. No. 16/419,461, filed May 22, 2019.
Co-pending U.S. Appl. No. 16/419,555, filed May 22, 2019.
Co-pending U.S. Appl. No. 16/419,820, filed May 22, 2019.
Coufal, et al. L1 retrotransposition in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9.".
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Definition of "corresponding", Merriam-Webster Online, downloaded from http://www.merriam-webster.com/dictionary/corresponding (Year: 2019).
Dekker, et al. Capturing chromosome conformation. Science. Feb. 15, 2002;295(5558):1306-11.
Delehanty, et al. Peptides for specific intracellular delivery and targeting of nanoparticles: implications for developing nanoparticle-mediated drug delivery. Ther Deliv. Sep. 2010;1(3):411-33.
Demirci, et al. Single cell epitaxy by acoustic picolitre droplets. Lab Chip. Sep. 2007;7(9):1139-45. Epub Jul. 10, 2007.
Depristo et al. A framework for variation discovery and genotyping using next-generation DNA sequencing data. Nature Genet 43:491-498 (2011).
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Epicenter, EZ-Tn5 Transposase, Epicenter, 2012, 1-5. (Year: 2012).
Epicentre., "Ez-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fanielli, M. et al. "Pathology tissue-chromatin immunoprecipitation, coupled with high-throughput sequencing, allows the epigenetic profiling of patient samples" PNAS (2010) 107(50):21535-21540.
Fisher, et al. A scalable, fully automated process for construction of sequence-ready human exome targeted capture libraries. Genome Biol. 2011;12(1):R1. doi: 10.1186/gb-2011-12-1-r1. Epub Jan. 4, 2011.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
GHADESSy, et al. Directed evolution of polymerase function by compartmentalized self-replication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.

(56) References Cited

OTHER PUBLICATIONS

Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hebenstreit. Methods, Challenges and Potentials of Single Cell RNA-seq. Biology (Basel). Nov. 16, 2012;1(3):658-67. doi: 10.3390/biology1030658.
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
Hosono S, et al. Unbiased whole-genome amplification directly from clinical samples. Genome Res. May 2003; 13(5):954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to The University of Birmingham for the degree of Doctor of Philosophy. 2009.
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Jin, et al. Genome-wide detection of DNase I hypersensitive sites in single cells and FFPE tissue samples. Nature. Dec. 3, 2015;528(7580):142-6. doi: 10.1038/nature15740.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Jung, et al. Micro machining of injection mold inserts for fluidic channel of polymeric biochips. Sensors. 2007; 7(8):1643-1654.
Kamperman, et al. Centering Single Cells in Microgels via Delayed Crosslinking Supports Long-Term 3D Culture by Preventing Cell Escape. Small. Jun. 2017;13(22). doi: 10.1002/sml1.201603711. Epub Apr. 28, 2017.
Kaper, et al. Supporting Information for "Whole-genome haplotyping by dilution, amplification, and sequencing." Proc Natl Acad Sci USA. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug 3, 2015.
Katsura, et al. Indirect micromanipulation of single molecules in water-in-oil emulsion. Electrophoresis. Jan. 2001;22(2):289-93.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011;9(1):72-4.

(56) References Cited

OTHER PUBLICATIONS

Klein, et al. Droplet barcoding for single-cell transcriptomics applied to embryonic stem cells. Cell. May 21, 2015;161(5):1187-201. doi: 10.1016/j.cell.2015.04.044.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Kolodeziejczyk et al., "The technology and biology of single-cell RNA sequencing", Molecular Cell, vol. 58 (May 21, 2015).
Korlach et al., Methods in Enzymology, Real-Time DNA Sequencing from Single Polymerase Molecules, (2010) 472:431-455.
Koster et al., "Drop-based microfluidic devices for encapsulation of single cells", Lab on a Chip The Royal Soc. of Chem. 8: 1110-1115 (2008).
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.
Kutyavin, et al. Oligonucleotides containing 2-aminoadenine and 2-thiothymine act as selectively binding complementary agents. Biochemistry. Aug. 27, 1996;35(34):11170-6.
Kwok, et al, "Single-molecule analysis for molecular haplotyping", Hum Mutat., 23:442-6, 2004.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271(30):17692-17696 (Year: 1996).
Lebedev, a. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Highly multiplexed subcellular RNA sequencing in situ. Science. Mar. 21, 2014;343(6177):1360-3. doi: 10.1126/science. 1250212. Epub Feb. 27, 2014.".
Lee, J-H. et al. "Fluorescent in situ sequencing (FISSEQ) of RNA for gene expression profiling in intact cells and tissues" Nature Protocols (Feb. 12, 2015) 10(3):442-458.
"Lennon et al. A scalable, fully automated process for construction of sequence-ready barcoded libraries for 454. Genome Biology 11:R15 (2010).".
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
"List of sequenced bacterial genomes" (Wikipedia.com; accessed Jan. 24, 2014).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macaulay; et al., "G&T-seq: parallel sequencing of single-cell genomes and transcriptomes. Nature Methods, 2015, p. 1-7.".
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Mali, et al. Barcoding cells using cell-surface programmable DNA-binding domains. Nat Methods. May 2013;10(5):403-6. doi: 10.1038/nmeth.2407. Epub Mar. 17, 2013.
Man. Monolithic Structures for Integrated Microfluidic Analysis. PhD Thesis. 2001.
Marcus. Gene method offers diagnostic hope. The Wall Street Journal. Jul. 11, 2012.
Margulies 2005 Supplementary methods (Year: 2005).
Margulies et al. "Genome sequencing in microfabricated high-density picoliter reactors", Nature (2005) 437:376-380.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.

(56) References Cited

OTHER PUBLICATIONS

McGinnis, et al. MULTI-seq: Scalable sample multiplexing for single-cell RNA sequencing using lipid-tagged indices. bioRxiv 387241; doi: https://doi.org/10.1101/387241.
Merriman, et al. Progress in ion torrent semiconductor chip based sequencing. Electrophoresis. Dec. 2012;33(23):3397-417. doi: 10.1002/elps.201200424.
"Meyer, et al., From micrograms to picograms: quantitative PCR reduces the material demands of high-throughput sequencing, Nucleic Acids Research, 2008, vol. 36, No. 1, 6 pp.".
Meyer, et al. Targeted high-throughput sequencing of tagged nucleic acid samples. Nucleic Acids Res. 2007;35(15):e97.
Microfluidic ChipShop. Microfluidic product catalogue. Mar. 2005.
Microfluidic ChipShop. Microfluidic product catalogue. Oct 2009.
Mignardi, M. et al. "Oligonucleotide gap-fill ligation for mutation detection and sequencing in situ" Nucl Acids Res (2015) 43(22):e151.
Miller JC, et al. An improved zinc-finger nuclease architecture for highly specific genome editing. Nat. Biotechnol. 2007;25:778-785.
Miller-Stephenson Chemicals 157 Fs Series catalog, www.miller-stephenon.com.
MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Narayanan, J. et al. "Determination of agarose gel pore size: Absorbance measurements vis a vis other techniques" Journal of Physics: Conference Series 28 (2006) 83-86 (Year: 2006).
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.

Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production of Monodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics. ,13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Pfeifer, et al. Bivalent cholesterol-based coupling of oligonucleotides to lipid membrane assemblies. J Am Chem Soc. Aug. 25, 2004;126(33):10224-5.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy No. variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr. 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).

(56) References Cited

OTHER PUBLICATIONS

Reis, A. et al. "CRISPR/Cas9 and Targeted Genome Editing: A New Era in Molecular Biology" (2014) XP002766825: URL:https://ww.neb.com/tools-and-resources/feabture-articles/crispr- cas9-and-targeted-genome-editing-a-new-era-in-molecular-biology.

Reisner, et al, "Single-molecule denaturation mapping of DNA in nanofluidic channels", Proc Natl Acad Sci U.S.A., 107: 13294-9, 2010.

Repp et al. "Genotyping by Multiplex Polymerase Chain Reaction for Detection of Endemic Hepatitis B Virus Transmission" J Clinical Microbiology (1993) 31:1095-1102.

Richardson, et al. Novel inhibition of archaeal family-D DNA polymerase by uracil. Nucleic acids research 41.7 (2013): 4207-4218.

Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.

Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005 UsingMultiplexIdentifierAdaptorsForTheGSFLXTitaniumChemistry-ExtendedMIDSet.pdf.

Rodrigue, S. et al. "Whole genome amplification and de novo assembly of single bacterial cells" PLoS One. Sep. 2, 2009;4(9):e6864. doi: 10.1371/journal.pone.0006864.

Rogozin, et al. A highly conserved family of inactivated archaeal B family DNA polymerases. Biol Direct. Aug. 6, 2008;3:32. doi: 10.1186/1745-6150-3-32.

Ropers. New perspectives for the elucidation of genetic disorders. Am J Hum Genet. Aug. 2007;81(2):199-207. Epub Jun. 29, 2007.

Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.

Rotem, et al. Single Cell Chip-Seq Using Drop-Based Microfluidics. Abstract #50. Frontiers of Single Cell Analysis, Stanford University Sep. 5-7, 2013.

Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.

Ryan, "Rapid assay for mycobacterial growth and antibiotic susceptibility using gel microdrop and encapsulation", J. Clinical Microbial., 33:7 1720-1726 (1995).

Sakaguchi, et al. (1996) Cautionary Note on the Use of dUMP-Containing PCR Primers with Pfu and VentR. Biotechniques, 21(3): 369-370 (Year: 1996).

Sander JD, et al. Selection-free zinc-finger-nuclease engineering by context-dependent assembly (CoDA). Nat. Methods. 2011;8:67-69.

Savva, et al. The structural basis of specific base-excision repair by uracil-DNA glycosylase. Nature. Feb. 9, 1995;373(6514):487-93.

Schirinzi et al., Combinatorial sequencing-by-hybridization: Analysis of the NF1 gene. Genet Test. 2006 Spring;10(1):8-17.

Schmeider, et al. Fast identification and removal of sequence contamination from genomic and metagenomic datasets. PLoS One. Mar. 9, 2011;6(3):e17288. doi: 10.1371/journal.pone.0017288.

Schmitt, "Bead-based multiplex genotyping of human papillomaviruses", J. Clinical Microbial., 44:2 504-512 (2006).

Schubert, et al. Microemulsifying fluorinated oils with mixtures of fluorinated and hydrogenated surfactants. Colloids and Surfaces A; Physicochemical and Engineering Aspects, 84(1994) 97-106.

Schwartz, et al., "Capturing native long-range contiguity by in situ library construction and optical sequencing", PNAS (Nov. 2012), 109(46)18749-18754.

Sebat, et al. Strong association of de novo copy number mutations with autism. Science. Apr. 20, 2007;316(5823):445-9. Epub Mar. 15, 2007.

Seiffert, et al. Smart microgel capsules from macromolecular precursors. J Am Chem Soc. May 12, 2010;132(18):6606-9. doi: 10.1021/ja102156h.

Shah, "Fabrication of mono disperse thermosensitive microgels and gel capsules in micro fluidic devices", Soft Matter, 4:2303-2309 (2008).

Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.

Shaikh, et al. A modular microfluidic architecture for integrated biochemical analysis. Proc Natl Acad Sci U S A. Jul. 12, 2005;102(28):9745-50. Epub Jun. 28, 2005.

Shimkus, et al. A chemically cleavable biotinylated nucleotide: usefulness in the recovery of protein-DNA complexes from avidin affinity columns. Proc Natl Acad Sci U S A. May 1985;82(9):2593-7.

Shlien, et al. Copy number variations and cancer. Genome Med. Jun. 16, 2009;1(6):62. doi: 10.1186/gm62.

Shlien, et al. Excessive genomic DNA copy number variation in the Li-Fraumeni cancer predisposition syndrome. Proc Natl Acad Sci USA. Aug. 12, 2008;105(32):11264-9. doi: 10.1073/pnas.0802970105. Epub Aug. 6, 2008.

Shuttleworth, et al. Recognition of the pro-mutagenic base uracil by family B DNA polymerases from archaea. J Mol Biol. Mar. 26, 2004;337(3):621-34.

Sigma. Streptavidin-agarose (S1638) product information sheet. www.sigma-aldrich.com.

Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.

Simon, et al., "Using formaldehyde-assisted isolation of regulatory elements (FAIRE) to isolate active regulatory DNA", Nature Protocols, 2012, 7(2): 256-267.

Skerra. Phosphorothioate primers improve the amplification of DNA sequences by DNA polymerases with proofreading activity. Nucleic Acids Res. Jul. 25, 1992; 20(14):3551-4.

Smith, et al. Highly-multiplexed barcode sequencing: an efficient method for parallel analysis of pooled samples. Nucleic Acids Research, 38(13): e142 (2010).

Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.

Song, et al. Reactions in droplets in microfluidic channels. Angew Chem Int Ed Engl. Nov. 13, 2006;45(44):7336-56.

Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.

Holmberg, et al. The biotin-streptavidin interaction can be reversibly broken using water at elevated temperatures. Feb. 2, 2005. Electrophoresis, 26:501-510.

Invitrogen Dynal. Dynabeads M-280 Streptavidin 2006 product sheet.

Morton. Parameters of the human genome. Apr. 23, 1991. Proceedings of the National Academy of Sciences of the United States of America, 88: 7474-7476.

National Human Genome Research Institute (NHGRI). The Human Genome Project Completion: Frequently Asked Questions. Last Updated: Oct. 30, 2010.

Qiagen. Omniscript Reverse Transcription Handbook. Oct. 2010.

Seiffert, et al. Microfluidic fabrication of smart microgels from macromolecular precursors. 2010. Polymer.

Mamedov, I.Z., et al. (2013), Preparing unbiased T-cell receptor and antibody cDNA libraries for the deep next generation sequencing profiling, Front Immunol 4: 456.

Spormann Laboratory, Polymerase Chain Reaction (PCR), Alfred Spormann Laboratory, 2009, 1-3. (Year: 2009).

Stoeckius, et al. Large-scale simultaneous measurement of epitopes and transcriptomes in single cells. bioRxiv 113068; doi: https://doi.org/10.1101/113068.

(56) References Cited

OTHER PUBLICATIONS

Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998)

Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
ThermoFisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced Clarity for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)"107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ullal et al. Cancer Cell Profiling by Barcoding Allows Multiplexed Protein Analysis in Fine-Needle Aspirates. Sci Transl Med. Jan. 15, 2014; 6(219): 219ra9.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al, "Determination of haplotypes from single DNA molecules: a method for single-molecule barcoding", Hum Mutat., 28:913-21, 2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zhang F, et al. Efficient construction of sequence-specific TAL effectors for modulating mammalian transcription. Nat. Biotechnol. 2011;29:149-153.

(56) References Cited

OTHER PUBLICATIONS

Zhang. Genomics of inherited bone marrow failure and myelodysplasia. Dissertation [online]. University of Washington. 2015 [Retrieved on May 3, 2017].

Zhao, J., et al., "Preparation of hemoglobin-loaded Nano-sized particles with porous structure as oxygen carriers," Biomaterials, vol. 28, pp. 1414-1422 (2007).

Zheng, et al. Massively parallel digital transcriptional profiling of single cells. Nat Commun. Jan. 16, 2017;8:14049. doi: 10.1038/ncomms14049.

Zheng, X.Y. et al. "Haplotyping germline and cancer genomes with high-throughput linked-read sequencing" Nature Biotech (Feb. 1, 2016) 34(3):303-311.

Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).

Zhu et al. Hydrogel Droplet Microfluidics for High-Throughput Single Molecule/Cell Analysis. Accounts of Chemical Research Article ASAP. DOI: 10.1021/acs.accounts.6b00370.

Zhu, et al. Reverse transcriptase template switching: a SMART approach for full-length cDNA library construction. Biotechniques. Apr. 2001;30(4):892-7.

Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.

Zimmermann et at., Microscale production of hybridomas by hypo-osmolar electrofusion. Hum• Antibodies Hybridomas. Jan. 1992;3(1): 14-8.

Zong et al. Genome-Wide Detection of Single Nucleotide and Copy Number Variations of a Single Human Cell. Science 338(6114):1622-1626 (2012).

Sao et al., "Joint profiling of chromatin accessibility and gene expression in thousands of single cells," (2018) Science 361(6409):1380-1385.

Craig, "Unity in Transposition Reactions," (1995) Science 270(5234):253-254.

Kilgore et al., "Single-molecule and population probing of chromatin structure using DNA methyltransferases," (2007) Methods 41(3):320-332.

\* cited by examiner

Transposase Nucleic Acid Complex

Gel Bead

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agatgtgtat aagagaca                                                        18

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tctacactct ttccctacac gacgctcttc cgatct                                    36

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcggcag cgtcagatgt gtataagaga cag                                       33

<210> SEQ ID NO 4
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 4
actacacgac gctcttccga tct                                            23

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgactggag ttcagacgtg tgctcttccg atct                                34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtctcgtggg ctcggagatg tgtataagag acag                                34

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
taatacgact cactatag                                                  18

<210> SEQ ID NO 8
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(48)
<223> OTHER INFORMATION: a, c, t, g, unknown or other

<400> SEQUENCE: 8
tctacactct ttccctacac gacgctcttc cgatctnnnn nnnnnnnnag atgtgtataa    60
gagacag                                                              67

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t, g, unknown or other
```

<400> SEQUENCE: 9
ctgtctctta tacacatctn nnnnnnnnnn nagatcggaa gagcacacgt ctgaactcca    60
gtcac                                                                65

<210> SEQ ID NO 10
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(68)
<223> OTHER INFORMATION: a, c, t, g, unknown or other

<400> SEQUENCE: 10
aatgatacgg cgaccaccga tctacactct ttccctacac gacgctcttc cgatctnnnn    60
nnnnnnnnag atgtgtataa gagacag                                        87

<210> SEQ ID NO 11
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t, g, unknown or other
<220> FEATURE:
<221> NAME/KEY: modified_base
<222> LOCATION: (66)..(73)
<223> OTHER INFORMATION: a, c, t, g, unknown or other

<400> SEQUENCE: 11
ctgtctctta tacacatctn nnnnnnnnnn nagatcggaa gagcacacgt ctgaactcca    60
gtcacnnnnn nnnatctcgt atgccgtctt ctgcttg                             97

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(48)
<223> OTHER INFORMATION: a, c, t, g, unknown or other

<400> SEQUENCE: 12
tctacactct ttccctacac gacgctcttc cgatctnnnn nnnnnnnn                 48

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other

```
<400> SEQUENCE: 13
nnnnnnnnnn nnagatcgga agagcacacg tctgaactcc agtcac                    46

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agatgtgtat aagagacag                                                  19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctgtctctta tacacatct                                                  19

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (57)..(68)
<223> OTHER INFORMATION: a, c, t, g, unknown or other

<400> SEQUENCE: 16
aatgatacgg cgaccaccga tctacactct ttccctacac gacgctcttc cgatctnnnn     60 nnnnnnnn                                                              68

<210> SEQ ID NO 17
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other
<220> FEATURE:
<221> NAME/KEY: modified_base
<222> LOCATION: (47)..(54)
<223> OTHER INFORMATION: a, c, t, g, unknown or other

<400> SEQUENCE: 17
nnnnnnnnnn nnagatcgga agagcacacg tctgaactcc agtcacnnnn nnnnatctcg     60
tatgccgtct tctgcttg                                                   78

<210> SEQ ID NO 18
<211> LENGTH: 97
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(31)
<223> OTHER INFORMATION: a, c, t, g, unknown or other
<220> FEATURE:
<221> NAME/KEY: modified_base
<222> LOCATION: (66)..(73)
<223> OTHER INFORMATION: a, c, t, g, unknown or other

<400> SEQUENCE: 18
ctgtctctta tacacatctn nnnnnnnnnn nagatcggaa gagcacacgt ctgaactcca     60
gtcacnnnnn nnnatctcgt atgccgtctt ctgcttg                             97

<210> SEQ ID NO 19
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (53)..(68)
<223> OTHER INFORMATION: a, c, t, g, unknown or other

<400> SEQUENCE: 19
cgatgacgtt aatacgactc actatargga ctacacgacg ctcttccgat ctnnnnnnnn    60
nnnnnnnnag atgtgtataa gagacag                                       87

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(34)
<223> OTHER INFORMATION: a, c, t, g, unknown or other

<400> SEQUENCE: 20
ctacacgacg ctcttccgat ctnnnnnnnn nnnnagatgt gtataagaga cag           53
```

SINGLE CELL ANALYSIS OF TRANSPOSASE ACCESSIBLE CHROMATIN

CROSS-REFERENCE

This application is a continuation application of U.S. patent application Ser. No. 16/206,168, filed Nov. 30, 2018, which is a continuation application of U.S. patent application Ser. No. 15/842,687, filed Dec. 14, 2017, which claims priority to U.S. Provisional Patent Application No. 62/511,905, filed May 26, 2017, and to U.S. Provisional Patent Application No. 62/527,529, filed Jun. 30, 2017, each of which applications is entirely incorporated herein by reference.

SEQUENCE LISTING

The instant application contains a Sequence Listing which has been submitted electronically in ASCII format and is hereby incorporated by reference in its entirety. Said ASCII copy, created on Jan. 26, 2018, is named 43487770203SL.txt and is 6,833 bytes in size.

BACKGROUND

Samples may be processed for various purposes, such as identification of a type of sample of moiety within the sample. The sample may be a biological sample. The biological samples may be processed for various purposes, such as detection of a disease (e.g., cancer) or identification of a particular species. There are various approaches for processing samples, such as polymerase chain reaction (PCR) and sequencing.

Biological samples may be processed within various reaction environments, such as partitions. Partitions may be wells or droplets. Droplets or wells may be employed to process biological samples in a manner that enables the biological samples to be partitioned and processed separately. For example, such droplets may be fluidically isolated from other droplets, enabling accurate control of respective environments in the droplets.

Biological samples in partitions may be subjected to various processes, such as chemical processes or physical processes. Samples in partitions may be subjected to heating or cooling, or chemical reactions, such as to yield species that may be qualitatively or quantitatively processed.

Certain applications may benefit from the amplification or sequencing of species obtained from single cells obtained from a much larger population. In some cases, the single cells of interest may be quite rare. Thus, there is a need for sample preparation techniques that allow sequencing of nucleic acids from single cells of interest.

SUMMARY

In eukaryotic genomes, chromosomal DNA winds itself around histone proteins (i.e., "nucleosomes"), thereby forming a complex known as chromatin. The tight or loose packaging of chromatin contributes to the control of gene expression. Tightly packed chromatin ("closed chromatin") is usually not permissive for gene expression while more loosely packaged, accessible regions of chromatin ("open chromatin") is associated with the active transcription of gene products. Methods for probing genome-wide DNA accessibility have proven extremely effective in identifying regulatory elements across a variety of cell types and quantifying changes that lead to both activation or repression of gene expression.

One such method is the Assay for Transposase Accessible Chromatin with high-throughput sequencing (ATAC-seq). The ATAC-seq method probes DNA accessibility with an artificial transposon, which inserts specific sequences into accessible regions of chromatin. Because the transposase can only insert sequences into accessible regions of chromatin not bound by transcription factors and/or nucleosomes, sequencing reads can be used to infer regions of increased chromatin accessibility.

Traditional approaches to the ATAC-seq methodology requires large pools of cells, processes cells in bulk, and result in data representative of an entire cell population, but lack information about cell-to-cell variation inherently present in a cell population (see, e.g., Buenrostro, et al., Curr. Protoc. Mol. Biol., 2015 Jan. 5; 21.29.1-21.29.9). While single cell ATAC-seq (scATAC-seq) methods have been developed, they suffer from several limitations. For example, scATAC-seq methods that utilize sample pooling, cell indexing, and cell sorting (see, e.g., Cusanovich, et al., Science, 2015 May 22; 348(6237):910-14) result in high variability and a low number of reads associated with any single cell. Other scATAC-seq methods that utilize a programmable microfluidic device to isolate single cells and perform scATAC-seq in nanoliter reaction chambers (see, e.g., Buenrostro, et al., Nature, 2015 Jul. 23; 523(7561): 486-90) are limited by the throughput of the assay and may not generate personal epigenomic profiles on a timescale compatible with clinical decision-making.

Disclosed herein, in some embodiments, are methods of generating barcoded nucleic acid fragments, comprising: (a) generating a plurality of partitions, wherein at least a subset of the plurality of partitions comprises: (i) a single biological particle from a plurality of biological particles; (ii) a plurality of barcode oligonucleotide molecules comprising a common barcode sequence; (iii) a plurality of transposon end oligonucleotide molecules comprising a transposon end sequence; and (iv) a plurality of transposase molecules, wherein the single biological particle comprises a template nucleic acid; (b) generating a plurality of template nucleic acid fragments by subjecting the subset of the plurality of partitions to conditions sufficient to cause transposition of the transposon end oligonucleotide molecules into the template nucleic acid with the aid of a transposase-nucleic acid complex comprising a transposase molecule from the plurality of transposase molecules and a transposon end oligonucleotide molecule from the plurality of transposon end oligonucleotide molecules; and (c) generating a barcoded nucleic acid fragment using a barcode oligonucleotide molecule from the plurality of barcode oligonucleotide molecule and a template nucleic acid fragment from the plurality of template nucleic acid fragments.

In some embodiments, the barcoded nucleic acid fragment is generated by ligation of the barcode oligonucleotide molecule with the template nucleic acid fragment. In some embodiments, the barcoded nucleic acid fragment is generated by amplification of the template nucleic acid fragment using the barcode oligonucleotide molecule as a primer. In some embodiments, the subset of the plurality of partitions are subjected to conditions sufficient to generate the transposase-nucleic acid complex using a transposase molecule from the plurality of transposase molecules and a transposon end oligonucleotide molecule from the plurality of barcode oligonucleotide molecules. In some embodiments, the transposase-nucleic acid complex is partitioned into the subset of the plurality of partitions.

In some embodiments, the plurality of barcode oligonucleotide molecules are attached to a bead and wherein the subset of the plurality of partitions further comprises a single bead from a plurality of beads. In some embodiments, the bead is a gel bead. In some embodiments, the barcode oligonucleotide molecules are releasably attached to the gel bead. In some embodiments, the method further comprises releasing barcode oligonucleotide molecules from the barcode oligonucleotide molecules from the gel bead. In some embodiments, the subset of the plurality of partitions further comprise a reducing agent to depolymerize the gel bead. In some embodiments, the reducing agent is DTT.

In some embodiments, prior to (b), the subset of the plurality of partitions are subjected to conditions sufficient to cause release of the template nucleic acid molecules from the single biological particle. In some embodiments, subsequent to (b), the subset of the plurality of partitions are subjected to conditions sufficient to cause release of the template nucleic acid fragments from the single biological particle. In some embodiments, the single biological particle is a single cell and wherein the plurality of biological particles is a plurality of cells. In some embodiments, the single biological particle is a single nucleus and wherein the plurality of biological particles are a plurality of nuclei harvested from a plurality of cells. In some embodiments, the plurality of partitions are a plurality of droplets. In some embodiments, the plurality of partitions are a plurality of wells. In some embodiments, the methods further comprise amplifying the barcoded nucleic acid fragment, or a derivative thereof, by nucleic acid amplification. In some embodiments, the barcoded nucleic acid fragment is released from the subset of the plurality of partitions. In some embodiments, the methods further comprise sequencing the barcoded nucleic acid fragment, or a derivative thereof.

In some embodiments, the plurality of transposon end oligonucleotide molecules comprise (i) a plurality of first oligonucleotide molecules comprising a transposon end sequence and a first primer sequence; and (ii) a plurality of second oligonucleotide molecules comprising a transposon end sequence and a second primer sequence. In some embodiments, (i) the first oligonucleotide is a partially double-stranded molecule and comprises a first strand comprising the first primer sequence and the transposon end sequence and a second strand comprising a sequence at least 80% complementary to the transposon end sequence; and (ii) the second oligonucleotide is a partially double-stranded molecule and comprises a first strand comprising the second primer sequence and the transposon end sequence and a second strand comprising a sequence at least 80% complementary to the transposon end sequence In some embodiments, the transposase-nucleic acid complex comprises a transposase molecule from the plurality of transposase molecules, a first oligonucleotide molecule from the plurality of first oligonucleotide molecules, and a second oligonucleotide molecule from the plurality of second oligonucleotide molecules.

In some embodiments, the plurality of barcode oligonucleotide molecules comprise an adapter sequence, a common barcode sequence, and a sequence at least 80% complementary to the first primer sequence. In some embodiments, the plurality of barcode oligonucleotides are partially double-stranded molecules comprising a first strand comprising an adapter sequence, a common barcode sequence, and a sequence at least 80% complementary to the first primer sequence and a second strand comprising a sequence at least 80% complementary to the adapter sequence and a sequence at least 80% complementary to the barcode sequence. In some embodiments, the barcoded nucleic acid fragment is generated by ligation of the barcode oligonucleotide molecule with the template nucleic acid fragment. In some embodiments, subsequent to (b), the plurality of template nucleic acid fragments are subjected to a gap-filling reaction to generate gap-filled, double-stranded template nucleic acid fragments.

In some embodiments, the plurality of template nucleic acid fragments are subjected to a gap-filling reaction to generate gap-filled, double-stranded template nucleic acid fragments and wherein the barcoded nucleic acid fragment is generated by amplification of a gap-filled, double-stranded template nucleic acid fragment with the barcode oligonucleotide molecule. In some embodiments, the plurality of barcode oligonucleotides are single-stranded molecules.

In some embodiments, the subset of the plurality of partitions is generated by: (a) generating a first plurality of partitions comprising a plurality of barcode oligonucleotides comprising the common barcode sequence; a plurality of transposon end oligonucleotides comprising the transposon end sequence; and a plurality of transposase molecules; (b) generating a second plurality of partitions comprising a single biological particle from the plurality of biological particles; and (c) merging a partition from the first plurality of partitions with a partition from the second plurality of partitions thereby generating the subset of the plurality of partitions. In some embodiments, the first primer sequence and the second primer sequence are the same. In some embodiments, the first primer sequence and the second primer sequence are the different. In some embodiments, the barcode oligonucleotide molecules of the plurality of barcode oligonucleotide molecules each comprise: (i) a first oligonucleotide molecule comprising a first sequencing primer sequence and a common barcode sequence; and (ii) a second oligonucleotide molecule comprising a second sequencing primer sequence partially complementary to the first sequencing primer sequence and a sequence complementary to the barcode sequence of the first oligonucleotide molecule. In some embodiments, the barcoded nucleic acid fragment is generated by ligating a barcode oligonucleotide molecule from the plurality of barcode oligonucleotide molecules onto a template nucleic acid fragment from the plurality of template nucleic acid fragments.

In some embodiments, the methods further comprise subjecting the barcoded nucleic acid fragment to one or more reactions to generate a set of nucleic acid molecules for nucleic acid sequencing. In some embodiments, the one or more reactions comprise nucleic acid amplification that generates amplified products from the barcoded nucleic acid fragment. In some embodiments, the nucleic acid amplification adds functional sequences to the amplified products, wherein the functional sequences permit attachment of the amplified products to a flow cell of a sequencer for the nucleic acid sequencing. In some embodiments, the one or more reactions comprise ligating functional sequences to the barcoded nucleic acid fragment, or a derivative thereof, wherein the functional sequences permit attachment to a flow cell of a sequencer for the nucleic acid sequencing. In some embodiments, the methods further comprise ligating functional sequences to the amplified products, wherein the functional sequences permit attachment of the amplified products to a flow cell of a sequencer for the nucleic acid sequencing. In some embodiments, each bead of the plurality of beads comprises a plurality of barcode oligonucleotide molecules comprising a common barcode sequence that is different from barcode sequences in other beads of the plurality of beads. In some embodiments, each of the barcode oligonucleotide molecules comprise the common barcode sequence and a unique molecular sequence, wherein the common barcode sequence is constant across the nucleic acid barcode molecules, and wherein the unique molecular sequence varies across the nucleic acid barcode molecules.

Also disclosed herein, in some embodiments, are methods of generating barcoded nucleic acid fragments, comprising: (a) providing a plurality of biological particles, an individual biological particle comprising a template nucleic acid; (b) generating a plurality of template nucleic acid fragments in biological particles from the plurality of biological particles with the aid of a transposase-nucleic acid complex comprising a transposase molecule and a transposon end oligonucleotide molecule; (c) generating a plurality of partitions, wherein at least a subset of the plurality of partitions comprise a single biological particle comprising template nucleic acid fragments and a plurality of barcode oligonucleotide molecules comprising a barcode sequence; and (d) generating a barcoded nucleic acid fragment using a barcode oligonucleotide molecule from the plurality of barcode oligonucleotide molecule and a template nucleic acid fragment from the plurality of template nucleic acid fragments.

In some embodiments, the plurality of barcode oligonucleotide molecules are attached to a bead and wherein the subset of the plurality of partitions further comprises a single bead from a plurality of beads. In some embodiments, the bead is a gel bead. In some embodiments, the barcode oligonucleotide molecules are releasably attached to the gel bead. In some embodiments, the methods further comprise releasing the barcode oligonucleotide molecules from the gel bead. In some embodiments, the subset of the plurality of partitions further comprise a reducing agent to depolymerize the gel bead. In some embodiments, the reducing agent is DTT. In some embodiments, the plurality of partitions are a plurality of droplets. In some embodiments, the plurality of partitions are a plurality of wells. In some embodiments, the methods further comprise amplifying the barcoded nucleic acid fragment, or a derivative thereof, by nucleic acid amplification. In some embodiments, the barcoded nucleic acid fragment is released from the subset of the plurality of partitions. In some embodiments, the methods further comprise sequencing the barcoded nucleic acid fragment, or a derivative thereof.

In some embodiments, the transposase-nucleic acid complex comprises (i) a first oligonucleotide molecule comprising a transposon end sequence and a first primer sequence; and (ii) a second oligonucleotide molecule comprising a transposon end sequence and a second primer sequence. In some embodiments, (i) the first oligonucleotide is a partially double-stranded molecule and comprises a first strand comprising the first primer sequence and the transposon end sequence and a second strand comprising a sequence at least 80% complementary to the transposon end sequence; and (ii) the second oligonucleotide is a partially double-stranded molecule and comprises a first strand comprising the second primer sequence and the transposon end sequence and a second strand comprising a sequence at least 80% complementary to the transposon end sequence. In some embodiments, the transposase-nucleic acid complex comprises a transposase molecule, a first oligonucleotide molecule, and a second oligonucleotide molecule. In some embodiments, the plurality of barcode oligonucleotide molecules comprise an adapter sequence, a barcode sequence, and a sequence at least 80% complementary to the first primer sequence.

In some embodiments, the plurality of barcode oligonucleotides are partially double-stranded molecules comprising a first strand comprising an adapter sequence, a barcode sequence, and a sequence at least 80% complementary to the first primer sequence and a second strand comprising a sequence at least 80% complementary at least 80% complementary to the adapter sequence and a sequence at least 80% complementary to the barcode sequence. In some embodiments, the barcoded nucleic acid fragment is generated by ligation of the barcode oligonucleotide molecule with the template nucleic acid fragment. In some embodiments, the plurality of barcode oligonucleotide molecules comprise an adapter sequence, a barcode sequence, and a sequence at least 80% complementary to the first primer sequence. In some embodiments, prior to (d), the plurality of template nucleic acid fragments are subjected to a gap-filling reaction to generate gap-filled, double-stranded template nucleic acid fragments. In some embodiments, the plurality of template nucleic acid fragments are subjected to a gap-filling reaction to generate gap-filled, double-stranded template nucleic acid fragments and wherein the barcoded nucleic acid fragment is generated by amplification of a template nucleic acid fragment, or a derivative thereof, with the barcode oligonucleotide molecule. In some embodiments, the plurality of barcode oligonucleotides are single-stranded molecules.

In some embodiments, the methods further comprise sequencing the barcoded template nucleic acid fragment, or a derivative thereof. In some embodiments, the template nucleic acid comprises chromatin. In some embodiments, the plurality of biological particles are a plurality of nuclei harvested from a plurality of cells. In some embodiments, the plurality of biological particles are a plurality of cells. In some embodiments, the barcoded nucleic acid fragments, or derivatives thereof, are indicative of regions of accessible chromatin in the single biological particle. In some embodiments, the first primer sequence and the second primer sequence are the same. In some embodiments, the first primer sequence and the second primer sequence are the different.

In some embodiments, the methods further comprise subjecting the barcoded nucleic acid fragment to one or more reactions to generate a set of nucleic acid molecules for nucleic acid sequencing. In some embodiments, the one or more reactions comprise nucleic acid amplification that generates amplified products from the barcoded nucleic acid fragment. In some embodiments, the nucleic acid amplification adds functional sequences to the amplified products, wherein the functional sequences permit attachment of the amplified products to a flow cell of a sequencer for the nucleic acid sequencing. In some embodiments, the one or more reactions comprise ligating functional sequences to the barcoded nucleic acid fragment, or a derivative thereof, wherein the functional sequences permit attachment to a flow cell of a sequencer for the nucleic acid sequencing. In some embodiments, the methods further comprise ligating functional sequences to the amplified products, wherein the functional sequences permit attachment of the amplified products to a flow cell of a sequencer for the nucleic acid sequencing. In some embodiments, each bead of the plurality of beads comprises a plurality of barcode oligonucleotide molecules comprising a common barcode sequence that is different from barcode sequences in other beads of the plurality of beads. In some embodiments, each of the barcode oligonucleotide molecules comprise the common barcode sequence and a unique molecular sequence, wherein the common barcode sequence is constant across the nucleic acid barcode molecules, and wherein the unique molecular sequence varies across the nucleic acid barcode molecules.

Disclosed herein, in some embodiments, are methods of generating barcoded nucleic acid fragments, comprising: (a) generating a plurality of partitions, wherein at least a subset of the plurality of partitions comprises: (i) a single biological particle from a plurality of biological particles, wherein the single biological particle comprises template DNA molecules and template RNA molecules; (ii) a plurality of first barcode oligonucleotide molecules comprising a barcode sequence; (iii) a plurality of transposon end oligonucleotide molecules comprising a transposon end sequence; (iv) a plurality of transposase molecules; (v) a plurality of second barcode oligonucleotide molecules comprising a barcode sequence and a capture sequence; and (vi) a plurality of reverse transcriptase molecules; (b) generating a plurality of template DNA fragments by subjecting the subset of the plurality of partitions to conditions sufficient to cause transposition of the transposon end oligonucleotide molecules into the template DNA with the aid of a transposase-nucleic acid complex comprising a transposase molecule from the plurality of transposase molecules and a transposon end oligonucleotide molecule from the plurality of transposon end oligonucleotide molecules; (c) generating a barcoded DNA fragment using a barcode oligonucleotide molecule from the plurality of first barcode oligonucleotide molecules and a template DNA fragment from the plurality of template DNA fragments; and (d) generating a barcoded cDNA molecule from the template RNA molecules by reverse transcription using a barcode oligonucleotide molecule from the plurality of second barcode oligonucleotide molecules.

In some embodiments, the capture sequence is an oligo (dT) sequence. In some embodiments, step (d) generates a first strand barcoded cDNA molecule and the method further comprises generating a second strand barcoded cDNA molecule. In some embodiments, the plurality of partitions further comprise a plurality of template switching oligonucleotides and wherein the second strand of the barcoded cDNA molecule is generated by a template switching oligonucleotide from the plurality of template switching oligonucleotides. In some embodiments, the template switching oligonucleotide comprises a barcode sequence. In some embodiments, the barcode sequence from the template switching oligonucleotide is the same as the barcode sequence from the first barcode oligonucleotide and the second barcode oligonucleotide.

In some embodiments, the subset of the plurality of partitions are subjected to conditions sufficient to generate the transposase-nucleic acid complex using a transposase molecule from the plurality of transposase molecules and a barcode oligonucleotide molecule from the plurality of barcode oligonucleotide molecules. In some embodiments, the transposase-nucleic acid complex is partitioned into the subset of the plurality of partitions. In some embodiments, prior to (b), the subset of the plurality of partitions are subjected to conditions sufficient to cause release of the template DNA molecules and the template RNA molecules from the single biological particle. In some embodiments, subsequent to (b), the subset of the plurality of partitions are subjected to conditions sufficient to cause release of the template DNA fragments and the template RNA molecules from the single biological particle.

In some embodiments, (i) the plurality of first barcode oligonucleotide molecules are attached to a first bead, the plurality of second barcode oligonucleotide molecules are attached to a second bead, and wherein the subset of the plurality of partitions comprises a single first bead from a plurality of first beads and a single second bead from a plurality of second beads; or (ii) the plurality of first barcode oligonucleotide molecules and the plurality of second barcode oligonucleotide molecules are attached to a bead, wherein the subset of the plurality of partitions comprises a single bead from a plurality of beads. In some embodiments, the bead is a gel bead. In some embodiments, the plurality of first barcode oligonucleotide molecules and the plurality of second barcode oligonucleotide molecules are releasably attached to the gel bead. In some embodiments, the methods further comprise releasing first barcode oligonucleotide molecules from the plurality of first barcode oligonucleotide molecules and second barcode oligonucleotide molecules from the plurality of second barcode oligonucleotide molecules from the gel bead. In some embodiments, the gel bead is depolymerized to release the barcode molecules from the gel bead. In some embodiments, the subset of the plurality of partitions further comprise a reducing agent to depolymerize the gel bead.

In some embodiments, the single biological particle is a single cell and wherein the plurality of biological particles is a plurality of cells. In some embodiments, the single biological particle is a single nucleus and wherein the plurality of biological particles are a plurality of nuclei harvested from a plurality of cells. In some embodiments, the plurality of partitions are a plurality of droplets. In some embodiments, the plurality of partitions are a plurality of wells.

In some embodiments, the plurality of first barcode oligonucleotide molecules are attached to a gel bead, wherein the plurality of second barcode oligonucleotide molecules are attached to a plurality of magnetic beads, and wherein the plurality of magnetic beads are embedded within the gel bead, and wherein the subset of the plurality of partitions comprise a single gel bead comprising the plurality of magnetic beads. In some embodiments, the plurality of first barcode oligonucleotide molecules are releasably attached to the gel bead. In some embodiments, the methods further comprise releasing first barcode oligonucleotide molecules from the plurality of first barcode oligonucleotide molecules and magnetic beads from the plurality of magnetic beads from the gel bead. In some embodiments, the gel bead is depolymerized to release the first barcode oligonucleotide molecules and the magnetic particles from the gel bead. In some embodiments, the subset of the plurality of partitions further comprise a reducing agent to depolymerize the gel bead. In some embodiments, the reducing agent is DTT.

In some embodiments, the barcoded DNA fragment and the barcoded cDNA molecule is released from the subset of the plurality of partitions. In some embodiments, the methods further comprise sequencing the barcoded DNA fragment, or a derivative thereof. In some embodiments, the methods further comprise sequencing the barcoded cDNA molecule, or a derivative thereof. In some embodiments, the barcode sequence on the first barcode oligonucleotide and the barcode sequence on the second barcode oligonucleotide are the same. In some embodiments, the barcode sequence on the first barcode oligonucleotide and the barcode sequence on the second barcode oligonucleotide are the different.

In some embodiments, the methods further comprise subjecting the barcoded nucleic acid fragment to one or more reactions to generate a set of nucleic acid molecules for nucleic acid sequencing. In some embodiments, the one or more reactions comprise nucleic acid amplification that generates amplified products from the barcoded nucleic acid fragment. In some embodiments, the nucleic acid amplification adds functional sequences to the amplified products, wherein the functional sequences permit attachment of the amplified products to a flow cell of a sequencer for the nucleic acid sequencing. In some embodiments, the one or more reactions comprise ligating functional sequences to the barcoded nucleic acid fragment, or a derivative thereof, wherein the functional sequences permit attachment to a flow cell of a sequencer for the nucleic acid sequencing. In some embodiments, the methods further comprise ligating functional sequences to the amplified products, wherein the functional sequences permit attachment of the amplified products to a flow cell of a sequencer for the nucleic acid sequencing. In some embodiments, each bead of the plurality of beads comprises a plurality of barcode oligonucleotide molecules comprising a common barcode sequence that is different from barcode sequences in other beads of the plurality of beads. In some embodiments, each of the barcode oligonucleotide molecules comprise the common barcode sequence and a unique molecular sequence, wherein the common barcode sequence is constant across the nucleic acid barcode molecules, and wherein the unique molecular sequence varies across the nucleic acid barcode molecules.

Also disclosed herein, in some embodiments, are methods of generating barcoded nucleic acid fragments, comprising: (a) providing a plurality of biological particles, an individual biological particle comprising template DNA molecules and template RNA molecules; (b) generating a plurality of template DNA fragments in biological particles from the plurality of biological particles with the aid of a transposase-nucleic acid complex comprising a transposase molecule and a transposon end oligonucleotide molecule; (c) generating a plurality of partitions, wherein at least a subset of the plurality of partitions comprises (i) a single biological particle comprising template DNA fragments and template RNA molecules; (ii) a plurality of first barcode oligonucleotide molecules comprising a barcode sequence; (iii) a plurality of second barcode oligonucleotide molecules comprising a barcode sequence and a capture sequence; and (iv) a plurality of reverse transcriptase molecules; (d) generating a barcoded DNA fragment using a barcode oligonucleotide molecule from the plurality of first barcode oligonucleotide molecules and a template DNA fragment from the plurality of template DNA fragments; and (e) generating a barcoded cDNA molecule from the template RNA molecules by reverse transcription using a barcode oligonucleotide molecule from the plurality of second barcode oligonucleotide molecules.

In some embodiments, the plurality of biological particle are a plurality of nuclei harvested from a plurality of cells and wherein the single biological particle is a single nucleus. In some embodiments, the plurality of biological particles are a plurality of cells and wherein the single biological particle is a single cell. In some embodiments, the barcode sequence on the plurality of first barcode oligonucleotide molecules and the barcode sequence on the plurality of second barcode oligonucleotide molecules are the same. In some embodiments, the barcode sequence on the plurality of first barcode oligonucleotide molecules and the barcode sequence on the plurality of second barcode oligonucleotide molecules are different. In some embodiments, the capture sequence is an oligo(dT) sequence.

In some embodiments, step (e) generates a first strand barcoded cDNA molecule and the method further comprises generating a second strand barcoded cDNA molecule. In some embodiments, the plurality of partitions further comprises a plurality of template switching oligonucleotides and wherein the second strand of the barcoded cDNA molecule is generated by a template switching oligonucleotide from the plurality of template switching oligonucleotides. In some embodiments, the template switching oligonucleotide comprises a barcode sequence. In some embodiments, the barcode sequence from the template switching oligonucleotide; the barcode sequence from the first barcode oligonucleotide molecules; and the barcode sequence from the second barcode oligonucleotide molecules are the same. In some embodiments, the barcode sequence from the template switching oligonucleotide; the barcode sequence from the first barcode oligonucleotide molecules; and the barcode sequence from the second barcode oligonucleotide molecules are different. In some embodiments, the subset of the plurality of partitions are subjected to conditions sufficient to cause release of the template DNA molecules and the template RNA molecules from the single biological particle.

In some embodiments, (i) the plurality of first barcode oligonucleotide molecules are attached to a first bead, the plurality of second barcode oligonucleotide molecules are attached to a second bead, and wherein the subset of the subset of the plurality of partitions comprises a single first bead from a plurality of first beads and a single second bead from a plurality of second beads; or (ii) wherein the plurality of first barcode oligonucleotide molecules and the plurality of second barcode oligonucleotide molecules are attached to a bead, wherein the subset of the plurality of partitions comprises a single bead from a plurality of beads, wherein the single bead comprises the first barcode oligonucleotide molecules and the second barcode oligonucleotide molecules. In some embodiments, the bead is a gel bead. In some embodiments, the plurality of first barcode oligonucleotide molecules and the plurality of second barcode oligonucleotide molecules are releasably attached to the gel bead. In some embodiments, the methods further comprise releasing first barcode oligonucleotide molecules from the plurality of first barcode oligonucleotide molecules and second barcode oligonucleotide molecules from the plurality of second barcode oligonucleotide molecules from the gel bead. In some embodiments, the gel bead is depolymerized to release the barcode molecules from the gel bead. In some embodiments, the subset of the plurality of partitions further comprise a reducing agent to depolymerize the gel bead. In some embodiments, the reducing agent is DTT.

In some embodiments, the plurality of partitions are a plurality of droplets. In some embodiments, the plurality of partitions are a plurality of wells.

In some embodiments, the plurality of first barcode oligonucleotide molecules are attached to a gel bead, wherein the plurality of second barcode oligonucleotide molecules are attached to a plurality of magnetic beads, wherein the plurality of magnetic beads are embedded within the gel bead, and wherein the subset of the plurality of partitions comprises a single gel bead comprising the plurality of magnetic beads. In some embodiments, the plurality of first barcode oligonucleotide molecules are releasably attached to the gel bead. In some embodiments, the methods further comprise releasing first barcode oligonucleotide molecules from the plurality of first barcode oligonucleotide molecules and magnetic beads from the plurality of magnetic beads from the gel bead. In some embodiments, the gel bead is depolymerized to release the first barcode oligonucleotide molecules and the magnetic beads from the gel bead. In some embodiments, the subset of the plurality of partitions further comprise a reducing agent to depolymerize the gel bead. In some embodiments, the reducing agent is DTT.

In some embodiments, the barcoded DNA fragment and the barcoded cDNA molecule is released from the subset of the plurality of partitions. In some embodiments, the methods further comprise (a) sequencing the barcoded DNA fragment, or a derivative thereof, (b) sequencing the barcoded cDNA molecule, or a derivative thereof, or (c) sequencing the barcoded DNA fragment and the barcoded cDNA molecule, or derivatives thereof. In some embodiments, the barcoded DNA fragment, or derivatives thereof, are indicative of regions of accessible chromatin in the single biological particle.

In some embodiments, the methods further comprise subjecting the barcoded nucleic acid fragment to one or more reactions to generate a set of nucleic acid molecules for nucleic acid sequencing. In some embodiments, the one or more reactions comprise nucleic acid amplification that generates amplified products from the barcoded nucleic acid fragment. In some embodiments, the nucleic acid amplification adds functional sequences to the amplified products, wherein the functional sequences permit attachment of the amplified products to a flow cell of a sequencer for the nucleic acid sequencing. In some embodiments, the one or more reactions comprise ligating functional sequences to the barcoded nucleic acid fragment, or a derivative thereof, wherein the functional sequences permit attachment to a flow cell of a sequencer for the nucleic acid sequencing. In some embodiments, the methods further comprise ligating functional sequences to the amplified products, wherein the functional sequences permit attachment of the amplified products to a flow cell of a sequencer for the nucleic acid sequencing. In some embodiments, each bead of the plurality of beads comprises a plurality of barcode oligonucleotide molecules comprising a common barcode sequence that is different from barcode sequences in other beads of the plurality of beads. In some embodiments, each of the barcode oligonucleotide molecules comprise the common barcode sequence and a unique molecular sequence, wherein the common barcode sequence is constant across the nucleic acid barcode molecules, and wherein the unique molecular sequence varies across the nucleic acid barcode molecules.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 11A illustrates an exemplary method for the in-partition transposition of sequencing adaptors into native chromatin while FIG. 11B illustrates an exemplary method for the in-bulk production of a next-generation sequencing compatible library from the fragments produced in FIG. 11A.

FIG. 12A discloses SEQ ID NOS 8, 9, 8, and 9, respectively, in order of appearance. FIG. 12B discloses SEQ ID NOS 10, 11, 10, and 11, respectively, in order of appearance.

FIG. 14A illustrates an exemplary method for the in-partition ligation of forked adaptors onto fragments of native chromatin generated by an in-partition transposition reaction. FIG. 14B illustrates an exemplary method for the in-bulk production of a next-generation sequencing compatible library from the fragments produced in FIG. 14A.

FIG. 15A discloses SEQ ID NOS 12, 13, 8, 13, 14, 15, 14, and 15. 15B disclose SEQ ID NOS 16, 17, 10, 18, 14, 15, 14, and 15, respectively, in order of appearance.

FIG. 18 discloses SEQ ID NOS 19, 15, 19, and 15, respectively, in order of appearance.

FIG. 21 discloses SEQ ID NOS 20, 15, 20, and 15, respectively, in order of appearance.

In FIG. 24B, the first and the second primer sequence are the same.

FIG. 25A illustrates a partially double-stranded oligonucleotide releasably attached to a gel bead, the first strand comprising a transposon end sequence, a barcode sequence, and a first primer sequence and a second strand comprising a sequence complementary to the transposon end sequence. FIG. 25B illustrates a partially double-stranded oligonucleotide releasably attached to a gel bead, the first strand comprising a transposon end sequence and a barcode sequence and the second strand comprising a sequence complementary to the transposon end sequence

FIG. 28A illustrates an exemplary transposase-nucleic acid complex showing a transposase, a first double-stranded oligonucleotide comprising a transposon end sequence and a second double-stranded oligonucleotide comprising a transposon end sequence. FIG. 28B illustrates an exemplary barcoded adaptor comprising a transposon end sequence, a barcode sequence, and a primer sequence releasably attached to a gel bead.

FIG. 29A illustrates an exemplary transposase-nucleic acid complex showing a transposase, a first double-stranded oligonucleotide comprising a transposon end sequence and a first primer sequence and a second double-stranded oligonucleotide comprising a transposon end sequence and a second primer sequence. FIG. 28B illustrates an exemplary barcoded adaptor comprising an adapter sequence, a barcode sequence, and a sequence complementary to the first primer sequence.

FIGS. 28C-D illustrates an exemplary barcoding scheme.

FIG. 32A illustrates an exemplary barcode oligonucleotide; FIG. 32B illustrates an exemplary combination of bulk/in-partition barcoding scheme using CRISPR/Cas-9 mediated cleavage; FIG. 32C illustrates an exemplary in-partition barcoding scheme using CRISPR/Cas-9 mediated cleavage.

FIG. 33A illustrates an exemplary forked barcode oligonucleotide; FIG. 33B illustrates an exemplary combination of bulk/in-partition barcoding scheme using CRISPR/Cas-9 mediated cleavage; FIG. 33C illustrates an exemplary in-partition barcoding scheme using CRISPR/Cas-9 mediated cleavage.

DETAILED DESCRIPTION

Figure 1:
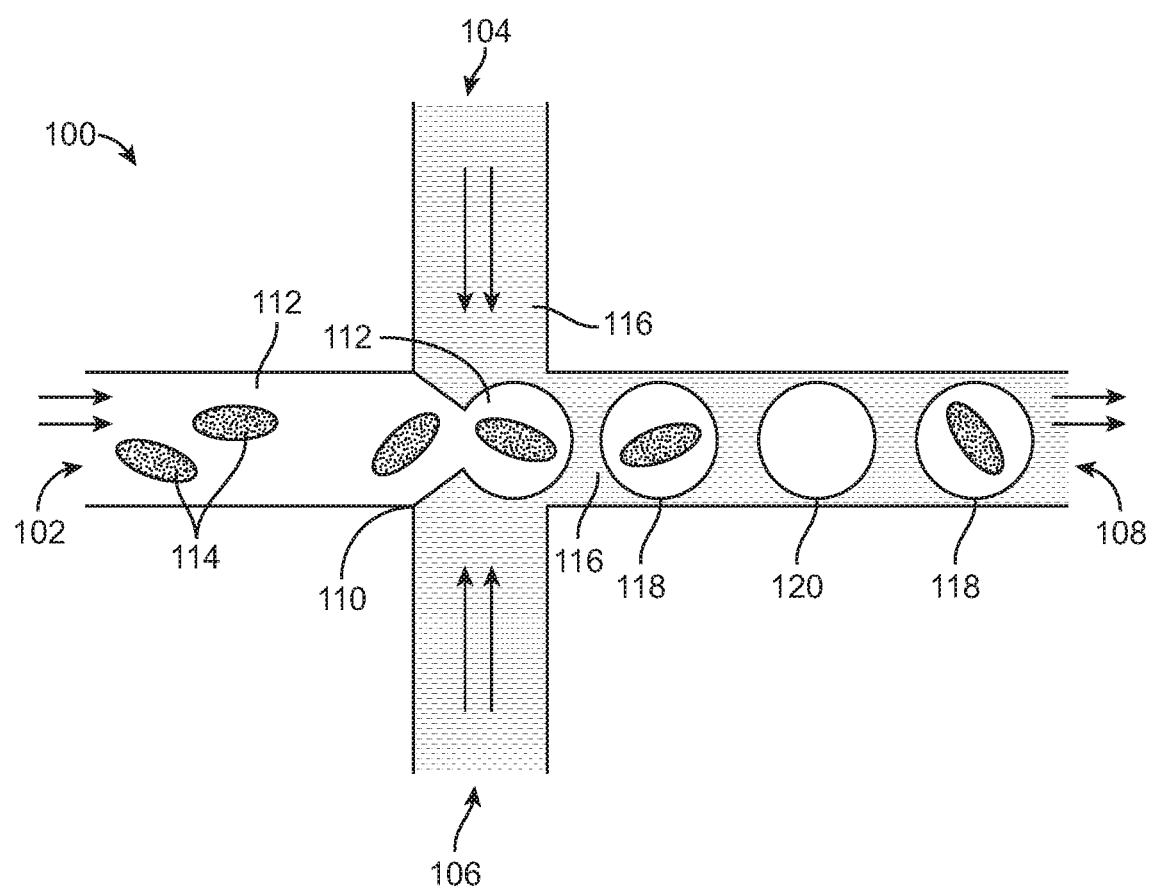
FIG. 1 shows an example of a microfluidic channel structure for partitioning individual biological particles.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be independent of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads.

The term "real time," as used herein, can refer to a response time of less than about 1 second, a tenth of a second, a hundredth of a second, a millisecond, or less. The response time may be greater than 1 second. In some instances, real time can refer to simultaneous or substantially simultaneous processing, detection or identification.

The term "subject," as used herein, generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

The term "genome," as used herein, generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach, including ligation, hybridization, or other approaches.

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "bead," as used herein, generally refers to a particle. The bead may be a solid or semi-solid particle. The bead may be a gel bead. The gel bead may include a polymer matrix (e.g., matrix formed by polymerization or cross-linking). The polymer matrix may include one or more polymers (e.g., polymers having different functional groups or repeat units). Polymers in the polymer matrix may be randomly arranged, such as in random copolymers, and/or have ordered structures, such as in block copolymers. Cross-linking can be via covalent, ionic, or inductive, interactions, or physical entanglement. The bead may be a macromolecule. The bead may be formed of nucleic acid molecules bound together. The bead may be formed via covalent or non-covalent assembly of molecules (e.g., macromolecules), such as monomers or polymers. Such polymers or monomers may be natural or synthetic. Such polymers or monomers may be or include, for example, nucleic acid molecules (e.g., DNA or RNA). The bead may be formed of a polymeric material. The bead may be magnetic or non-magnetic. The bead may be rigid. The bead may be flexible and/or compressible. The bead may be disruptable or dissolvable. The bead may be a solid particle (e.g., a metal-based particle including but not limited to iron oxide, gold or silver) covered with a coating comprising one or more polymers. Such coating may be disruptable or dissolvable.

The term "sample," as used herein, generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a macromolecule. The biological particle may be a small molecule. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell type, mycoplasmas, normal tissue cells, tumor cells, or any other cell type, whether derived from single cell or multicellular organisms. The biological particle may be a constituent of a cell. The biological particle may be or may include DNA, RNA, organelles, proteins, or any combination thereof. The biological particle may be or include a chromosome or other portion of a genome. The biological particle may be or may include a matrix (e.g., a gel or polymer matrix) comprising a cell or one or more constituents from a cell (e.g., cell bead), such as DNA, RNA, organelles, proteins, or any combination thereof, from the cell. The biological particle may be obtained from a tissue of a subject. The biological particle may be a hardened cell. Such hardened cell may or may not include a cell wall or cell membrane. The biological particle may include one or more constituents of a cell, but may not include other constituents of the cell. An example of such constituents is a nucleus or an organelle. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within or from a biological particle. The macromolecular constituent may comprise a nucleic acid. In some cases, the biological particle may be a macromolecule. The macromolecular constituent may comprise DNA. The macromolecular constituent may comprise RNA. The RNA may be coding or non-coding. The RNA may be messenger RNA (mRNA), ribosomal RNA (rRNA) or transfer RNA (tRNA), for example. The RNA may be a transcript. The RNA may be small RNA that are less than 200 nucleic acid bases in length, or large RNA that are greater than 200 nucleic acid bases in length. Small RNAs may include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA may be double-stranded RNA or single-stranded RNA. The RNA may be circular RNA. The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise a nucleic acid sequence. The nucleic acid sequence may be at least a portion or an entirety of the molecular tag. The molecular tag may be a nucleic acid molecule or may be part of a nucleic acid molecule. The molecular tag may be an oligonucleotide or a polypeptide. The molecular tag may comprise a DNA aptamer. The molecular tag may be or comprise a primer. The molecular tag may be, or comprise, a protein. The molecular tag may comprise a polypeptide. The molecular tag may be a barcode.

The term "partition," as used herein, generally refers to a space or volume that may be suitable to contain one or more species or conduct one or more reactions. A partition may be a physical compartment, such as a droplet or well. The partition may isolate space or volume from another space or volume. The droplet may be a first phase (e.g., aqueous phase) in a second phase (e.g., oil) immiscible with the first phase. The droplet may be a first phase in a second phase that does not phase separate from the first phase, such as, for example, a capsule or liposome in an aqueous phase. A partition may comprise one or more other (inner) partitions. In some cases, a partition may be a virtual compartment that can be defined and identified by an index (e.g., indexed libraries) across multiple and/or remote physical compartments. For example, a physical compartment may comprise a plurality of virtual compartments.

Single Cell Assay for Transposase Accessible Chromatin Using Sequencing (ATAC-Seq)

Disclosed herein, in some embodiments, are methods of generating barcoded nucleic acid fragments, comprising: (a) generating a plurality of partitions, wherein at least a subset of the plurality of partitions comprises: (i) a single biological particle from a plurality of biological particles; (ii) a plurality of barcode oligonucleotide molecules comprising a common barcode sequence; (iii) a plurality of transposon end oligonucleotide molecules comprising a transposon end sequence; and (iv) a plurality of transposase molecules, wherein the single biological particle comprises a template nucleic acid; (b) generating a plurality of template nucleic acid fragments by subjecting the subset of the plurality of partitions to conditions sufficient to cause transposition of the transposon end oligonucleotide molecules into the template nucleic acid with the aid of a transposase-nucleic acid complex comprising a transposase molecule from the plurality of transposase molecules and a transposon end oligonucleotide molecule from the plurality of transposon end oligonucleotide molecules; and (c) generating a barcoded nucleic acid fragment using a barcode oligonucleotide molecule from the plurality of barcode oligonucleotide molecule and a template nucleic acid fragment from the plurality of template nucleic acid fragments.

Also disclosed herein, in some embodiments, are methods of generating barcoded nucleic acid fragments, comprising: (a) providing a plurality of biological particles, an individual biological particle comprising a template nucleic acid; (b) generating a plurality of template nucleic acid fragments in biological particles from the plurality of biological particles with the aid of a transposase-nucleic acid complex comprising a transposase molecule and a transposon end oligonucleotide molecule; (c) generating a plurality of partitions, wherein at least a subset of the plurality of partitions comprise a single biological particle comprising template nucleic acid fragments and a plurality of barcode oligonucleotide molecules comprising a barcode sequence; and (d) generating a barcoded nucleic acid fragment using a barcode oligonucleotide molecule from the plurality of barcode oligonucleotide molecule and a template nucleic acid fragment from the plurality of template nucleic acid fragments.

Disclosed herein, in some embodiments, are methods of generating barcoded nucleic acid fragments, comprising: (a) generating a plurality of partitions, wherein at least a subset of the plurality of partitions comprises: (i) a single biological particle from a plurality of biological particles, wherein the single biological particle comprises template DNA molecules and template RNA molecules; (ii) a plurality of first barcode oligonucleotide molecules comprising a barcode sequence; (iii) a plurality of transposon end oligonucleotide molecules comprising a transposon end sequence; (iv) a plurality of transposase molecules; (v) a plurality of second barcode oligonucleotide molecules comprising a barcode sequence and a capture sequence; and (vi) a plurality of reverse transcriptase molecules; (b) generating a plurality of template DNA fragments by subjecting the subset of the plurality of partitions to conditions sufficient to cause transposition of the transposon end oligonucleotide molecules into the template DNA with the aid of a transposase-nucleic acid complex comprising a transposase molecule from the plurality of transposase molecules and a transposon end oligonucleotide molecule from the plurality of transposon end oligonucleotide molecules; (c) generating a barcoded DNA fragment using a barcode oligonucleotide molecule from the plurality of first barcode oligonucleotide molecules and a template DNA fragment from the plurality of template DNA fragments; and (d) generating a barcoded cDNA molecule from the template RNA molecules by reverse transcription using a barcode oligonucleotide molecule from the plurality of second barcode oligonucleotide molecules.

Also disclosed herein, in some embodiments, are methods of generating barcoded nucleic acid fragments, comprising: (a) providing a plurality of biological particles, an individual biological particle comprising template DNA molecules and template RNA molecules; (b) generating a plurality of template DNA fragments in biological particles from the plurality of biological particles with the aid of a transposase-nucleic acid complex comprising a transposase molecule and a transposon end oligonucleotide molecule; (c) generating a plurality of partitions, wherein at least a subset of the plurality of partitions comprises (i) a single biological particle comprising template DNA fragments and template RNA molecules; (ii) a plurality of first barcode oligonucleotide molecules comprising a barcode sequence; (iii) a plurality of second barcode oligonucleotide molecules comprising a barcode sequence and a capture sequence; and (iv)

a plurality of reverse transcriptase molecules; (d) generating a barcoded DNA fragment using a barcode oligonucleotide molecule from the plurality of first barcode oligonucleotide molecules and a template DNA fragment from the plurality of template DNA fragments; and (e) generating a barcoded cDNA molecule from the template RNA molecules by reverse transcription using a barcode oligonucleotide molecule from the plurality of second barcode oligonucleotide molecules.

In some embodiments, the transposase is a Tn5 transposase. In some embodiments, the transposase is a mutated, hyperactive Tn5 transposase. In some embodiments, the transposase is a Mu transposase. In some embodiments, the partitions disclosed in (a) further comprise cell lysis reagents; and/or (b) reagent and buffers necessary to carry out one or more reactions.

In some embodiments, a partition comprises a single cell and is processed according to the methods described herein. In some embodiments, a partition comprises a single cell a single nucleus and is partitioned and processed according to the methods described herein. In some embodiments, a partition comprises chromatin from a single cell or single nucleus (e.g., a single chromosome or other portion of the genome) and is partitioned and processed according to the methods described herein. In some embodiments, the transposition reactions and methods described herein are performed in bulk and biological particles (e.g., nuclei/cells/chromatin from single cells) are then partitioned such that, in some portions, a single biological particle occupies a partition.

In some embodiments, the oligonucleotides described herein comprise a transposon end sequence. In some embodiments, the transposon end sequence is a Tn5 or modified Tn5 transposon end sequence. In some embodiments, the transposon end sequence is a Mu transposon end sequence. In some embodiments, the transposon end sequence has a sequence of AGATGTGTATAAGAGACA (SEQ ID NO: 1). In some embodiments, the oligonucleotides described herein comprise an R1 sequencing priming region. In some embodiments, the R1 sequencing primer region has a sequence of TCTACACTCTTTCCCTACACGACGCTCTTCCGATCT (SEQ ID NO: 2), or some portion thereof. In some embodiments, the R1 sequencing primer region has a sequence of TCGTCGGCAGCGTCAGATGTGTATAAGAGACAG (SEQ ID NO: 3), or some portion thereof. In some embodiments, the oligonucleotides described herein comprise a partial R1 sequence. In some embodiments, the partial R1 sequence is ACTACACGACGCTCTTCCGATCT (SEQ ID NO: 4). In some embodiments, the oligonucleotides described herein comprise an R2 sequencing priming region. In some embodiments, the R2 sequencing primer region has a sequence of GTGACTGGAGTTCAGACGTGTGCTCTTCCGATCT (SEQ ID NO: 5), or some portion thereof. In some embodiments, the R2 sequencing primer region has a sequence of GTCTCGTGGGCTCGGAGATGTGTATAAGAGACAG (SEQ ID NO: 6), or some portion thereof. In some embodiments, the oligonucleotides described herein comprise a T7 promoter sequence. In some embodiments, the T7 promoter sequence is TAATACGACTCACTATAG (SEQ ID NO: 7). In some embodiments, the oligonucleotides described herein comprise a region at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to anyone of SEQ ID NO: 1-7. In some embodiments, the oligonucleotides described herein comprise a P5 sequence. In some embodiments, the oligonucleotides described herein comprise a P7 sequence. In some embodiments, the oligonucleotides described herein comprise a sample index sequence.

In some embodiments, the oligonucleotides described herein are attached to a solid support. In some embodiments, the oligonucleotides described herein are attached to a bead. In some embodiments, the bead is a gel bead. In some embodiments, the oligonucleotides described herein are releasably attached to a gel bead. In some embodiments, the oligonucleotides described herein are single-stranded and the first strand attached to a gel bead. In some embodiments, the oligonucleotides described herein are double-stranded or partially double-stranded molecules and the first strand is releasably attached to a gel bead. In some embodiments, the oligonucleotides described herein are double-stranded or partially double-stranded molecules and the second strand is releasably attached to a gel bead. In some embodiments, the oligonucleotides described herein are double-stranded or partially double-stranded molecules and both the first and the second strand are releasably attached to a gel bead or gel beads.

Systems and Methods for Sample Compartmentalization

In an aspect, the systems and methods described herein provide for the compartmentalization, depositing, or partitioning of one or more particles (e.g., biological particles, macromolecular constituents of biological particles, beads, reagents, etc.) into discrete compartments or partitions (referred to interchangeably herein as partitions), where each partition maintains separation of its own contents from the contents of other partitions. The partition can be a droplet in an emulsion. A partition may comprise one or more other partitions.

A partition may include one or more particles. A partition may include one or more types of particles. For example, s partition of the present disclosure may comprise one or more biological particles and/or macromolecular constituents thereof. A partition may comprise one or more gel beads. A partition may comprise one or more cell beads. A partition may include a single gel bead, a single cell bead, or both a single cell bead and single gel bead. A partition may include one or more reagents. Alternatively, a partition may be unoccupied. For example, a partition may not comprise a bead. A cell bead can be a biological particle and/or one or more of its macromolecular constituents encased inside of a gel or polymer matrix, such as via polymerization of a droplet containing the biological particle and precursors capable of being polymerized or gelled. Unique identifiers, such as barcodes, may be injected into the droplets previous to, subsequent to, or concurrently with droplet generation, such as via a microcapsule (e.g., bead), as described elsewhere herein. Microfluidic channel networks (e.g., on a chip) can be utilized to generate partitions as described herein. Alternative mechanisms may also be employed in the partitioning of individual biological particles, including porous membranes through which aqueous mixtures of cells are extruded into non-aqueous fluids.

The partitions can be flowable within fluid streams. The partitions may comprise, for example, micro-vesicles that have an outer barrier surrounding an inner fluid center or core. In some cases, the partitions may comprise a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase.

In some examples, the partitions may be provided in a water-in-oil emulsion or oil-in-water emulsion. A variety of different vessels are described in, for example, U.S. Patent Application Publication No. 2014/0155295, which is entirely incorporated herein by reference for all purposes. Emulsion systems for creating stable droplets in non-aqueous or oil continuous phases are described in, for example, U.S. Patent Application Publication No. 2010/0105112, which is entirely incorporated herein by reference for all purposes.

In the case of droplets in an emulsion, allocating individual particles to discrete partitions may in one non-limiting example be accomplished by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters may be adjusted to control the occupancy of the resulting partitions (e.g., number of biological particles per partition, number of beads per partition, etc.). For example, partition occupancy can be controlled by providing the aqueous stream at a certain concentration and/or flow rate of particles. To generate single biological particle partitions, the relative flow rates of the immiscible fluids can be selected such that, on average, the partitions may contain less than one biological particle per partition in order to ensure that those partitions that are occupied are primarily singly occupied. In some cases, partitions among a plurality of partitions may contain at most one biological particle (e.g., bead, DNA, cell or cellular material). In some embodiments, the various parameters (e.g., fluid properties, particle properties, microfluidic architectures, etc.) may be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

FIG. 1 shows an example of a microfluidic channel structure 100 for partitioning individual biological particles. The channel structure 100 can include channel segments 102, 104, 106 and 108 communicating at a channel junction 110. In operation, a first aqueous fluid 112 that includes suspended biological particles (or cells) 114 may be transported along channel segment 102 into junction 110, while a second fluid 116 that is immiscible with the aqueous fluid 112 is delivered to the junction 110 from each of channel segments 104 and 106 to create discrete droplets 118, 120 of the first aqueous fluid 112 flowing into channel segment 108, and flowing away from junction 110. The channel segment 108 may be fluidically coupled to an outlet reservoir where the discrete droplets can be stored and/or harvested. A discrete droplet generated may include an individual biological particle 114 (such as droplets 118). A discrete droplet generated may include more than one individual biological particle 114 (not shown in FIG. 1). A discrete droplet may contain no biological particle 114 (such as droplet 120). Each discrete partition may maintain separation of its own contents (e.g., individual biological particle 114) from the contents of other partitions.

The second fluid 116 can comprise an oil, such as a fluorinated oil, that includes a fluorosurfactant for stabilizing the resulting droplets, for example, inhibiting subsequent coalescence of the resulting droplets 118, 120. Examples of particularly useful partitioning fluids and fluorosurfactants are described, for example, in U.S. Patent Application Publication No. 2010/0105112, which is entirely incorporated herein by reference for all purposes.

As will be appreciated, the channel segments described herein may be coupled to any of a variety of different fluid sources or receiving components, including reservoirs, tubing, manifolds, or fluidic components of other systems. As will be appreciated, the microfluidic channel structure 100 may have other geometries. For example, a microfluidic channel structure can have more than one channel junction. For example, a microfluidic channel structure can have 2, 3, 4, or 5 channel segments each carrying particles (e.g., biological particles, cell beads, and/or gel beads) that meet at a channel junction. Fluid may be directed to flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

The generated droplets may comprise two subsets of droplets: (1) occupied droplets 118, containing one or more biological particles 114, and (2) unoccupied droplets 120, not containing any biological particles 114. Occupied droplets 118 may comprise singly occupied droplets (having one biological particle) and multiply occupied droplets (having more than one biological particle). As described elsewhere herein, in some cases, the majority of occupied partitions can include no more than one biological particle per occupied partition and some of the generated partitions can be unoccupied (of any biological particle). In some cases, though, some of the occupied partitions may include more than one biological particle. In some cases, the partitioning process may be controlled such that fewer than about 25% of the occupied partitions contain more than one biological particle, and in many cases, fewer than about 20% of the occupied partitions have more than one biological particle, while in some cases, fewer than about 10% or even fewer than about 5% of the occupied partitions include more than one biological particle per partition.

In some cases, it may be desirable to minimize the creation of excessive numbers of empty partitions, such as to reduce costs and/or increase efficiency. While this minimization may be achieved by providing a sufficient number of biological particles (e.g., biological particles 114) at the partitioning junction 110, such as to ensure that at least one biological particle is encapsulated in a partition, the Poissonian distribution may expectedly increase the number of partitions that include multiple biological particles. As such, where singly occupied partitions are to be obtained, at most about 95%, 90%, 85%, 80%, 75%, 70%, 65%, 60%, 55%, 50%, 45%, 40%, 35%, 30%, 25%, 20%, 15%, 10%, 5% or less of the generated partitions can be unoccupied.

In some cases, the flow of one or more of the biological particles (e.g., in channel segment 102), or other fluids directed into the partitioning junction (e.g., in channel segments 104, 106) can be controlled such that, in many cases, no more than about 50% of the generated partitions, no more than about 25% of the generated partitions, or no more than about 10% of the generated partitions are unoccupied. These flows can be controlled so as to present a non-Poissonian distribution of single-occupied partitions while providing lower levels of unoccupied partitions. The above noted ranges of unoccupied partitions can be achieved while still providing any of the single occupancy rates described above. For example, in many cases, the use of the systems and methods described herein can create resulting partitions that have multiple occupancy rates of less than about 25%, less than about 20%, less than about 15%, less than about 10%, and in many cases, less than about 5%, while having unoccupied partitions of less than about 50%, less than about 40%, less than about 30%, less than about 20%, less than about 10%, less than about 5%, or less.

Figure 2:
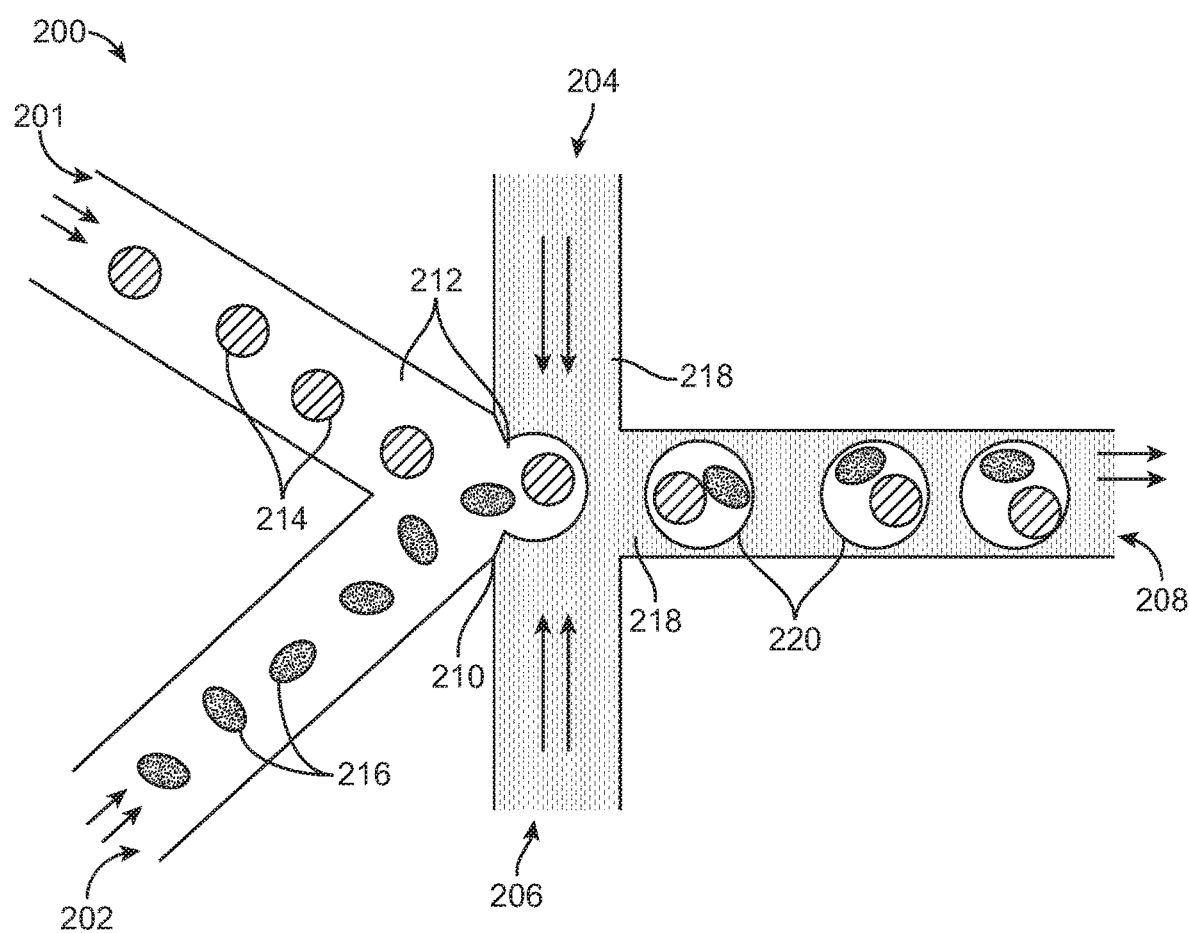
FIG. 2 shows an example of a microfluidic channel structure for delivering barcode carrying beads to droplets.

As will be appreciated, the above-described occupancy rates are also applicable to partitions that include both biological particles and additional reagents, including, but not limited to, microcapsules or beads (e.g., gel beads) carrying barcoded nucleic acid molecules (e.g., oligonucleotides) (described in relation to FIG. 2). The occupied partitions (e.g., at least about 10%, 20%, 30%, 40%, 50%, 60%, 70%, 80%, 90%, 95%, or 99% of the occupied partitions) can include both a microcapsule (e.g., bead) comprising barcoded nucleic acid molecules and a biological particle.

In another aspect, in addition to or as an alternative to droplet based partitioning, biological particles may be encapsulated within a microcapsule that comprises an outer shell, layer or porous matrix in which is entrained one or more individual biological particles or small groups of biological particles. The microcapsule may include other reagents. Encapsulation of biological particles may be performed by a variety of processes. Such processes may combine an aqueous fluid containing the biological particles with a polymeric precursor material that may be capable of being formed into a gel or other solid or semi-solid matrix upon application of a particular stimulus to the polymer precursor. Such stimuli can include, for example, thermal stimuli (e.g., either heating or cooling), photo-stimuli (e.g., through photo-curing), chemical stimuli (e.g., through cross-linking, polymerization initiation of the precursor (e.g., through added initiators)), mechanical stimuli, or a combination thereof.

Preparation of microcapsules comprising biological particles may be performed by a variety of methods. For example, air knife droplet or aerosol generators may be used to dispense droplets of precursor fluids into gelling solutions in order to form microcapsules that include individual biological particles or small groups of biological particles. Likewise, membrane based encapsulation systems may be used to generate microcapsules comprising encapsulated biological particles as described herein. Microfluidic systems of the present disclosure, such as that shown in FIG. 1, may be readily used in encapsulating cells as described herein. In particular, and with reference to FIG. 1, the aqueous fluid 112 comprising (i) the biological particles 114 and (ii) the polymer precursor material (not shown) is flowed into channel junction 110, where it is partitioned into droplets 118, 120 through the flow of non-aqueous fluid 116. In the case of encapsulation methods, non-aqueous fluid 116 may also include an initiator (not shown) to cause polymerization and/or crosslinking of the polymer precursor to form the microcapsule that includes the entrained biological particles. Examples of polymer precursor/initiator pairs include those described in U.S. Patent Application Publication No. 2014/0378345, which is entirely incorporated herein by reference for all purposes.

For example, in the case where the polymer precursor material comprises a linear polymer material, such as a linear polyacrylamide, PEG, or other linear polymeric material, the activation agent may comprise a cross-linking agent, or a chemical that activates a cross-linking agent within the formed droplets. Likewise, for polymer precursors that comprise polymerizable monomers, the activation agent may comprise a polymerization initiator. For example, in certain cases, where the polymer precursor comprises a mixture of acrylamide monomer with a N,N'-bis-(acryloyl) cystamine (BAC) comonomer, an agent such as tetraethylmethylenediamine (TEMED) may be provided within the second fluid streams 116 in channel segments 104 and 106, which can initiate the copolymerization of the acrylamide and BAC into a cross-linked polymer network, or hydrogel.

Upon contact of the second fluid stream 116 with the first fluid stream 112 at junction 110, during formation of droplets, the TEMED may diffuse from the second fluid 116 into the aqueous fluid 112 comprising the linear polyacrylamide, which will activate the crosslinking of the polyacrylamide within the droplets 118, 120, resulting in the formation of gel (e.g., hydrogel) microcapsules, as solid or semi-solid beads or particles entraining the cells 114. Although described in terms of polyacrylamide encapsulation, other 'activatable' encapsulation compositions may also be employed in the context of the methods and compositions described herein. For example, formation of alginate droplets followed by exposure to divalent metal ions (e.g., $Ca^{2+}$ ions), can be used as an encapsulation process using the described processes. Likewise, agarose droplets may also be transformed into capsules through temperature based gelling (e.g., upon cooling, etc.).

In some cases, encapsulated biological particles can be selectively releasable from the microcapsule, such as through passage of time or upon application of a particular stimulus, that degrades the microcapsule sufficiently to allow the biological particles (e.g., cell), or its other contents to be released from the microcapsule, such as into a partition (e.g., droplet). For example, in the case of the polyacrylamide polymer described above, degradation of the microcapsule may be accomplished through the introduction of an appropriate reducing agent, such as DTT or the like, to cleave disulfide bonds that cross-link the polymer matrix. See, for example, U.S. Patent Application Publication No. 2014/0378345, which is entirely incorporated herein by reference for all purposes.

The biological particle can be subjected to other conditions sufficient to polymerize or gel the precursors. The conditions sufficient to polymerize or gel the precursors may comprise exposure to heating, cooling, electromagnetic radiation, and/or light. The conditions sufficient to polymerize or gel the precursors may comprise any conditions sufficient to polymerize or gel the precursors. Following polymerization or gelling, a polymer or gel may be formed around the biological particle. The polymer or gel may be diffusively permeable to chemical or biochemical reagents. The polymer or gel may be diffusively impermeable to macromolecular constituents of the biological particle. In this manner, the polymer or gel may act to allow the biological particle to be subjected to chemical or biochemical operations while spatially confining the macromolecular constituents to a region of the droplet defined by the polymer or gel. The polymer or gel may include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel may comprise any other polymer or gel.

The polymer or gel may be functionalized to bind to targeted analytes, such as nucleic acids, proteins, carbohydrates, lipids or other analytes. The polymer or gel may be polymerized or gelled via a passive mechanism. The polymer or gel may be stable in alkaline conditions or at elevated temperature. The polymer or gel may have mechanical properties similar to the mechanical properties of the bead. For instance, the polymer or gel may be of a similar size to the bead. The polymer or gel may have a mechanical strength (e.g. tensile strength) similar to that of the bead. The polymer or gel may be of a lower density than an oil. The polymer or gel may be of a density that is roughly similar to that of a buffer. The polymer or gel may have a tunable pore size. The pore size may be chosen to, for instance, retain denatured nucleic acids. The pore size may be chosen to maintain diffusive permeability to exogenous chemicals such as sodium hydroxide (NaOH) and/or endogenous chemicals such as inhibitors. The polymer or gel may be biocompatible. The polymer or gel may maintain or enhance cell viability. The polymer or gel may be biochemically compatible. The polymer or gel may be polymerized and/or depolymerized thermally, chemically, enzymatically, and/or optically.

The polymer may comprise poly(acrylamide-co-acrylic acid) crosslinked with disulfide linkages. The preparation of the polymer may comprise a two-step reaction. In the first activation step, poly(acrylamide-co-acrylic acid) may be exposed to an acylating agent to convert carboxylic acids to esters. For instance, the poly(acrylamide-co-acrylic acid) may be exposed to 4-(4,6-dimethoxy-1,3,5-triazin-2-yl)-4-methylmorpholinium chloride (DMTMM). The polyacrylamide-co-acrylic acid may be exposed to other salts of 4-(4,6-dimethoxy-1,3,5-triazin-2-yl)-4-methylmorpholinium. In the second cross-linking step, the ester formed in the first step may be exposed to a disulfide crosslinking agent. For instance, the ester may be exposed to cystamine (2,2'-dithiobis(ethylamine)). Following the two steps, the biological particle may be surrounded by polyacrylamide strands linked together by disulfide bridges. In this manner, the biological particle may be encased inside of or comprise a gel or matrix (e.g., polymer matrix) to form a "cell bead." A cell bead can contain biological particles (e.g., a cell) or macromolecular constituents (e.g., RNA, DNA, proteins, etc.) of biological particles. A cell bead may include a single cell or multiple cells, or a derivative of the single cell or multiple cells. For example after lysing and washing the cells, inhibitory components from cell lysates can be washed away and the macromolecular constituents can be bound as cell beads. Systems and methods disclosed herein can be applicable to both cell beads (and/or droplets or other partitions) containing biological particles and cell beads (and/or droplets or other partitions) containing macromolecular constituents of biological particles.

Encapsulated biological particles can provide certain potential advantages of being more storable and more portable than droplet-based partitioned biological particles. Furthermore, in some cases, it may be desirable to allow biological particles to incubate for a select period of time before analysis, such as in order to characterize changes in such biological particles over time, either in the presence or absence of different stimuli. In such cases, encapsulation may allow for longer incubation than partitioning in emulsion droplets, although in some cases, droplet partitioned biological particles may also be incubated for different periods of time, e.g., at least 10 seconds, at least 30 seconds, at least 1 minute, at least 5 minutes, at least 10 minutes, at least 30 minutes, at least 1 hour, at least 2 hours, at least 5 hours, or at least 10 hours or more. The encapsulation of biological particles may constitute the partitioning of the biological particles into which other reagents are co-partitioned. Alternatively or in addition, encapsulated biological particles may be readily deposited into other partitions (e.g., droplets) as described above.

Beads

A partition may comprise one or more unique identifiers, such as barcodes. Barcodes may be previously, subsequently or concurrently delivered to the partitions that hold the compartmentalized or partitioned biological particle. For example, barcodes may be injected into droplets previous to, subsequent to, or concurrently with droplet generation. The delivery of the barcodes to a particular partition allows for the later attribution of the characteristics of the individual biological particle to the particular partition. Barcodes may be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can comprise a bead. Beads are described in further detail below.

In some cases, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus may disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

FIG. 2 shows an example of a microfluidic channel structure 200 for delivering barcode carrying beads to droplets. The channel structure 200 can include channel segments 201, 202, 204, 206 and 208 communicating at a channel junction 210. In operation, the channel segment 201 may transport an aqueous fluid 212 that includes a plurality of beads 214 (e.g., with nucleic acid molecules, oligonucleotides, molecular tags) along the channel segment 201 into junction 210. The plurality of beads 214 may be sourced from a suspension of beads. For example, the channel segment 201 may be connected to a reservoir comprising an aqueous suspension of beads 214. The channel segment 202 may transport the aqueous fluid 212 that includes a plurality of biological particles 216 along the channel segment 202 into junction 210. The plurality of biological particles 216 may be sourced from a suspension of biological particles. For example, the channel segment 202 may be connected to a reservoir comprising an aqueous suspension of biological particles 216. In some instances, the aqueous fluid 212 in either the first channel segment 201 or the second channel segment 202, or in both segments, can include one or more reagents, as further described below. A second fluid 218 that is immiscible with the aqueous fluid 212 (e.g., oil) can be delivered to the junction 210 from each of channel segments 204 and 206. Upon meeting of the aqueous fluid 212 from each of channel segments 201 and 202 and the second fluid 218 from each of channel segments 204 and 206 at the channel junction 210, the aqueous fluid 212 can be partitioned as discrete droplets 220 in the second fluid 218 and flow away from the junction 210 along channel segment 208. The channel segment 208 may deliver the discrete droplets to an outlet reservoir fluidly coupled to the channel segment 208, where they may be harvested.

As an alternative, the channel segments 201 and 202 may meet at another junction upstream of the junction 210. At such junction, beads and biological particles may form a mixture that is directed along another channel to the junction 210 to yield droplets 220. The mixture may provide the beads and biological particles in an alternating fashion, such that, for example, a droplet comprises a single bead and a single biological particle.

Beads, biological particles and droplets may flow along channels at substantially regular flow profiles (e.g., at regular flow rates). Such regular flow profiles may permit a droplet to include a single bead and a single biological particle. Such regular flow profiles may permit the droplets to have an occupancy (e.g., droplets having beads and biological particles) greater than 5%, 10%, 20%, 30%, 40%, 50%, 60%, 70%, 80%, 90%, or 95%. Such regular flow profiles and devices that may be used to provide such regular flow profiles are provided in, for example, U.S. Patent Publication No. 2015/0292988, which is entirely incorporated herein by reference.

The second fluid 218 can comprise an oil, such as a fluorinated oil, that includes a fluorosurfactant for stabilizing the resulting droplets, for example, inhibiting subsequent coalescence of the resulting droplets 220.

A discrete droplet that is generated may include an individual biological particle 216. A discrete droplet that is generated may include a barcode or other reagent carrying bead 214. A discrete droplet generated may include both an individual biological particle and a barcode carrying bead, such as droplets 220. In some instances, a discrete droplet may include more than one individual biological particle or no biological particle. In some instances, a discrete droplet may include more than one bead or no bead. A discrete droplet may be unoccupied (e.g., no beads, no biological particles).

Beneficially, a discrete droplet partitioning a biological particle and a barcode carrying bead may effectively allow the attribution of the barcode to macromolecular constituents of the biological particle within the partition. The contents of a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 200 may have other geometries. For example, a microfluidic channel structure can have more than one channel junctions. For example, a microfluidic channel structure can have 2, 3, 4, or 5 channel segments each carrying beads that meet at a channel junction. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

A bead may be porous, non-porous, solid, semi-solid, semi-fluidic, fluidic, and/or a combination thereof. In some instances, a bead may be dissolvable, disruptable, and/or degradable. In some cases, a bead may not be degradable. In some cases, the bead may be a gel bead. A gel bead may be a hydrogel bead. A gel bead may be formed from molecular precursors, such as a polymeric or monomeric species. A semi-solid bead may be a liposomal bead. Solid beads may comprise metals including iron oxide, gold, and silver. In some cases, the bead may be a silica bead. In some cases, the bead can be rigid. In other cases, the bead may be flexible and/or compressible.

A bead may be of any suitable shape. Examples of bead shapes include, but are not limited to, spherical, non-spherical, oval, oblong, amorphous, circular, cylindrical, and variations thereof.

Beads may be of uniform size or heterogeneous size. In some cases, the diameter of a bead may be at least about 10 nanometers (nm), 100 nm, 500 nm, 1 micrometer (µm), 5 µm, 10 µm, 20 µm, 30 µm, 40 µm, 50 µm, 60 µm, 70 µm, 80 µm, 90 µm, 100 µm, 250 µm, 500 µm, 1 mm, or greater. In some cases, a bead may have a diameter of less than about 10 nm, 100 nm, 500 nm, 1 µm, 5 µm, 10 µm, 20 µm, 30 µm, 40 µm, 50 µm, 60 µm, 70 µm, 80 µm, 90 µm, 100 µm, 250 µm, 500 µm, 1 mm, or less. In some cases, a bead may have a diameter in the range of about 40-75 µm, 30-75 µm, 20-75 µm, 40-85 µm, 40-95 µm, 20-100 µm, 10-100 µm, 1-100 µm, 20-250 µm, or 20-500 µm.

In certain aspects, beads can be provided as a population or plurality of beads having a relatively monodisperse size distribution. Where it may be desirable to provide relatively consistent amounts of reagents within partitions, maintaining relatively consistent bead characteristics, such as size, can contribute to the overall consistency. In particular, the beads described herein may have size distributions that have a coefficient of variation in their cross-sectional dimensions of less than 50%, less than 40%, less than 30%, less than 20%, and in some cases less than 15%, less than 10%, less than 5%, or less.

A bead may comprise natural and/or synthetic materials. For example, a bead can comprise a natural polymer, a synthetic polymer or both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

In some instances, the bead may contain molecular precursors (e.g., monomers or polymers), which may form a polymer network via polymerization of the molecular precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers. In some cases, the bead may comprise covalent or ionic bonds between polymeric precursors (e.g., monomers, oligomers, linear polymers), nucleic acid molecules (e.g., oligonucleotides), primers, and other entities. In some cases, the covalent bonds can be carbon-carbon bonds, thioether bonds, or carbon-heteroatom bonds.

Cross-linking may be permanent or reversible, depending upon the particular cross-linker used. Reversible cross-linking may allow for the polymer to linearize or dissociate under appropriate conditions. In some cases, reversible cross-linking may also allow for reversible attachment of a material bound to the surface of a bead. In some cases, a cross-linker may form disulfide linkages. In some cases, the chemical cross-linker forming disulfide linkages may be cystamine or a modified cystamine.

In some cases, disulfide linkages can be formed between molecular precursor units (e.g., monomers, oligomers, or linear polymers) or precursors incorporated into a bead and nucleic acid molecules (e.g., oligonucleotides). Cystamine (including modified cystamines), for example, is an organic agent comprising a disulfide bond that may be used as a crosslinker agent between individual monomeric or polymeric precursors of a bead. Polyacrylamide may be polymerized in the presence of cystamine or a species comprising cystamine (e.g., a modified cystamine) to generate polyacrylamide gel beads comprising disulfide linkages (e.g., chemically degradable beads comprising chemically-reducible cross-linkers). The disulfide linkages may permit the bead to be degraded (or dissolved) upon exposure of the bead to a reducing agent.

In some cases, chitosan, a linear polysaccharide polymer, may be crosslinked with glutaraldehyde via hydrophilic chains to form a bead. Crosslinking of chitosan polymers may be achieved by chemical reactions that are initiated by heat, pressure, change in pH, and/or radiation.

In some cases, a bead may comprise an acrydite moiety, which in certain aspects may be used to attach one or more nucleic acid molecules (e.g., barcode sequence, barcoded nucleic acid molecule, barcoded oligonucleotide, primer, or other oligonucleotide) to the bead. In some cases, an acrydite moiety can refer to an acrydite analogue generated from the reaction of acrydite with one or more species, such as, the reaction of acrydite with other monomers and cross-linkers during a polymerization reaction. Acrydite moieties may be modified to form chemical bonds with a species to be attached, such as a nucleic acid molecule (e.g., barcode sequence, barcoded nucleic acid molecule, barcoded oligonucleotide, primer, or other oligonucleotide). Acrydite moieties may be modified with thiol groups capable of forming a disulfide bond or may be modified with groups already comprising a disulfide bond. The thiol or disulfide (via disulfide exchange) may be used as an anchor point for a species to be attached or another part of the acrydite moiety may be used for attachment. In some cases, attachment can be reversible, such that when the disulfide bond is broken (e.g., in the presence of a reducing agent), the attached species is released from the bead. In other cases, an acrydite moiety can comprise a reactive hydroxyl group that may be used for attachment.

Functionalization of beads for attachment of nucleic acid molecules (e.g., oligonucleotides) may be achieved through a wide range of different approaches, including activation of chemical groups within a polymer, incorporation of active or activatable functional groups in the polymer structure, or attachment at the pre-polymer or monomer stage in bead production.

For example, precursors (e.g., monomers, cross-linkers) that are polymerized to form a bead may comprise acrydite moieties, such that when a bead is generated, the bead also comprises acrydite moieties. The acrydite moieties can be attached to a nucleic acid molecule (e.g., oligonucleotide), which may include a priming sequence (e.g., a primer for amplifying target nucleic acids, random primer, primer sequence for messenger RNA) and/or one or more barcode sequences. The one more barcode sequences may include sequences that are the same for all nucleic acid molecules coupled to a given bead and/or sequences that are different across all nucleic acid molecules coupled to the given bead. The nucleic acid molecule may be incorporated into the bead.

In some cases, the nucleic acid molecule can comprise a functional sequence, for example, for attachment to a sequencing flow cell, such as, for example, a P5 sequence for Illumina® sequencing. In some cases, the nucleic acid molecule or derivative thereof (e.g., oligonucleotide or polynucleotide generated from the nucleic acid molecule) can comprise another functional sequence, such as, for example, a P7 sequence for attachment to a sequencing flow cell for Illumina sequencing. In some cases, the nucleic acid molecule can comprise a barcode sequence. In some cases, the primer can further comprise a unique molecular identifier (UMI). In some cases, the primer can comprise an R1 primer sequence for Illumina sequencing. In some cases, the primer can comprise an R2 primer sequence for Illumina sequencing. Examples of such nucleic acid molecules (e.g., oligonucleotides, polynucleotides, etc.) and uses thereof, as may be used with compositions, devices, methods and systems of the present disclosure, are provided in U.S. Patent Pub. Nos. 2014/0378345 and 2015/0376609, each of which is entirely incorporated herein by reference.

Figure 8:
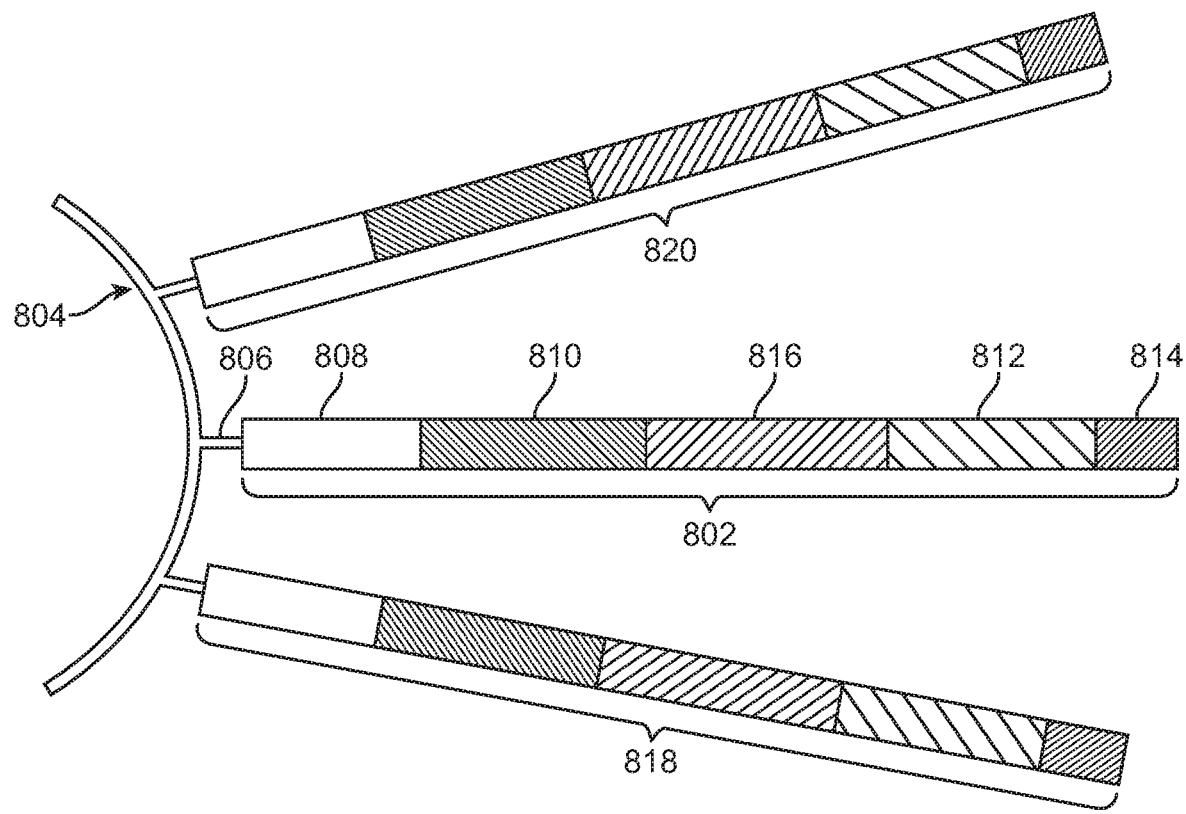
FIG. 8 illustrates an example of a barcode carrying bead.

FIG. 8 illustrates an example of a barcode carrying bead. A nucleic acid molecule 802, such as an oligonucleotide, can be coupled to a bead 804 by a releasable linkage 806, such as, for example, a disulfide linker. The same bead 804 may be coupled (e.g., via releasable linkage) to one or more other nucleic acid molecules 818, 820. The nucleic acid molecule 802 may be or comprise a barcode. As noted elsewhere herein, the structure of the barcode may comprise a number of sequence elements. The nucleic acid molecule 802 may comprise a functional sequence 808 that may be used in subsequent processing. For example, the functional sequence 808 may include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule 802 may comprise a barcode sequence 810 for use in barcoding the sample (e.g., DNA, RNA, protein, etc.). In some cases, the barcode sequence 810 can be bead-specific such that the barcode sequence 810 is common to all nucleic acid molecules (e.g., including nucleic acid molecule 802) coupled to the same bead 804. Alternatively or in addition, the barcode sequence 810 can be partition-specific such that the barcode sequence 810 is common to all nucleic acid molecules coupled to one or more beads that are partitioned into the same partition. The nucleic acid molecule 802 may comprise a specific priming sequence 812, such as an mRNA specific priming sequence (e.g., poly-T sequence), a targeted priming sequence, and/or a random priming sequence. The nucleic acid molecule 802 may comprise an anchoring sequence 814 to ensure that the specific priming sequence 812 hybridizes at the sequence end (e.g., of the mRNA). For example, the anchoring sequence 814 can include a random short sequence of nucleotides, such as a 1-mer, 2-mer, 3-mer or longer sequence, which can ensure that a poly-T segment is more likely to hybridize at the sequence end of the poly-A tail of the mRNA.

The nucleic acid molecule 802 may comprise a unique molecular identifying sequence 816 (e.g., unique molecular identifier (UMI)). In some cases, the unique molecular identifying sequence 816 may comprise from about 5 to about 8 nucleotides. Alternatively, the unique molecular identifying sequence 816 may compress less than about 5 or more than about 8 nucleotides. The unique molecular identifying sequence 816 may be a unique sequence that varies across individual nucleic acid molecules (e.g., 802, 818, 820, etc.) coupled to a single bead (e.g., bead 804). In some cases, the unique molecular identifying sequence 816 may be a random sequence (e.g., such as a random N-mer sequence). For example, the UMI may provide a unique identifier of the starting mRNA molecule that was captured, in order to allow quantitation of the number of original expressed RNA. As will be appreciated, although FIG. 8 shows three nucleic acid molecules 802, 818, 820 coupled to the surface of the bead 804, an individual bead may be coupled to any number of individual nucleic acid molecules, for example, from one to tens to hundreds of thousands or even millions of individual nucleic acid molecules. The respective barcodes for the individual nucleic acid molecules can comprise both common sequence segments or relatively common sequence segments (e.g., 808, 810, 812, etc.) and variable or unique sequence segments (e.g., 816) between different individual nucleic acid molecules coupled to the same bead.

In operation, a biological particle (e.g., cell, DNA, RNA, etc.) can be co-partitioned along with a barcode bearing bead 804. The barcoded nucleic acid molecules 802, 818, 820 can be released from the bead 804 in the partition. By way of example, in the context of analyzing sample RNA, the poly-T segment (e.g., 812) of one of the released nucleic acid molecules (e.g., 802) can hybridize to the poly-A tail of a mRNA molecule. Reverse transcription may result in a cDNA transcript of the mRNA, but which transcript includes each of the sequence segments 808, 810, 816 of the nucleic acid molecule 802. Because the nucleic acid molecule 802 comprises an anchoring sequence 814, it will more likely hybridize to and prime reverse transcription at the sequence end of the poly-A tail of the mRNA. Within any given partition, all of the cDNA transcripts of the individual mRNA molecules may include a common barcode sequence segment 810. However, the transcripts made from the different mRNA molecules within a given partition may vary at the unique molecular identifying sequence 812 segment (e.g., UMI segment). Beneficially, even following any subsequent amplification of the contents of a given partition, the number of different UMIs can be indicative of the quantity of mRNA originating from a given partition, and thus from the biological particle (e.g., cell). As noted above, the transcripts can be amplified, cleaned up and sequenced to identify the sequence of the cDNA transcript of the mRNA, as well as to sequence the barcode segment and the UMI segment. While a poly-T primer sequence is described, other targeted or random priming sequences may also be used in priming the reverse transcription reaction. Likewise, although described as releasing the barcoded oligonucleotides into the partition, in some cases, the nucleic acid molecules bound to the bead (e.g., gel bead) may be used to hybridize and capture the mRNA on the solid phase of the bead, for example, in order to facilitate the separation of the RNA from other cell contents.

In some cases, precursors comprising a functional group that is reactive or capable of being activated such that it becomes reactive can be polymerized with other precursors to generate gel beads comprising the activated or activatable functional group. The functional group may then be used to attach additional species (e.g., disulfide linkers, primers, other oligonucleotides, etc.) to the gel beads. For example, some precursors comprising a carboxylic acid (COOH) group can co-polymerize with other precursors to form a gel bead that also comprises a COOH functional group. In some cases, acrylic acid (a species comprising free COOH groups), acrylamide, and bis(acryloyl)cystamine can be co-polymerized together to generate a gel bead comprising free COOH groups. The COOH groups of the gel bead can be activated (e.g., via 1-Ethyl-3-(3-dimethylaminopropyl)car-bodiimide (EDC) and N-Hydroxysuccinimide (NHS) or 4-(4,6-Dimethoxy-1,3,5-triazin-2-yl)-4-methylmorpho-linium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

Beads comprising disulfide linkages in their polymeric network may be functionalized with additional species via reduction of some of the disulfide linkages to free thiols. The disulfide linkages may be reduced via, for example, the action of a reducing agent (e.g., DTT, TCEP, etc.) to generate free thiol groups, without dissolution of the bead. Free thiols of the beads can then react with free thiols of a species or a species comprising another disulfide bond (e.g., via thiol-disulfide exchange) such that the species can be linked to the beads (e.g., via a generated disulfide bond). In some cases, free thiols of the beads may react with any other suitable group. For example, free thiols of the beads may react with species comprising an acrydite moiety. The free thiol groups of the beads can react with the acrydite via Michael addition chemistry, such that the species comprising the acrydite is linked to the bead. In some cases, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control may be exerted, for example, by controlling the concentration of a reducing agent used to generate free thiol groups and/or concentration of reagents used to form disulfide bonds in bead polymerization. In some cases, a low concentration (e.g., molecules of reducing agent:gel bead ratios of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, less than or equal to about 1:10,000) of reducing agent may be used for reduction. Controlling the number of disulfide linkages that are reduced to free thiols may be useful in ensuring bead structural integrity during functionalization. In some cases, optically-active agents, such as fluorescent dyes may be coupled to beads via free thiol groups of the beads and used to quantify the number of free thiols present in a bead and/or track a bead.

In some cases, addition of moieties to a gel bead after gel bead formation may be advantageous. For example, addition of an oligonucleotide (e.g., barcoded oligonucleotide) after gel bead formation may avoid loss of the species during chain transfer termination that can occur during polymerization. Moreover, smaller precursors (e.g., monomers or cross linkers that do not comprise side chain groups and linked moieties) may be used for polymerization and can be minimally hindered from growing chain ends due to viscous effects. In some cases, functionalization after gel bead synthesis can minimize exposure of species (e.g., oligonucleotides) to be loaded with potentially damaging agents (e.g., free radicals) and/or chemical environments. In some cases, the generated gel may possess an upper critical solution temperature (UCST) that can permit temperature driven swelling and collapse of a bead. Such functionality may aid in oligonucleotide (e.g., a primer) infiltration into the bead during subsequent functionalization of the bead with the oligonucleotide. Post-production functionalization may also be useful in controlling loading ratios of species in beads, such that, for example, the variability in loading ratio is minimized. Species loading may also be performed in a batch process such that a plurality of beads can be functionalized with the species in a single batch.

A bead injected or otherwise introduced into a partition may comprise releasably, cleavably, or reversibly attached barcodes. A bead injected or otherwise introduced into a partition may comprise activatable barcodes. A bead injected or otherwise introduced into a partition may be degradable, disruptable, or dissolvable beads.

Barcodes can be releasably, cleavably or reversibly attached to the beads such that barcodes can be released or be releasable through cleavage of a linkage between the barcode molecule and the bead, or released through degradation of the underlying bead itself, allowing the barcodes to be accessed or be accessible by other reagents, or both. In non-limiting examples, cleavage may be achieved through reduction of di-sulfide bonds, use of restriction enzymes, photo-activated cleavage, or cleavage via other types of stimuli (e.g., chemical, thermal, pH, enzymatic, etc.) and/or reactions, such as described elsewhere herein. Releasable barcodes may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to, or as an alternative to the cleavable linkages between the beads and the associated molecules, such as barcode containing nucleic acid molecules (e.g., barcoded oligonucleotides), the beads may be degradable, disruptable, or dissolvable spontaneously or upon exposure to one or more stimuli (e.g., temperature changes, pH changes, exposure to particular chemical species or phase, exposure to light, reducing agent, etc.). In some cases, a bead may be dissolvable, such that material components of the beads are solubilized when exposed to a particular chemical species or an environmental change, such as a change temperature or a change in pH. In some cases, a gel bead can be degraded or dissolved at elevated temperature and/or in basic conditions. In some cases, a bead may be thermally degradable such that when the bead is exposed to an appropriate change in temperature (e.g., heat), the bead degrades. Degradation or dissolution of a bead bound to a species (e.g., a nucleic acid molecule, e.g., barcoded oligonucleotide) may result in release of the species from the bead.

As will be appreciated from the above disclosure, the degradation of a bead may refer to the disassociation of a bound or entrained species from a bead, both with and without structurally degrading the physical bead itself. For example, the degradation of the bead may involve cleavage of a cleavable linkage via one or more species and/or methods described elsewhere herein. In another example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

A degradable bead may be introduced into a partition, such as a droplet of an emulsion or a well, such that the bead degrades within the partition and any associated species (e.g., oligonucleotides) are released within the droplet when the appropriate stimulus is applied. The free species (e.g., oligonucleotides, nucleic acid molecules) may interact with other reagents contained in the partition. For example, a polyacrylamide bead comprising cystamine and linked, via a disulfide bond, to a barcode sequence, may be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet comprising a bead-bound barcode sequence in basic solution may also result in bead degradation and release of the attached barcode sequence into the aqueous, inner environment of the droplet.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

In some cases, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. The swelling of the beads may be accomplished, for instance, by placing the beads in a thermodynamically favorable solvent, subjecting the beads to a higher or lower temperature, subjecting the beads to a higher or lower ion concentration, and/or subjecting the beads to an electric field. The swelling of the beads may be accomplished by various swelling methods. The de-swelling of the beads may be accomplished, for instance, by transferring the beads in a thermodynamically unfavorable solvent, subjecting the beads to lower or high temperatures, subjecting the beads to a lower or higher ion concentration, and/or removing an electric field. The de-swelling of the beads may be accomplished by various de-swelling methods. Transferring the beads may cause pores in the bead to shrink. The shrinking may then hinder reagents within the beads from diffusing out of the interiors of the beads. The hindrance may be due to steric interactions between the reagents and the interiors of the beads. The transfer may be accomplished microfluidically. For instance, the transfer may be achieved by moving the beads from one co-flowing solvent stream to a different co-flowing solvent stream. The swellability and/or pore size of the beads may be adjusted by changing the polymer composition of the bead.

In some cases, an acrydite moiety linked to a precursor, another species linked to a precursor, or a precursor itself can comprise a labile bond, such as chemically, thermally, or photo-sensitive bond e.g., disulfide bond, UV sensitive bond, or the like. Once acrydite moieties or other moieties comprising a labile bond are incorporated into a bead, the bead may also comprise the labile bond. The labile bond may be, for example, useful in reversibly linking (e.g., covalently linking) species (e.g., barcodes, primers, etc.) to a bead. In some cases, a thermally labile bond may include a nucleic acid hybridization based attachment, e.g., where an oligonucleotide is hybridized to a complementary sequence that is attached to the bead, such that thermal melting of the hybrid releases the oligonucleotide, e.g., a barcode containing sequence, from the bead or microcapsule.

The addition of multiple types of labile bonds to a gel bead may result in the generation of a bead capable of responding to varied stimuli. Each type of labile bond may be sensitive to an associated stimulus (e.g., chemical stimulus, light, temperature, enzymatic, etc.) such that release of species attached to a bead via each labile bond may be controlled by the application of the appropriate stimulus. Such functionality may be useful in controlled release of species from a gel bead. In some cases, another species comprising a labile bond may be linked to a gel bead after gel bead formation via, for example, an activated functional group of the gel bead as described above. As will be appreciated, barcodes that are releasably, cleavably or reversibly attached to the beads described herein include barcodes that are released or releasable through cleavage of a linkage between the barcode molecule and the bead, or that are released through degradation of the underlying bead itself, allowing the barcodes to be accessed or accessible by other reagents, or both.

The barcodes that are releasable as described herein may sometimes be referred to as being activatable, in that they are available for reaction once released. Thus, for example, an activatable barcode may be activated by releasing the barcode from a bead (or other suitable type of partition described herein). Other activatable configurations are also envisioned in the context of the described methods and systems.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond may be cleavable via other nucleic acid molecule targeting enzymes, such as restriction enzymes (e.g., restriction endonucleases), as described further below.

Species may be encapsulated in beads during bead generation (e.g., during polymerization of precursors). Such species may or may not participate in polymerization. Such species may be entered into polymerization reaction mixtures such that generated beads comprise the species upon bead formation. In some cases, such species may be added to the gel beads after formation. Such species may include, for example, nucleic acid molecules (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such species may include one or more enzymes described herein, including without limitation, polymerase, reverse transcriptase, restriction enzymes (e.g., endonuclease), transposase, ligase, proteinase K, DNAse, etc. Such species may include one or more reagents described elsewhere herein (e.g., lysis agents, inhibitors, inactivating agents, chelating agents, stimulus). Trapping of such species may be controlled by the polymer network density generated during polymerization of precursors, control of ionic charge within the gel bead (e.g., via ionic species linked to polymerized species), or by the release of other species. Encapsulated species may be released from a bead upon bead degradation and/or by application of a stimulus capable of releasing the species from the bead. Alternatively or in addition, species may be partitioned in a partition (e.g., droplet) during or subsequent to partition formation. Such species may include, without limitation, the abovementioned species that may also be encapsulated in a bead.

A degradable bead may comprise one or more species with a labile bond such that, when the bead/species is exposed to the appropriate stimuli, the bond is broken and the bead degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a bead may comprise a labile bond. Upon exposure to the appropriate conditions, the labile bond can be broken and the bead degraded. For example, upon exposure of a polyacrylamide gel bead comprising cystamine crosslinkers to a reducing agent, the disulfide bonds of the cystamine can be broken and the bead degraded.

A degradable bead may be useful in more quickly releasing an attached species (e.g., a nucleic acid molecule, a barcode sequence, a primer, etc) from the bead when the appropriate stimulus is applied to the bead as compared to a bead that does not degrade. For example, for a species bound to an inner surface of a porous bead or in the case of an encapsulated species, the species may have greater mobility and accessibility to other species in solution upon degradation of the bead. In some cases, a species may also be attached to a degradable bead via a degradable linker (e.g., disulfide linker). The degradable linker may respond to the same stimuli as the degradable bead or the two degradable species may respond to different stimuli. For example, a barcode sequence may be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above disclosure, while referred to as degradation of a bead, in many instances as noted above, that degradation may refer to the disassociation of a bound or entrained species from a bead, both with and without structurally degrading the physical bead itself. For example, entrained species may be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In other cases, osmotic shrinking of a bead may cause a bead to better retain an entrained species due to pore size contraction.

Where degradable beads are provided, it may be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads comprise reducible cross-linking groups, such as disulfide groups, it will be desirable to avoid contacting such beads with reducing agents, e.g., DTT or other disulfide cleaving reagents. In such cases, treatment to the beads described herein will, in some cases be provided free of reducing agents, such as DTT. Because reducing agents are often provided in commercial enzyme preparations, it may be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that may be used to treat the beads described herein. The terms "reducing agent free" or "DTT free" preparations can refer to a preparation having less than about 1/10th, less than about 1/50th, or even less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or even less than about 0.0001 mM DTT. In many cases, the amount of DTT can be undetectable.

Numerous chemical triggers may be used to trigger the degradation of beads. Examples of these chemical changes may include, but are not limited to pH-mediated changes to the integrity of a component within the bead, degradation of a component of a bead via cleavage of cross-linked bonds, and depolymerization of a component of a bead.

In some embodiments, a bead may be formed from materials that comprise degradable chemical crosslinkers, such as BAC or cystamine. Degradation of such degradable crosslinkers may be accomplished through a number of mechanisms. In some examples, a bead may be contacted with a chemical degrading agent that may induce oxidation, reduction or other chemical changes. For example, a chemical degrading agent may be a reducing agent, such as dithiothreitol (DTT). Additional examples of reducing agents may include β-mercaptoethanol, (2S)-2-amino-1,4-dimercaptobutane (dithiobutylamine or DTBA), tris(2-carboxyethyl) phosphine (TCEP), or combinations thereof. A reducing agent may degrade the disulfide bonds formed between gel precursors forming the bead, and thus, degrade the bead. In other cases, a change in pH of a solution, such as an increase in pH, may trigger degradation of a bead. In other cases, exposure to an aqueous solution, such as water, may trigger hydrolytic degradation, and thus degradation of the bead. In some cases, any combination of stimuli may trigger degradation of a bead. For example, a change in pH may enable a chemical agent (e.g., DTT) to become an effective reducing agent.

Beads may also be induced to release their contents upon the application of a thermal stimulus. A change in temperature can cause a variety of changes to a bead. For example, heat can cause a solid bead to liquefy. A change in heat may cause melting of a bead such that a portion of the bead degrades. In other cases, heat may increase the internal pressure of the bead components such that the bead ruptures or explodes. Heat may also act upon heat-sensitive polymers used as materials to construct beads.

Any suitable agent may degrade beads. In some embodiments, changes in temperature or pH may be used to degrade thermo-sensitive or pH-sensitive bonds within beads. In some embodiments, chemical degrading agents may be used to degrade chemical bonds within beads by oxidation, reduction or other chemical changes. For example, a chemical degrading agent may be a reducing agent, such as DTT, wherein DTT may degrade the disulfide bonds formed between a crosslinker and gel precursors, thus degrading the bead. In some embodiments, a reducing agent may be added to degrade the bead, which may or may not cause the bead to release its contents. Examples of reducing agents may include dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof. The reducing agent may be present at a concentration of about 0.1 mM, 0.5 mM, 1 mM, 5 mM, 10 mM. The reducing agent may be present at a concentration of at least about 0.1 mM, 0.5 mM, 1 mM, 5 mM, 10 mM, or greater than 10 mM. The reducing agent may be present at concentration of at most about 10 mM, 5 mM, 1 mM, 0.5 mM, 0.1 mM, or less.

Any suitable number of molecular tag molecules (e.g., primer, barcoded oligonucleotide) can be associated with a bead such that, upon release from the bead, the molecular tag molecules (e.g., primer, e.g., barcoded oligonucleotide) are present in the partition at a pre-defined concentration. Such pre-defined concentration may be selected to facilitate certain reactions for generating a sequencing library, e.g., amplification, within the partition. In some cases, the pre-defined concentration of the primer can be limited by the process of producing oligonucleotide bearing beads.

Although FIG. 1 and FIG. 2 have been described in terms of providing substantially singly occupied partitions, above, in certain cases, it may be desirable to provide multiply occupied partitions, e.g., containing two, three, four or more cells and/or microcapsules (e.g., beads) comprising barcoded nucleic acid molecules (e.g., oligonucleotides) within a single partition. Accordingly, as noted above, the flow characteristics of the biological particle and/or bead containing fluids and partitioning fluids may be controlled to provide for such multiply occupied partitions. In particular, the flow parameters may be controlled to provide a given occupancy rate at greater than about 50% of the partitions, greater than about 75%, and in some cases greater than about 80%, 90%, 95%, or higher.

In some cases, additional microcapsules can be used to deliver additional reagents to a partition. In such cases, it may be advantageous to introduce different beads into a common channel or droplet generation junction, from different bead sources (e.g., containing different associated reagents) through different channel inlets into such common channel or droplet generation junction (e.g., junction 210). In such cases, the flow and frequency of the different beads into the channel or junction may be controlled to provide for a certain ratio of microcapsules from each source, while ensuring a given pairing or combination of such beads into a partition with a given number of biological particles (e.g., one biological particle and one bead per partition).

The partitions described herein may comprise small volumes, for example, less than about 10 microliters (μL), 5 μL, 1 μL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

For example, in the case of droplet based partitions, the droplets may have overall volumes that are less than about 1000 pL, 900 pL, 800 pL, 700 pL, 600 pL, 500 pL, 400 pL, 300 pL, 200 pL, 100 pL, 50 pL, 20 pL, 10 pL, 1 pL, or less. Where co-partitioned with microcapsules, it will be appreciated that the sample fluid volume, e.g., including co-partitioned biological particles and/or beads, within the partitions may be less than about 90% of the above described volumes, less than about 80%, less than about 70%, less than about 60%, less than about 50%, less than about 40%, less than about 30%, less than about 20%, or less than about 10% of the above described volumes.

As is described elsewhere herein, partitioning species may generate a population or plurality of partitions. In such cases, any suitable number of partitions can be generated or otherwise provided. For example, at least about 1,000 partitions, at least about 5,000 partitions, at least about 10,000 partitions, at least about 50,000 partitions, at least about 100,000 partitions, at least about 500,000 partitions, at least about 1,000,000 partitions, at least about 5,000,000 partitions at least about 10,000,000 partitions, at least about 50,000,000 partitions, at least about 100,000,000 partitions, at least about 500,000,000 partitions, at least about 1,000,000,000 partitions, or more partitions can be generated or otherwise provided. Moreover, the plurality of partitions may comprise both unoccupied partitions (e.g., empty partitions) and occupied partitions.

Reagents

In accordance with certain aspects, biological particles may be partitioned along with lysis reagents in order to release the contents of the biological particles within the partition. In such cases, the lysis agents can be contacted with the biological particle suspension concurrently with, or immediately prior to, the introduction of the biological particles into the partitioning junction/droplet generation zone (e.g., junction 210), such as through an additional channel or channels upstream of the channel junction. In accordance with other aspects, additionally or alternatively, biological particles may be partitioned along with other reagents, as will be described further below.

Figure 3:
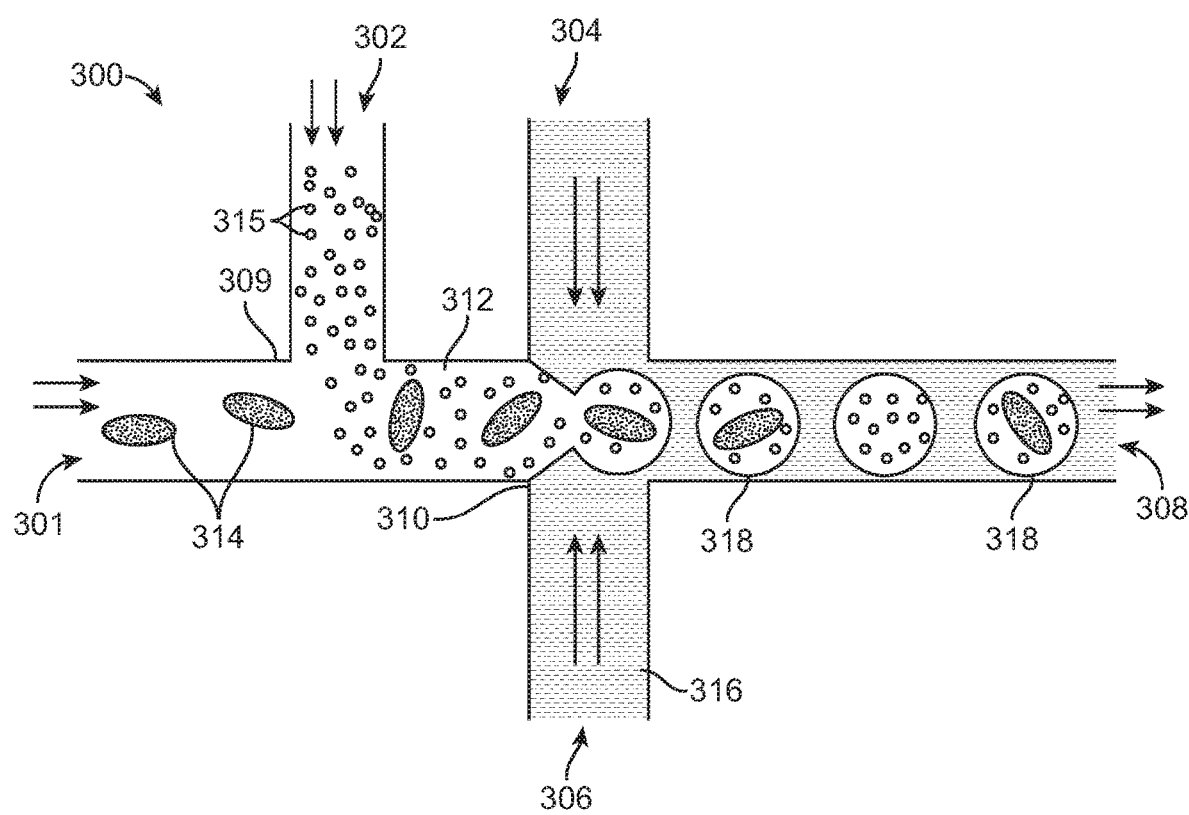
FIG. 3 shows an example of a microfluidic channel structure for co-partitioning biological particles and reagents.

FIG. 3 shows an example of a microfluidic channel structure 300 for co-partitioning biological particles and reagents. The channel structure 300 can include channel segments 301, 302, 304, 306 and 308. Channel segments 301 and 302 communicate at a first channel junction 309. Channel segments 302, 304, 306, and 308 communicate at a second channel junction 310.

In an example operation, the channel segment 301 may transport an aqueous fluid 312 that includes a plurality of biological particles 314 along the channel segment 301 into the second junction 310. As an alternative or in addition to, channel segment 301 may transport beads (e.g., gel beads). The beads may comprise barcode molecules.

For example, the channel segment 301 may be connected to a reservoir comprising an aqueous suspension of biological particles 314. Upstream of, and immediately prior to reaching, the second junction 310, the channel segment 301 may meet the channel segment 302 at the first junction 309. The channel segment 302 may transport a plurality of reagents 315 (e.g., lysis agents) suspended in the aqueous fluid 312 along the channel segment 302 into the first junction 309. For example, the channel segment 302 may be connected to a reservoir comprising the reagents 315. After the first junction 309, the aqueous fluid 312 in the channel segment 301 can carry both the biological particles 314 and the reagents 315 towards the second junction 310. In some instances, the aqueous fluid 312 in the channel segment 301 can include one or more reagents, which can be the same or different reagents as the reagents 315. A second fluid 316 that is immiscible with the aqueous fluid 312 (e.g., oil) can be delivered to the second junction 310 from each of channel segments 304 and 306. Upon meeting of the aqueous fluid 312 from the channel segment 301 and the second fluid 316 from each of channel segments 304 and 306 at the second channel junction 310, the aqueous fluid 312 can be partitioned as discrete droplets 318 in the second fluid 316 and flow away from the second junction 310 along channel segment 308. The channel segment 308 may deliver the discrete droplets 318 to an outlet reservoir fluidly coupled to the channel segment 308, where they may be harvested.

The second fluid 316 can comprise an oil, such as a fluorinated oil, that includes a fluorosurfactant for stabilizing the resulting droplets, for example, inhibiting subsequent coalescence of the resulting droplets 318.

A discrete droplet generated may include an individual biological particle 314 and/or one or more reagents 315. In some instances, a discrete droplet generated may include a barcode carrying bead (not shown), such as via other microfluidics structures described elsewhere herein. In some instances, a discrete droplet may be unoccupied (e.g., no reagents, no biological particles).

Beneficially, when lysis reagents and biological particles are co-partitioned, the lysis reagents can facilitate the release of the contents of the biological particles within the partition. The contents released in a partition may remain discrete from the contents of other partitions.

As will be appreciated, the channel segments described herein may be coupled to any of a variety of different fluid sources or receiving components, including reservoirs, tubing, manifolds, or fluidic components of other systems. As will be appreciated, the microfluidic channel structure 300 may have other geometries. For example, a microfluidic channel structure can have more than two channel junctions. For example, a microfluidic channel structure can have 2, 3, 4, 5 channel segments or more each carrying the same or different types of beads, reagents, and/or biological particles that meet at a channel junction. Fluid flow in each channel segment may be controlled to control the partitioning of the different elements into droplets. Fluid may be directed flow along one or more channels or reservoirs via one or more fluid flow units. A fluid flow unit can comprise compressors (e.g., providing positive pressure), pumps (e.g., providing negative pressure), actuators, and the like to control flow of the fluid. Fluid may also or otherwise be controlled via applied pressure differentials, centrifugal force, electrokinetic pumping, vacuum, capillary or gravity flow, or the like.

Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St Louis, Mo.), as well as other commercially available lysis enzymes. Other lysis agents may additionally or alternatively be co-partitioned with the biological particles to cause the release of the biological particles's contents into the partitions. For example, in some cases, surfactant-based lysis solutions may be used to lyse cells, although these may be less desirable for emulsion based systems where the surfactants can interfere with stable emulsions. In some cases, lysis solutions may include non-ionic surfactants such as, for example, TritonX-100 and Tween 20. In some cases, lysis solutions may include ionic surfactants such as, for example, sarcosyl and sodium dodecyl sulfate (SDS). Electroporation, thermal, acoustic or mechanical cellular disruption may also be used in certain cases, e.g., non-emulsion based partitioning such as encapsulation of biological particles that may be in addition to or in place of droplet partitioning, where any pore size of the encapsulate is sufficiently small to retain nucleic acid fragments of a given size, following cellular disruption.

Alternatively or in addition to the lysis agents co-partitioned with the biological particles described above, other reagents can also be co-partitioned with the biological particles, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles may be exposed to an appropriate stimulus to release the biological particles or their contents from a co-partitioned microcapsule. For example, in some cases, a chemical stimulus may be co-partitioned along with an encapsulated biological particle to allow for the degradation of the microcapsule and release of the cell or its contents into the larger partition. In some cases, this stimulus may be the same as the stimulus described elsewhere herein for release of nucleic acid molecules (e.g., oligonucleotides) from their respective microcapsule (e.g., bead). In alternative aspects, this may be a different and non-overlapping stimulus, in order to allow an encapsulated biological particle to be released into a partition at a different time from the release of nucleic acid molecules into the same partition.

Additional reagents may also be co-partitioned with the biological particles, such as endonucleases to fragment a biological particle's DNA, DNA polymerase enzymes and dNTPs used to amplify the biological particle's nucleic acid fragments and to attach the barcode molecular tags to the amplified fragments. Other enzymes may be co-partitioned, including without limitation, polymerase, transposase, ligase, proteinase K, DNAse, etc. Additional reagents may also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some cases, template switching can be used to increase the length of a cDNA. In some cases, template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., polyC, to the cDNA in a template independent manner. Switch oligos can include sequences complementary to the additional nucleotides, e.g., polyG. The additional nucleotides (e.g., polyC) on the cDNA can hybridize to the additional nucleotides (e.g., polyG) on the switch oligo, whereby the switch oligo can be used by the reverse transcriptase as template to further extend the cDNA. Template switching oligonucleotides may comprise a hybridization region and a template region. The hybridization region can comprise any sequence capable of hybridizing to the target. In some cases, as previously described, the hybridization region comprises a series of G bases to complement the overhanging C bases at the 3' end of a cDNA molecule. The series of G bases may comprise 1 G base, 2 G bases, 3 G bases, 4 G bases, 5 G bases or more than 5 G bases. The template sequence can comprise any sequence to be incorporated into the cDNA. In some cases, the template region comprises at least 1 (e.g., at least 2, 3, 4, 5 or more) tag sequences and/or functional sequences. Switch oligos may comprise deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), or any combination.

In some cases, the length of a switch oligo may be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides or longer.

In some cases, the length of a switch oligo may be at most about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249 or 250 nucleotides.

Once the contents of the cells are released into their respective partitions, the macromolecular components (e.g., macromolecular constituents of biological particles, such as RNA, DNA, or proteins) contained therein may be further processed within the partitions. In accordance with the methods and systems described herein, the macromolecular component contents of individual biological particles can be provided with unique identifiers such that, upon characterization of those macromolecular components they may be attributed as having been derived from the same biological particle or particles. The ability to attribute characteristics to individual biological particles or groups of biological particles is provided by the assignment of unique identifiers specifically to an individual biological particle or groups of biological particles. Unique identifiers, e.g., in the form of nucleic acid barcodes can be assigned or associated with individual biological particles or populations of biological particles, in order to tag or label the biological particle's macromolecular components (and as a result, its characteristics) with the unique identifiers. These unique identifiers can then be used to attribute the biological particle's components and characteristics to an individual biological particle or group of biological particles.

In some aspects, this is performed by co-partitioning the individual biological particle or groups of biological particles with the unique identifiers, such as described above (with reference to FIG. 2). In some aspects, the unique identifiers are provided in the form of nucleic acid molecules (e.g., oligonucleotides) that comprise nucleic acid barcode sequences that may be attached to or otherwise associated with the nucleic acid contents of individual biological particle, or to other components of the biological particle, and particularly to fragments of those nucleic acids. The nucleic acid molecules are partitioned such that as between nucleic acid molecules in a given partition, the nucleic acid barcode sequences contained therein are the same, but as between different partitions, the nucleic acid molecule can, and do have differing barcode sequences, or at least represent a large number of different barcode sequences across all of the partitions in a given analysis. In some aspects, only one nucleic acid barcode sequence can be associated with a given partition, although in some cases, two or more different barcode sequences may be present.

The nucleic acid barcode sequences can include from about 6 to about 20 or more nucleotides within the sequence of the nucleic acid molecules (e.g., oligonucleotides). The nucleic acid barcode sequences can include from about 6 to about 20, 30, 40, 50, 60, 70, 80, 90, 100 or more nucleotides. In some cases, the length of a barcode sequence may be about 6, 7, 8, 9, 10, 11, 12, 13, 14, 15, 16, 17, 18, 19, 20 nucleotides or longer. In some cases, the length of a barcode sequence may be at least about 6, 7, 8, 9, 10, 11, 12, 13, 14, 15, 16, 17, 18, 19, 20 nucleotides or longer. In some cases, the length of a barcode sequence may be at most about 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some cases, separated barcode subsequences can be from about 4 to about 16 nucleotides in length. In some cases, the barcode subsequence may be about 4, 5, 6, 7, 8, 9, 10, 11, 12, 13, 14, 15, 16 nucleotides or longer. In some cases, the barcode subsequence may be at least about 4, 5, 6, 7, 8, 9, 10, 11, 12, 13, 14, 15, 16 nucleotides or longer. In some cases, the barcode subsequence may be at most about 4, 5, 6, 7, 8, 9, 10, 11, 12, 13, 14, 15, 16 nucleotides or shorter.

The co-partitioned nucleic acid molecules can also comprise other functional sequences useful in the processing of the nucleic acids from the co-partitioned biological particles. These sequences include, e.g., targeted or random/universal amplification primer sequences for amplifying the genomic DNA from the individual biological particles within the partitions while attaching the associated barcode sequences, sequencing primers or primer recognition sites, hybridization or probing sequences, e.g., for identification of presence of the sequences or for pulling down barcoded nucleic acids, or any of a number of other potential functional sequences. Other mechanisms of co-partitioning oligonucleotides may also be employed, including, e.g., coalescence of two or more droplets, where one droplet contains oligonucleotides, or microdispensing of oligonucleotides into partitions, e.g., droplets within microfluidic systems.

In an example, microcapsules, such as beads, are provided that each include large numbers of the above described barcoded nucleic acid molecules (e.g., barcoded oligonucleotides) releasably attached to the beads, where all of the nucleic acid molecules attached to a particular bead will include the same nucleic acid barcode sequence, but where a large number of diverse barcode sequences are represented across the population of beads used. In some embodiments, hydrogel beads, e.g., comprising polyacrylamide polymer matrices, are used as a solid support and delivery vehicle for the nucleic acid molecules into the partitions, as they are capable of carrying large numbers of nucleic acid molecules, and may be configured to release those nucleic acid molecules upon exposure to a particular stimulus, as described elsewhere herein. In some cases, the population of beads provides a diverse barcode sequence library that includes at least about 1,000 different barcode sequences, at least about 5,000 different barcode sequences, at least about 10,000 different barcode sequences, at least about 50,000 different barcode sequences, at least about 100,000 different barcode sequences, at least about 1,000,000 different barcode sequences, at least about 5,000,000 different barcode sequences, or at least about 10,000,000 different barcode sequences, or more. Additionally, each bead can be provided with large numbers of nucleic acid (e.g., oligonucleotide) molecules attached. In particular, the number of molecules of nucleic acid molecules including the barcode sequence on an individual bead can be at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules, or more. Nucleic acid molecules of a given bead can include identical (or common) barcode sequences, different barcode sequences, or a combination of both. Nucleic acid molecules of a given bead can include multiple sets of nucleic acid molecules. Nucleic acid molecules of a given set can include identical barcode sequences. The identical barcode sequences can be different from barcode sequences of nucleic acid molecules of another set.

Moreover, when the population of beads is partitioned, the resulting population of partitions can also include a diverse barcode library that includes at least about 1,000 different barcode sequences, at least about 5,000 different barcode sequences, at least about 10,000 different barcode sequences, at least at least about 50,000 different barcode sequences, at least about 100,000 different barcode sequences, at least about 1,000,000 different barcode sequences, at least about 5,000,000 different barcode sequences, or at least about 10,000,000 different barcode sequences. Additionally, each partition of the population can include at least about 1,000 nucleic acid molecules, at least about 5,000 nucleic acid molecules, at least about 10,000 nucleic acid molecules, at least about 50,000 nucleic acid molecules, at least about 100,000 nucleic acid molecules, at least about 500,000 nucleic acids, at least about 1,000,000 nucleic acid molecules, at least about 5,000,000 nucleic acid molecules, at least about 10,000,000 nucleic acid molecules, at least about 50,000,000 nucleic acid molecules, at least about 100,000,000 nucleic acid molecules, at least about 250,000,000 nucleic acid molecules and in some cases at least about 1 billion nucleic acid molecules.

In some cases, it may be desirable to incorporate multiple different barcodes within a given partition, either attached to a single or multiple beads within the partition. For example, in some cases, a mixed, but known set of barcode sequences may provide greater assurance of identification in the subsequent processing, e.g., by providing a stronger address or attribution of the barcodes to a given partition, as a duplicate or independent confirmation of the output from a given partition.

The nucleic acid molecules (e.g., oligonucleotides) are releasable from the beads upon the application of a particular stimulus to the beads. In some cases, the stimulus may be a photo-stimulus, e.g., through cleavage of a photo-labile linkage that releases the nucleic acid molecules. In other cases, a thermal stimulus may be used, where elevation of the temperature of the beads environment will result in cleavage of a linkage or other release of the nucleic acid molecules form the beads. In still other cases, a chemical stimulus can be used that cleaves a linkage of the nucleic acid molecules to the beads, or otherwise results in release of the nucleic acid molecules from the beads. In one case, such compositions include the polyacrylamide matrices described above for encapsulation of biological particles, and may be degraded for release of the attached nucleic acid molecules through exposure to a reducing agent, such as DTT.

In some aspects, provided are systems and methods for controlled partitioning. Droplet size may be controlled by adjusting certain geometric features in channel architecture (e.g., microfluidics channel architecture). For example, an expansion angle, width, and/or length of a channel may be adjusted to control droplet size.

Figure 4:
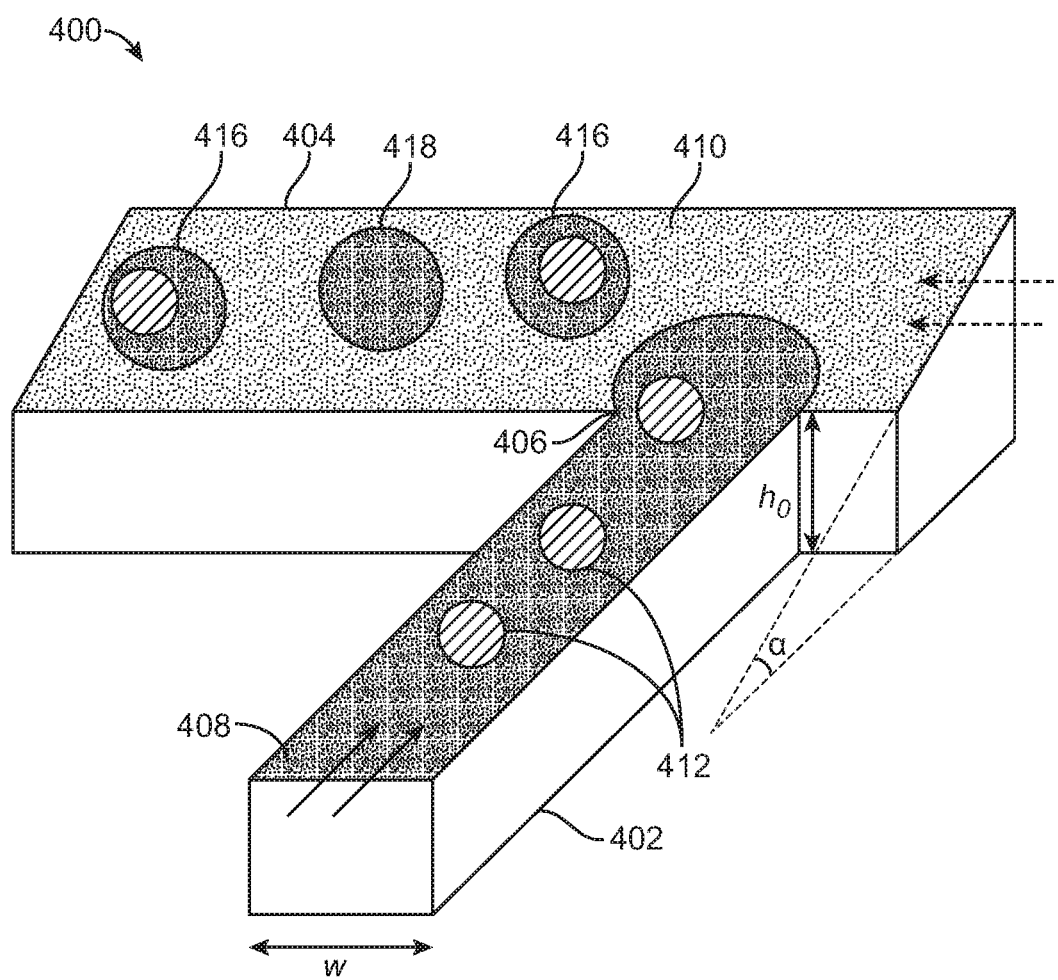
FIG. 4 shows an example of a microfluidic channel structure for the controlled partitioning of beads into discrete droplets.

FIG. 4 shows an example of a microfluidic channel structure for the controlled partitioning of beads into discrete droplets. A channel structure 400 can include a channel segment 402 communicating at a channel junction 406 (or intersection) with a reservoir 404. The reservoir 404 can be a chamber. Any reference to "reservoir," as used herein, can also refer to a "chamber." In operation, an aqueous fluid 408 that includes suspended beads 412 may be transported along the channel segment 402 into the junction 406 to meet a second fluid 410 that is immiscible with the aqueous fluid 408 in the reservoir 404 to create droplets 416, 418 of the aqueous fluid 408 flowing into the reservoir 404. At the junction 406 where the aqueous fluid 408 and the second fluid 410 meet, droplets can form based on factors such as the hydrodynamic forces at the junction 406, flow rates of the two fluids 408, 410, fluid properties, and certain geometric parameters (e.g., w, $h_0$, α, etc.) of the channel structure 400. A plurality of droplets can be collected in the reservoir 404 by continuously injecting the aqueous fluid 408 from the channel segment 402 through the junction 406.

A discrete droplet generated may include a bead (e.g., as in occupied droplets 416). Alternatively, a discrete droplet generated may include more than one bead. Alternatively, a discrete droplet generated may not include any beads (e.g., as in unoccupied droplet 418). In some instances, a discrete droplet generated may contain one or more biological particles, as described elsewhere herein. In some instances, a discrete droplet generated may comprise one or more reagents, as described elsewhere herein.

In some instances, the aqueous fluid 408 can have a substantially uniform concentration or frequency of beads 412. The beads 412 can be introduced into the channel segment 402 from a separate channel (not shown in FIG. 4). The frequency of beads 412 in the channel segment 402 may be controlled by controlling the frequency in which the beads 412 are introduced into the channel segment 402 and/or the relative flow rates of the fluids in the channel segment 402 and the separate channel. In some instances, the beads can be introduced into the channel segment 402 from a plurality of different channels, and the frequency controlled accordingly.

In some instances, the aqueous fluid 408 in the channel segment 402 can comprise biological particles (e.g., described with reference to FIGS. 1 and 2). In some instances, the aqueous fluid 408 can have a substantially uniform concentration or frequency of biological particles. As with the beads, the biological particles can be introduced into the channel segment 402 from a separate channel. The frequency or concentration of the biological particles in the aqueous fluid 408 in the channel segment 402 may be controlled by controlling the frequency in which the biological particles are introduced into the channel segment 402 and/or the relative flow rates of the fluids in the channel segment 402 and the separate channel. In some instances, the biological particles can be introduced into the channel segment 402 from a plurality of different channels, and the frequency controlled accordingly. In some instances, a first separate channel can introduce beads and a second separate channel can introduce biological particles into the channel segment 402. The first separate channel introducing the beads may be upstream or downstream of the second separate channel introducing the biological particles.

The second fluid 410 can comprise an oil, such as a fluorinated oil, that includes a fluorosurfactant for stabilizing the resulting droplets, for example, inhibiting subsequent coalescence of the resulting droplets.

In some instances, the second fluid 410 may not be subjected to and/or directed to any flow in or out of the reservoir 404. For example, the second fluid 410 may be substantially stationary in the reservoir 404. In some instances, the second fluid 410 may be subjected to flow within the reservoir 404, but not in or out of the reservoir 404, such as via application of pressure to the reservoir 404 and/or as affected by the incoming flow of the aqueous fluid 408 at the junction 406. Alternatively, the second fluid 410 may be subjected and/or directed to flow in or out of the reservoir 404. For example, the reservoir 404 can be a channel directing the second fluid 410 from upstream to downstream, transporting the generated droplets.

The channel structure 400 at or near the junction 406 may have certain geometric features that at least partly determine the sizes of the droplets formed by the channel structure 400. The channel segment 402 can have a height, $h_0$ and width, w, at or near the junction 406. By way of example, the channel segment 402 can comprise a rectangular cross-section that leads to a reservoir 404 having a wider cross-section (such as in width or diameter). Alternatively, the cross-section of the channel segment 402 can be other shapes, such as a circular shape, trapezoidal shape, polygonal shape, or any other shapes. The top and bottom walls of the reservoir 404 at or near the junction 406 can be inclined at an expansion angle, a. The expansion angle, a, allows the tongue (portion of the aqueous fluid 408 leaving channel segment 402 at junction 406 and entering the reservoir 404 before droplet formation) to increase in depth and facilitate decrease in curvature of the intermediately formed droplet. Droplet size may decrease with increasing expansion angle. The resulting droplet radius, $R_d$, may be predicted by the following equation for the aforementioned geometric parameters of $h_0$, w, and $\alpha$:

$$R_d \approx 0.44\left(1 + 2.2\sqrt{\tan\alpha}\,\frac{w}{h_0}\right)\frac{h_0}{\sqrt{\tan\alpha}}$$

By way of example, for a channel structure with w=21 μm, h=21 μm, and α=3°, the predicted droplet size is 121 μm. In another example, for a channel structure with w=25 μm, h=25 μm, and α=5°, the predicted droplet size is 123 μm. In another example, for a channel structure with w=28 μm, h=28 μm, and α=7°, the predicted droplet size is 124 μm.

In some instances, the expansion angle, a, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3° 4° 5° 6°, 7° 8°, 9° 10°, 15°, 20°, 25°, 30°, 35° 40°, 45° 50°, 55° 60°, 65°, 70°, 75° 80°, 85°, or higher. In some instances, the expansion angle can be at most about 89°, 88°, 87°, 86°, 85°, 84°, 83°, 82°, 81°, 80°, 75° 70°, 65°, 60°, 55° 50°, 45° 40°, 35° 30°, 25°, 20°, 15°, 10°, 9° 8°, 7° 6°, 5° 4° 3° 2°, 1°, 0.1°, 0.01°, or less. In some instances, the width, w, can be between a range of from about 100 micrometers (μm) to about 500 μm. In some instances, the width, w, can be between a range of from about 10 μm to about 200 μm. Alternatively, the width can be less than about 10 μm. Alternatively, the width can be greater than about 500 μm. In some instances, the flow rate of the aqueous fluid 408 entering the junction 406 can be between about 0.04 microliters (μL)/minute (min) and about 40 μL/min. In some instances, the flow rate of the aqueous fluid 408 entering the junction 406 can be between about 0.01 microliters (μL)/minute (min) and about 100 μL/min. Alternatively, the flow rate of the aqueous fluid 408 entering the junction 406 can be less than about 0.01 μL/min. Alternatively, the flow rate of the aqueous fluid 408 entering the junction 406 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 L/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 408 entering the junction 406.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

The throughput of droplet generation can be increased by increasing the points of generation, such as increasing the number of junctions (e.g., junction 406) between aqueous fluid 408 channel segments (e.g., channel segment 402) and the reservoir 404. Alternatively or in addition, the throughput of droplet generation can be increased by increasing the flow rate of the aqueous fluid 408 in the channel segment 402.

Figure 5:
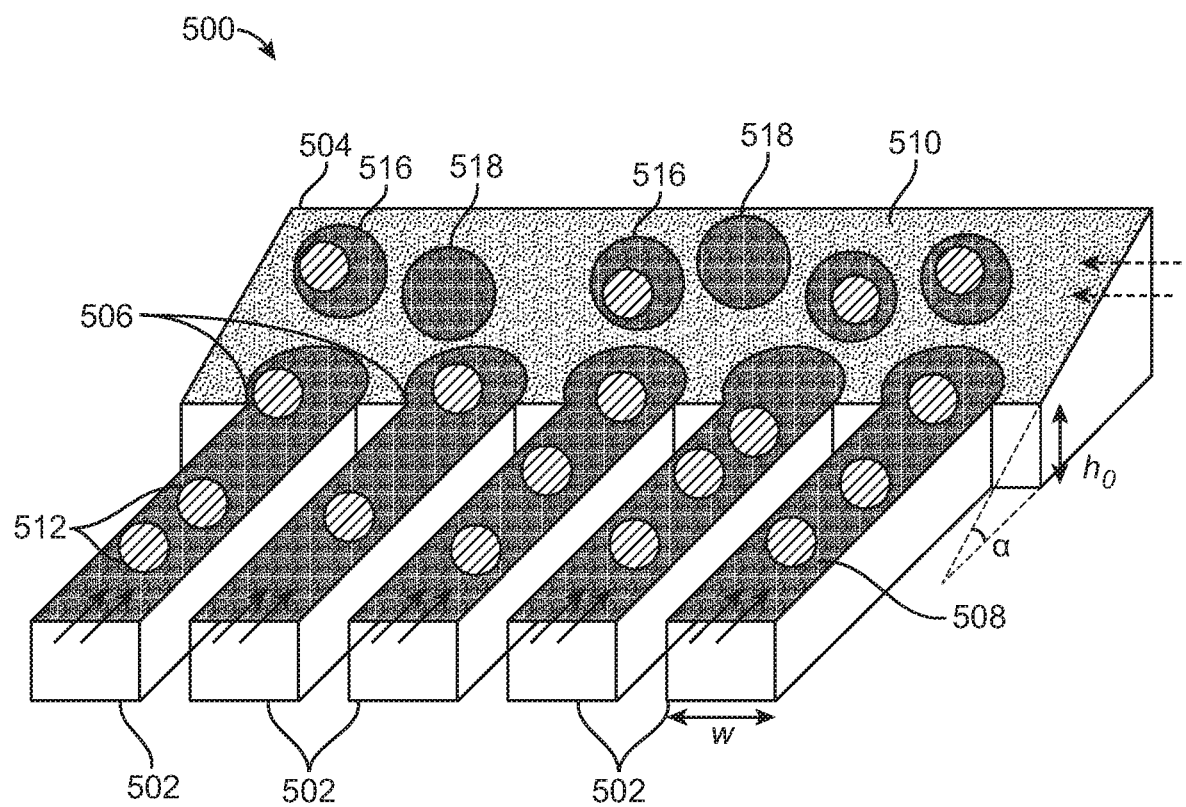
FIG. 5 shows an example of a microfluidic channel structure for increased droplet generation throughput.

FIG. 5 shows an example of a microfluidic channel structure for increased droplet generation throughput. A microfluidic channel structure 500 can comprise a plurality of channel segments 502 and a reservoir 504. Each of the plurality of channel segments 502 may be in fluid communication with the reservoir 504. The channel structure 500 can comprise a plurality of channel junctions 506 between the plurality of channel segments 502 and the reservoir 504. Each channel junction can be a point of droplet generation. The channel segment 402 from the channel structure 400 in FIG. 4 and any description to the components thereof may correspond to a given channel segment of the plurality of channel segments 502 in channel structure 500 and any description to the corresponding components thereof. The reservoir 404 from the channel structure 400 and any description to the components thereof may correspond to the reservoir 504 from the channel structure 500 and any description to the corresponding components thereof.

Each channel segment of the plurality of channel segments 502 may comprise an aqueous fluid 508 that includes suspended beads 512. The reservoir 504 may comprise a second fluid 510 that is immiscible with the aqueous fluid 508. In some instances, the second fluid 510 may not be subjected to and/or directed to any flow in or out of the reservoir 504. For example, the second fluid 510 may be substantially stationary in the reservoir 504. In some instances, the second fluid 510 may be subjected to flow within the reservoir 504, but not in or out of the reservoir 504, such as via application of pressure to the reservoir 504 and/or as affected by the incoming flow of the aqueous fluid 508 at the junctions. Alternatively, the second fluid 510 may be subjected and/or directed to flow in or out of the reservoir 504. For example, the reservoir 504 can be a channel directing the second fluid 510 from upstream to downstream, transporting the generated droplets.

In operation, the aqueous fluid 508 that includes suspended beads 512 may be transported along the plurality of channel segments 502 into the plurality of junctions 506 to meet the second fluid 510 in the reservoir 504 to create droplets 516, 518. A droplet may form from each channel segment at each corresponding junction with the reservoir 504. At the junction where the aqueous fluid 508 and the second fluid 510 meet, droplets can form based on factors such as the hydrodynamic forces at the junction, flow rates of the two fluids 508, 510, fluid properties, and certain geometric parameters (e.g., w, $h_0$, $\alpha$, etc.) of the channel structure 500, as described elsewhere herein. A plurality of droplets can be collected in the reservoir 504 by continuously injecting the aqueous fluid 508 from the plurality of channel segments 502 through the plurality of junctions 506. Throughput may significantly increase with the parallel channel configuration of channel structure 500. For example, a channel structure having five inlet channel segments comprising the aqueous fluid 508 may generate droplets five times as frequently than a channel structure having one inlet channel segment, provided that the fluid flow rate in the channel segments are substantially the same.

The fluid flow rate in the different inlet channel segments may or may not be substantially the same. A channel structure may have as many parallel channel segments as is practical and allowed for the size of the reservoir. For example, the channel structure may have at least about 2, 3, 4, 5, 6, 7, 8, 9, 10, 20, 30, 40, 50, 60, 70, 80, 90, 100, 150, 500, 250, 300, 350, 400, 450, 500, 600, 700, 800, 900, 1000, 1500, 5000 or more parallel or substantially parallel channel segments.

The geometric parameters, w, $h_o$, and α, may or may not be uniform for each of the channel segments in the plurality of channel segments 502. For example, each channel segment may have the same or different widths at or near its respective channel junction with the reservoir 504. For example, each channel segment may have the same or different height at or near its respective channel junction with the reservoir 504. In another example, the reservoir 504 may have the same or different expansion angle at the different channel junctions with the plurality of channel segments 502. When the geometric parameters are uniform, beneficially, droplet size may also be controlled to be uniform even with the increased throughput. In some instances, when it is desirable to have a different distribution of droplet sizes, the geometric parameters for the plurality of channel segments 502 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

Figure 6:
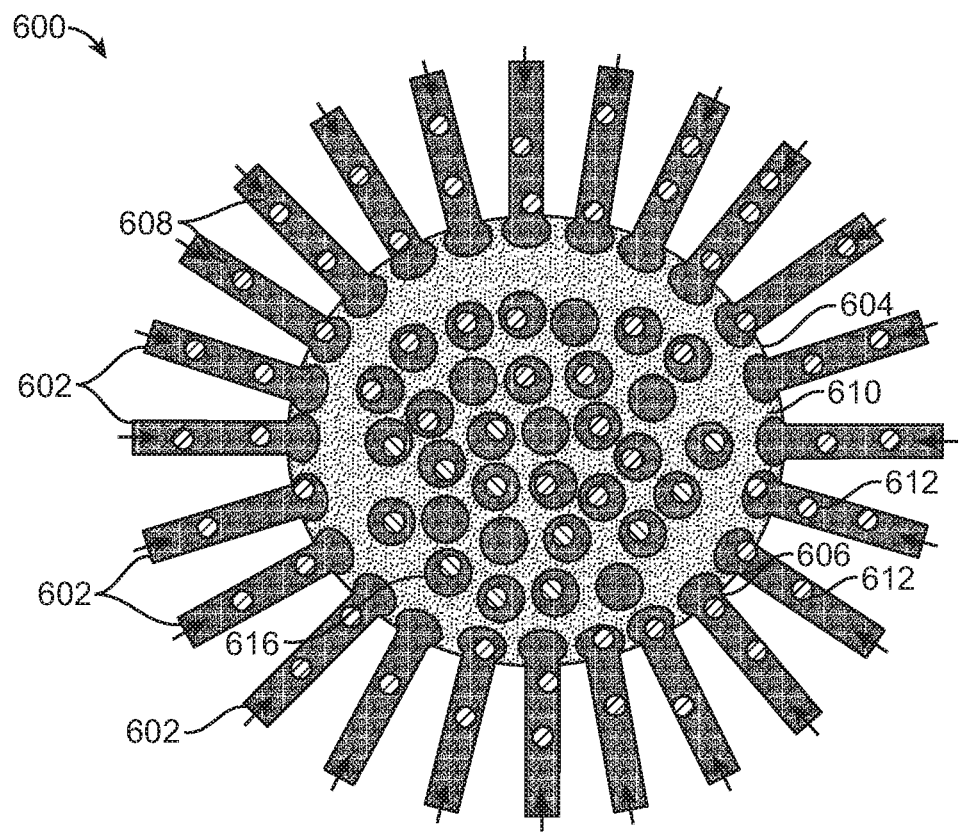
FIG. 6 shows another example of a microfluidic channel structure for increased droplet generation throughput.

FIG. 6 shows another example of a microfluidic channel structure for increased droplet generation throughput. A microfluidic channel structure 600 can comprise a plurality of channel segments 602 arranged generally circularly around the perimeter of a reservoir 604. Each of the plurality of channel segments 602 may be in fluid communication with the reservoir 604. The channel structure 600 can comprise a plurality of channel junctions 606 between the plurality of channel segments 602 and the reservoir 604. Each channel junction can be a point of droplet generation. The channel segment 402 from the channel structure 400 in FIG. 2 and any description to the components thereof may correspond to a given channel segment of the plurality of channel segments 602 in channel structure 600 and any description to the corresponding components thereof. The reservoir 404 from the channel structure 400 and any description to the components thereof may correspond to the reservoir 604 from the channel structure 600 and any description to the corresponding components thereof.

Each channel segment of the plurality of channel segments 602 may comprise an aqueous fluid 608 that includes suspended beads 612. The reservoir 604 may comprise a second fluid 610 that is immiscible with the aqueous fluid 608. In some instances, the second fluid 610 may not be subjected to and/or directed to any flow in or out of the reservoir 604. For example, the second fluid 610 may be substantially stationary in the reservoir 604. In some instances, the second fluid 610 may be subjected to flow within the reservoir 604, but not in or out of the reservoir 604, such as via application of pressure to the reservoir 604 and/or as affected by the incoming flow of the aqueous fluid 608 at the junctions. Alternatively, the second fluid 610 may be subjected and/or directed to flow in or out of the reservoir 604. For example, the reservoir 604 can be a channel directing the second fluid 610 from upstream to downstream, transporting the generated droplets.

In operation, the aqueous fluid 608 that includes suspended beads 612 may be transported along the plurality of channel segments 602 into the plurality of junctions 606 to meet the second fluid 610 in the reservoir 604 to create a plurality of droplets 616. A droplet may form from each channel segment at each corresponding junction with the reservoir 604. At the junction where the aqueous fluid 608 and the second fluid 610 meet, droplets can form based on factors such as the hydrodynamic forces at the junction, flow rates of the two fluids 608, 610, fluid properties, and certain geometric parameters (e.g., widths and heights of the channel segments 602, expansion angle of the reservoir 604, etc.) of the channel structure 600, as described elsewhere herein. A plurality of droplets can be collected in the reservoir 604 by continuously injecting the aqueous fluid 608 from the plurality of channel segments 602 through the plurality of junctions 606. Throughput may significantly increase with the substantially parallel channel configuration of the channel structure 600. A channel structure may have as many substantially parallel channel segments as is practical and allowed for by the size of the reservoir. For example, the channel structure may have at least about 2, 3, 4, 5, 6, 7, 8, 9, 10, 20, 30, 40, 50, 60, 70, 80, 90, 100, 150, 200, 250, 300, 350, 400, 450, 500, 600, 700, 800, 900, 1000, 1500, 5000 or more parallel or substantially parallel channel segments. The plurality of channel segments may be substantially evenly spaced apart, for example, around an edge or perimeter of the reservoir. Alternatively, the spacing of the plurality of channel segments may be uneven.

The reservoir 604 may have an expansion angle, α (not shown in FIG. 6) at or near each channel junction. Each channel segment of the plurality of channel segments 602 may have a width, w, and a height, $h_o$, at or near the channel junction. The geometric parameters, w, $h_o$, and α, may or may not be uniform for each of the channel segments in the plurality of channel segments 602. For example, each channel segment may have the same or different widths at or near its respective channel junction with the reservoir 604. For example, each channel segment may have the same or different height at or near its respective channel junction with the reservoir 604.

The reservoir 604 may have the same or different expansion angle at the different channel junctions with the plurality of channel segments 602. For example, a circular reservoir (as shown in FIG. 6) may have a conical, dome-like, or hemispherical ceiling (e.g., top wall) to provide the same or substantially same expansion angle for each channel segments 602 at or near the plurality of channel junctions 606. When the geometric parameters are uniform, beneficially, resulting droplet size may be controlled to be uniform even with the increased throughput. In some instances, when it is desirable to have a different distribution of droplet sizes, the geometric parameters for the plurality of channel segments 602 may be varied accordingly.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size. The beads and/or biological particle injected into the droplets may or may not have uniform size.

Figure 7A:
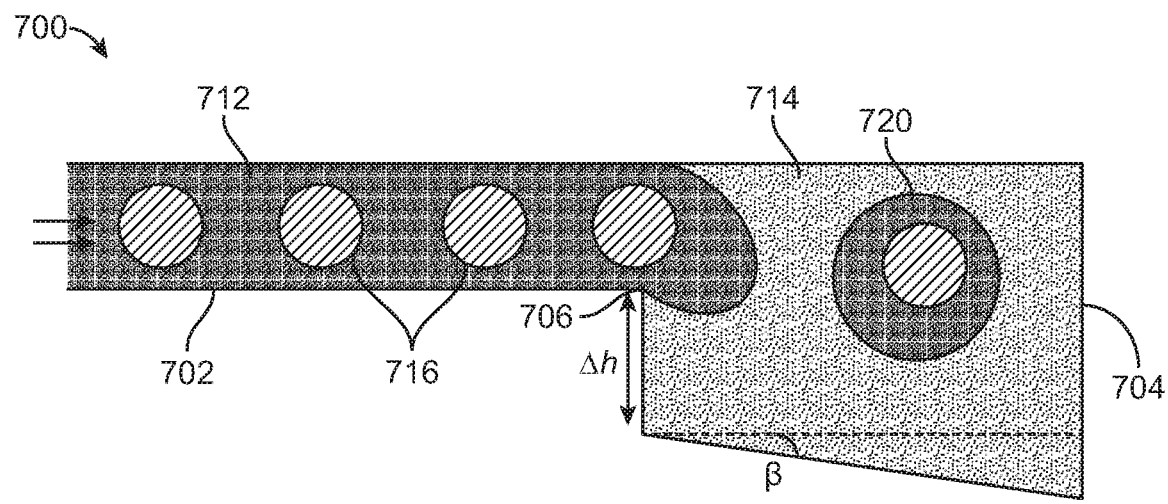
FIG. 7A shows a cross-section view of another example of a microfluidic channel structure with a geometric feature for controlled partitioning.
Figure 7B:
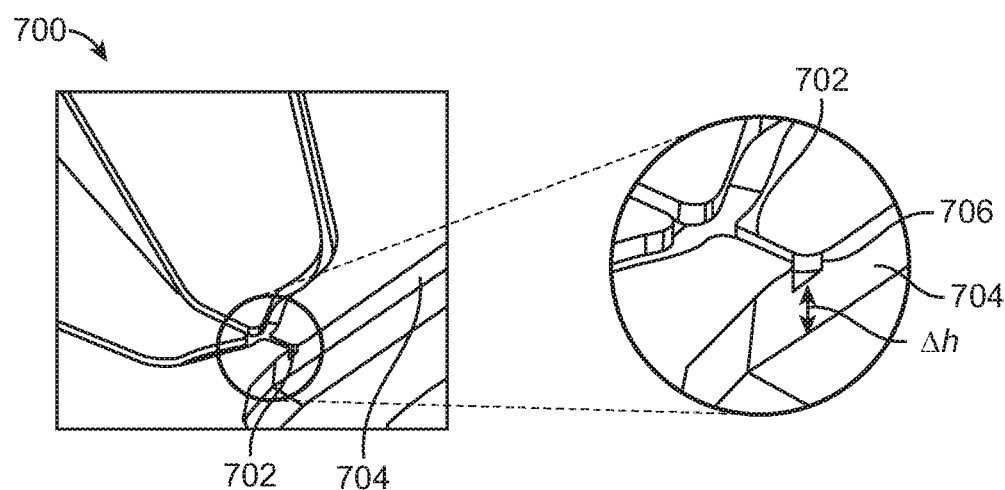
FIG. 7B shows a perspective view of the channel structure of FIG. 7A.

FIG. 7A shows a cross-section view of another example of a microfluidic channel structure with a geometric feature for controlled partitioning. A channel structure 700 can include a channel segment 702 communicating at a channel junction 706 (or intersection) with a reservoir 704. In some instances, the channel structure 700 and one or more of its components can correspond to the channel structure 100 and one or more of its components. FIG. 7B shows a perspective view of the channel structure 700 of FIG. 7A.

An aqueous fluid 712 comprising a plurality of particles 716 may be transported along the channel segment 702 into the junction 706 to meet a second fluid 714 (e.g., oil, etc.) that is immiscible with the aqueous fluid 712 in the reservoir 704 to create droplets 720 of the aqueous fluid 712 flowing into the reservoir 704. At the junction 706 where the aqueous fluid 712 and the second fluid 714 meet, droplets can form based on factors such as the hydrodynamic forces at the junction 706, relative flow rates of the two fluids 712, 714, fluid properties, and certain geometric parameters (e.g., $\Delta h$, etc.) of the channel structure 700. A plurality of droplets can be collected in the reservoir 704 by continuously injecting the aqueous fluid 712 from the channel segment 702 at the junction 706.

A discrete droplet generated may comprise one or more particles of the plurality of particles 716. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 712 can have a substantially uniform concentration or frequency of particles 716. As described elsewhere herein (e.g., with reference to FIG. 4), the particles 716 (e.g., beads) can be introduced into the channel segment 702 from a separate channel (not shown in FIG. 7). The frequency of particles 716 in the channel segment 702 may be controlled by controlling the frequency in which the particles 716 are introduced into the channel segment 702 and/or the relative flow rates of the fluids in the channel segment 702 and the separate channel. In some instances, the particles 716 can be introduced into the channel segment 702 from a plurality of different channels, and the frequency controlled accordingly. In some instances, different particles may be introduced via separate channels. For example, a first separate channel can introduce beads and a second separate channel can introduce biological particles into the channel segment 702. The first separate channel introducing the beads may be upstream or downstream of the second separate channel introducing the biological particles.

In some instances, the second fluid 714 may not be subjected to and/or directed to any flow in or out of the reservoir 704. For example, the second fluid 714 may be substantially stationary in the reservoir 704. In some instances, the second fluid 714 may be subjected to flow within the reservoir 704, but not in or out of the reservoir 704, such as via application of pressure to the reservoir 704 and/or as affected by the incoming flow of the aqueous fluid 712 at the junction 706. Alternatively, the second fluid 714 may be subjected and/or directed to flow in or out of the reservoir 704. For example, the reservoir 704 can be a channel directing the second fluid 714 from upstream to downstream, transporting the generated droplets.

The channel structure 700 at or near the junction 706 may have certain geometric features that at least partly determine the sizes and/or shapes of the droplets formed by the channel structure 700. The channel segment 702 can have a first cross-section height, $h_1$, and the reservoir 704 can have a second cross-section height, $h_2$. The first cross-section height, $h_1$, and the second cross-section height, $h_2$, may be different, such that at the junction 706, there is a height difference of $\Delta h$. The second cross-section height, $h_2$, may be greater than the first cross-section height, $h_1$. In some instances, the reservoir may thereafter gradually increase in cross-section height, for example, the more distant it is from the junction 706. In some instances, the cross-section height of the reservoir may increase in accordance with expansion angle, $\beta$, at or near the junction 706. The height difference, $\Delta h$, and/or expansion angle, $\beta$, can allow the tongue (portion of the aqueous fluid 712 leaving channel segment 702 at junction 706 and entering the reservoir 704 before droplet formation) to increase in depth and facilitate decrease in curvature of the intermediately formed droplet. For example, droplet size may decrease with increasing height difference and/or increasing expansion angle.

The height difference, $\Delta h$, can be at least about 1 µm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 µm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 µm or less. In some instances, the expansion angle, $\beta$, may be between a range of from about 0.5° to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 1°, 2°, 3° 4° 5° 6°, 7° 8°, 9° 10°, 15°, 20°, 25°, 30°, 35° 40°, 45° 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75° 70°, 65°, 60°, 55° 50°, 45° 40°, 35° 30°, 25°, 20°, 15°, 10°, 9° 8°, 7° 6°, 5° 4° 3° 2°, 1°, 0.1°, 0.01°, or less.

In some instances, the flow rate of the aqueous fluid 712 entering the junction 706 can be between about 0.04 microliters (µL)/minute (min) and about 40 µL/min. In some instances, the flow rate of the aqueous fluid 712 entering the junction 706 can be between about 0.01 microliters (µL)/minute (min) and about 100 µL/min. Alternatively, the flow rate of the aqueous fluid 712 entering the junction 706 can be less than about 0.01 µL/min. Alternatively, the flow rate of the aqueous fluid 712 entering the junction 706 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 L/min, or greater. At lower flow rates, such as flow rates of about less than or equal to 10 microliters/minute, the droplet radius may not be dependent on the flow rate of the aqueous fluid 712 entering the junction 706. The second fluid 714 may be stationary, or substantially stationary, in the reservoir 704. Alternatively, the second fluid 714 may be flowing, such as at the above flow rates described for the aqueous fluid 712.

In some instances, at least about 50% of the droplets generated can have uniform size. In some instances, at least about 55%, 60%, 65%, 70%, 75%, 80%, 85%, 90%, 95%, 96%, 97%, 98%, 99%, or greater of the droplets generated can have uniform size. Alternatively, less than about 50% of the droplets generated can have uniform size.

While FIGS. 7A and 7B illustrate the height difference, $\Delta h$, being abrupt at the junction 706 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 706, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIGS. 7A and 7B illustrate the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

The channel networks, e.g., as described above or elsewhere herein, can be fluidly coupled to appropriate fluidic components. For example, the inlet channel segments are fluidly coupled to appropriate sources of the materials they are to deliver to a channel junction. These sources may include any of a variety of different fluidic components, from simple reservoirs defined in or connected to a body structure of a microfluidic device, to fluid conduits that deliver fluids from off-device sources, manifolds, fluid flow units (e.g., actuators, pumps, compressors) or the like. Likewise, the outlet channel segment (e.g., channel segment 208, reservoir 604, etc.) may be fluidly coupled to a receiving vessel or conduit for the partitioned cells for subsequent processing. Again, this may be a reservoir defined in the body of a microfluidic device, or it may be a fluidic conduit for delivering the partitioned cells to a subsequent process operation, instrument or component.

The methods and systems described herein may be used to greatly increase the efficiency of single cell applications and/or other applications receiving droplet-based input. For example, following the sorting of occupied cells and/or appropriately-sized cells, subsequent operations that can be performed can include generation of amplification products, purification (e.g., via solid phase reversible immobilization (SPRI)), further processing (e.g., shearing, ligation of functional sequences, and subsequent amplification (e.g., via PCR)). These operations may occur in bulk (e.g., outside the partition). In the case where a partition is a droplet in an emulsion, the emulsion can be broken and the contents of the droplet pooled for additional operations. Additional reagents that may be co-partitioned along with the barcode bearing bead may include oligonucleotides to block ribosomal RNA (rRNA) and nucleases to digest genomic DNA from cells. Alternatively, rRNA removal agents may be applied during additional processing operations. The configuration of the constructs generated by such a method can help minimize (or avoid) sequencing of the poly-T sequence during sequencing and/or sequence the 5' end of a polynucleotide sequence. The amplification products, for example, first amplification products and/or second amplification products, may be subject to sequencing for sequence analysis. In some cases, amplification may be performed using the Partial Hairpin Amplification for Sequencing (PHASE) method.

A variety of applications require the evaluation of the presence and quantification of different biological particle or organism types within a population of biological particles, including, for example, microbiome analysis and characterization, environmental testing, food safety testing, epidemiological analysis, e.g., in tracing contamination or the like.

Kits

Also provided herein are kits for analyzing the accessible chromatin (e.g., for ATAC-seq) and/or RNA transcripts of individual cells or small populations of cells. The kits may include one or more of the following: one, two, three, four, five or more, up to all of partitioning fluids, including both aqueous buffers and non-aqueous partitioning fluids or oils, nucleic acid barcode libraries that are releasably associated with beads, as described herein, microfluidic devices, reagents for disrupting cells amplifying nucleic acids, and providing additional functional sequences on fragments of cellular nucleic acids or replicates thereof, as well as instructions for using any of the foregoing in the methods described herein.

Computer Systems

Figure 9:
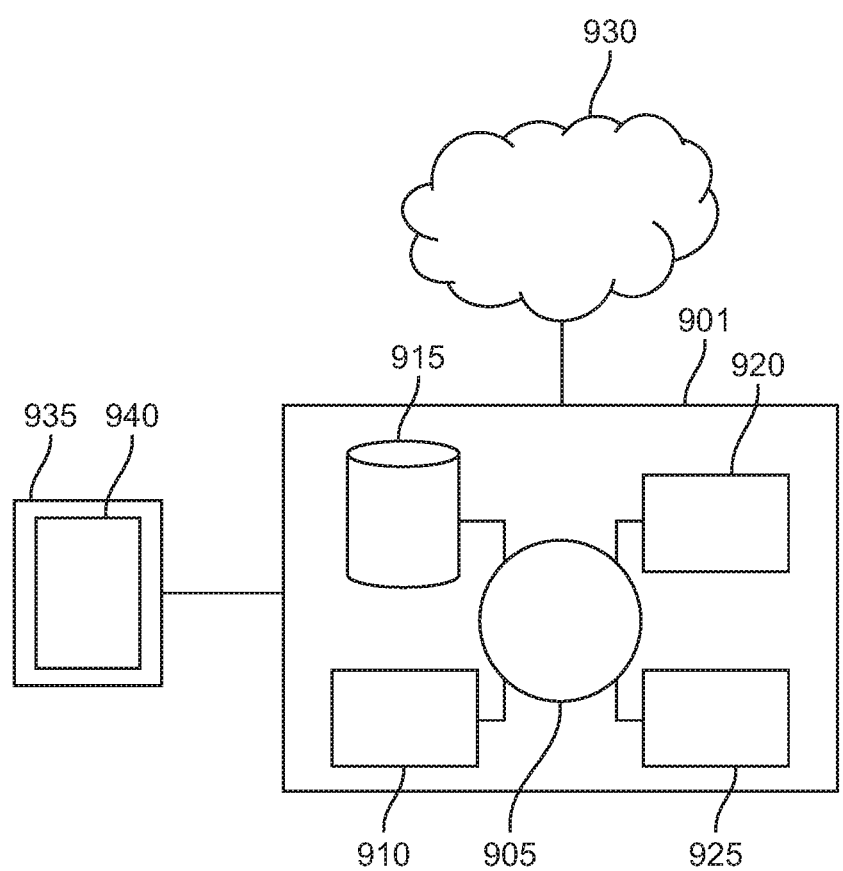
FIG. 9 shows a computer system that is programmed or otherwise configured to implement methods provided herein.

The present disclosure provides computer systems that are programmed to implement methods of the disclosure. FIG. 9 shows a computer system 901 that is programmed or otherwise configured to, e.g., (i) control a microfluidics system (e.g., fluid flow), (ii) sort occupied droplets from unoccupied droplets, (iii) polymerize droplets, (iv) perform sequencing applications, (v) generate and maintain a library of DNA or cDNA fragments, and/or (vi) analyze areas of accessible chromatin. The computer system 901 can regulate various aspects of the present disclosure, such as, for example, e.g., regulating fluid flow rate in one or more channels in a microfluidic structure, regulating polymerization application units, regulating conditions for certain reactions described herein. The computer system 901 can be an electronic device of a user or a computer system that is remotely located with respect to the electronic device. The electronic device can be a mobile electronic device.

The computer system 901 includes a central processing unit (CPU, also "processor" and "computer processor" herein) 905, which can be a single core or multi core processor, or a plurality of processors for parallel processing. The computer system 901 also includes memory or memory location 910 (e.g., random-access memory, read-only memory, flash memory), electronic storage unit 915 (e.g., hard disk), communication interface 920 (e.g., network adapter) for communicating with one or more other systems, and peripheral devices 925, such as cache, other memory, data storage and/or electronic display adapters. The memory 910, storage unit 915, interface 920 and peripheral devices 925 are in communication with the CPU 905 through a communication bus (solid lines), such as a motherboard. The storage unit 915 can be a data storage unit (or data repository) for storing data. The computer system 901 can be operatively coupled to a computer network ("network") 930 with the aid of the communication interface 920. The network 930 can be the Internet, an internet and/or extranet, or an intranet and/or extranet that is in communication with the Internet. The network 930 in some cases is a telecommunication and/or data network. The network 930 can include one or more computer servers, which can enable distributed computing, such as cloud computing. The network 930, in some cases with the aid of the computer system 901, can implement a peer-to-peer network, which may enable devices coupled to the computer system 901 to behave as a client or a server.

The CPU 905 can execute a sequence of machine-readable instructions, which can be embodied in a program or software. The instructions may be stored in a memory location, such as the memory 910. The instructions can be directed to the CPU 905, which can subsequently program or otherwise configure the CPU 905 to implement methods of the present disclosure. Examples of operations performed by the CPU 905 can include fetch, decode, execute, and writeback.

The CPU 905 can be part of a circuit, such as an integrated circuit. One or more other components of the system 901 can be included in the circuit. In some cases, the circuit is an application specific integrated circuit (ASIC).

The storage unit 915 can store files, such as drivers, libraries and saved programs. The storage unit 915 can store user data, e.g., user preferences and user programs. The computer system 901 in some cases can include one or more additional data storage units that are external to the computer system 901, such as located on a remote server that is in communication with the computer system 901 through an intranet or the Internet.

The computer system 901 can communicate with one or more remote computer systems through the network 930. For instance, the computer system 901 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 901 via the network 930.

Methods as described herein can be implemented by way of machine (e.g., computer processor) executable code stored on an electronic storage location of the computer system 901, such as, for example, on the memory 910 or electronic storage unit 915. The machine executable or machine readable code can be provided in the form of software. During use, the code can be executed by the processor 905. In some cases, the code can be retrieved from the storage unit 915 and stored on the memory 910 for ready access by the processor 905. In some situations, the electronic storage unit 915 can be precluded, and machine-executable instructions are stored on memory 910.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 901, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 901 can include or be in communication with an electronic display 935 that comprises a user interface (UI) 940 for providing, for example, results of sequencing analysis, correlating sequencing reads to areas of accessible chromatin, etc. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 905. The algorithm can, for example, perform sequencing reactions, correlating sequencing reads to areas of accessible chromatin, etc.

Devices, systems, compositions and methods of the present disclosure may be used for various applications, such as, for example, processing a single analyte (e.g., RNA, DNA, or protein) or multiple analytes (e.g., DNA and RNA, DNA and protein, RNA and protein, or RNA, DNA and protein) form a single cell. For example, a biological particle (e.g., a cell or cell bead) is partitioned in a partition (e.g., droplet), and multiple analytes from the biological particle are processed for subsequent processing. The multiple analytes may be from the single cell. This may enable, for example, simultaneous proteomic, transcriptomic and genomic analysis of the cell.

EXAMPLES

Although the Examples herein make use of droplet emulsion partitions, any of the above-described partitions (such

Example 1. Generation of Barcoded Nucleic Acid Fragments from Single Cells Using Forked Adaptors Comprising Transposon End Sequences A plurality of transposase molecules, a plurality of cells of interest (or a plurality of nuclei harvested from cells of interest, e.g., by nonionic detergents such as NP-40 (IG-EPAL CA-630) or Triton X-100), and a plurality of barcode oligonucleotides are partitioned such that at least some partitions comprise a plurality of transposase molecules, a single cell (or nucleus), and a plurality of barcode oligonucleotides comprising a sequencing primer sequence, a barcode sequence, and a transposon end sequence. In some embodiments, the plurality of barcode oligonucleotides are attached to a gel bead and partitioned such that at least some partitions comprise transposase molecules, a single cell (or nucleus), and a single gel bead.

Figure 10:
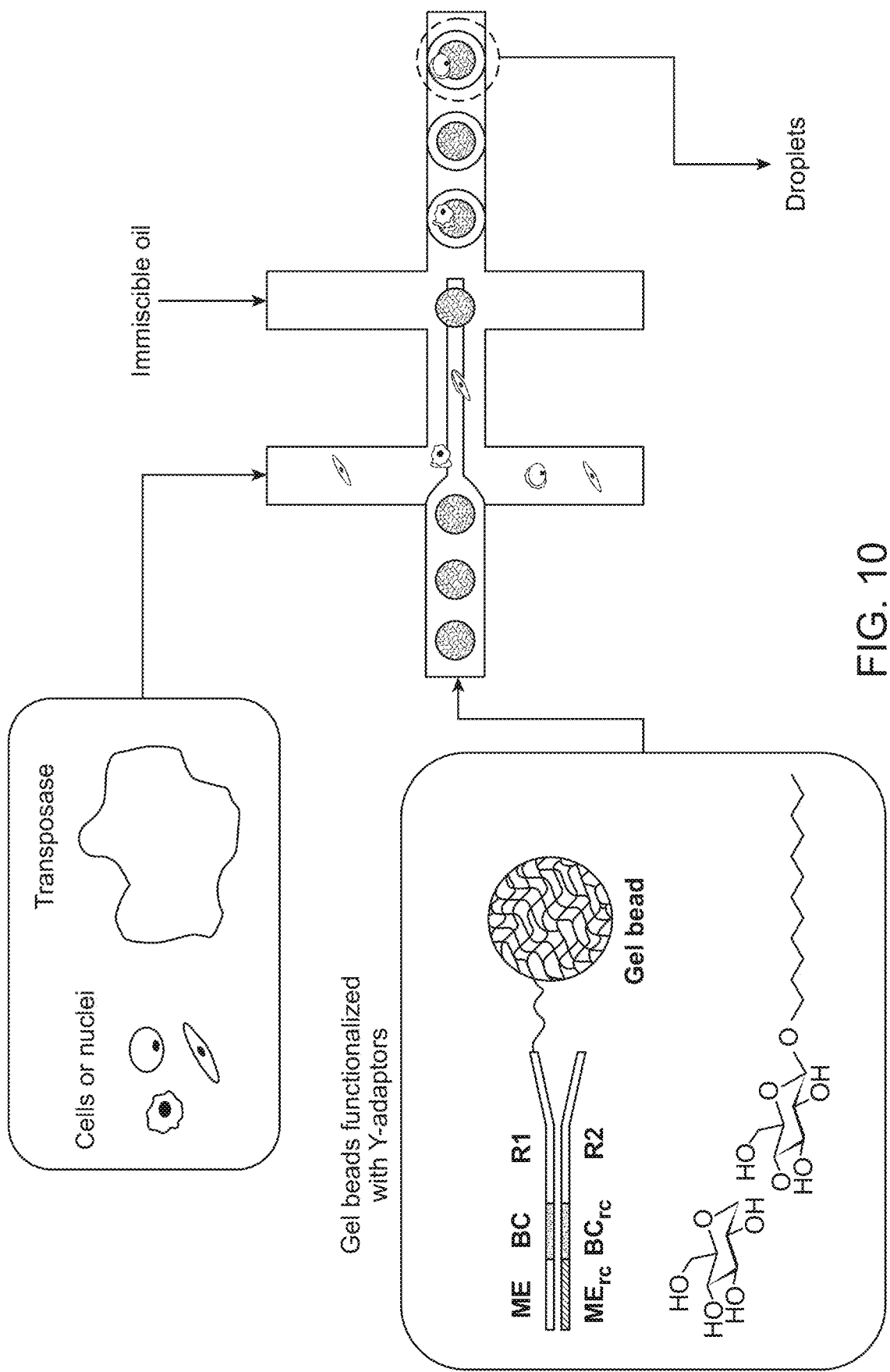
FIG. 10 illustrates an exemplary method to produce droplets wherein at least some of the droplets formed will comprise transposase molecules, a single cell, and a single gel bead comprising a forked adaptor.
Figure 11A:
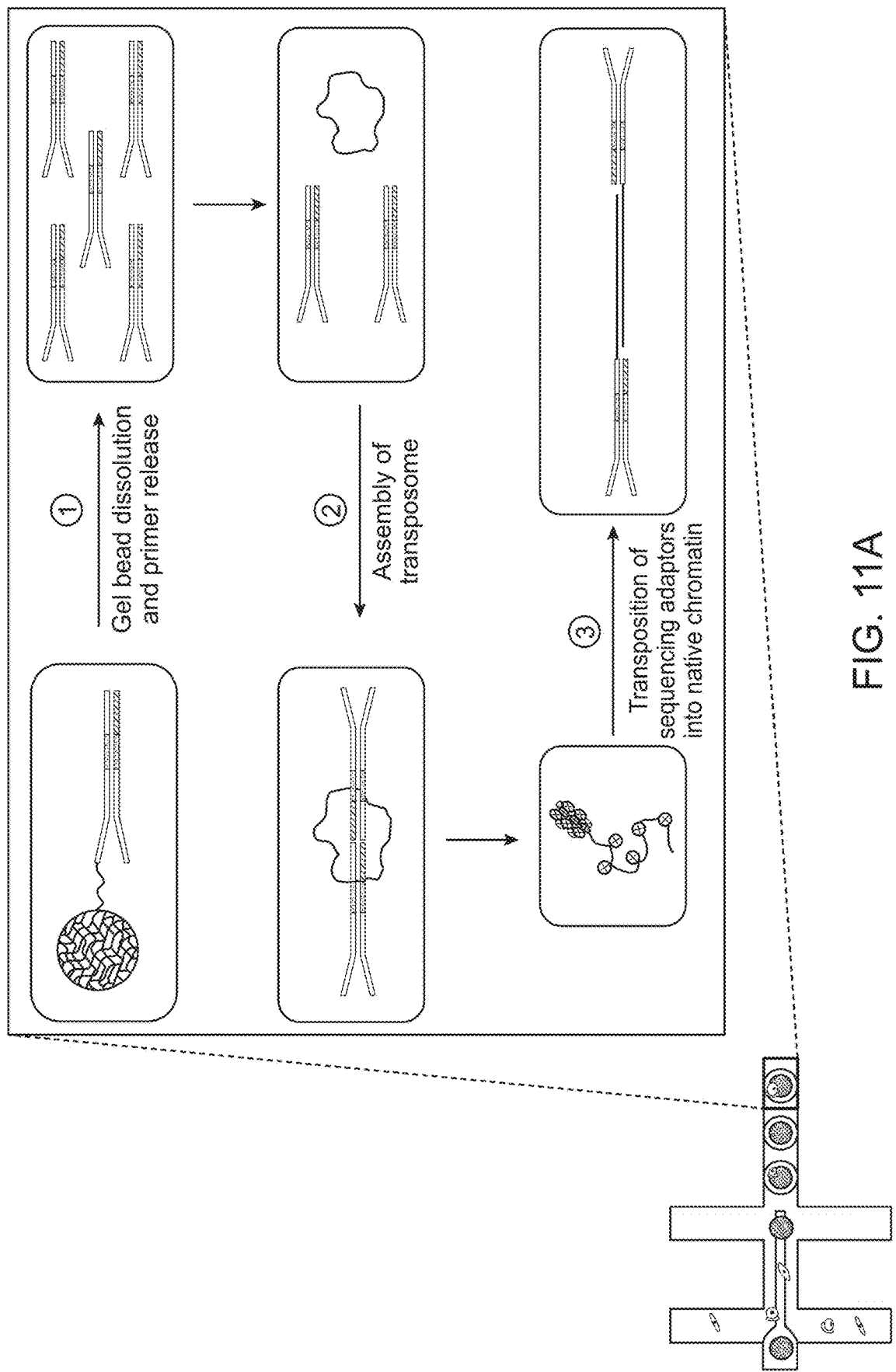
FIGS. 11A-11B illustrate an exemplary method to produce forked adaptor flanked double-stranded template nucleic acid fragments.

For example, in some embodiments, droplet emulsion partitions are generated as described herein such that at least some of the droplets formed will comprise transposase molecules, cell lysis reagents, a single cell, and a single gel bead comprising a plurality of barcoded forked adapter oligonucleotides. See, e.g., FIG. 10. The cells are then lysed in a manner that releases template nucleic acid molecules from the nucleus into the aqueous droplet, but that substantially maintains native chromatin organization. Droplets are then generally processed as outlined in FIG. 11A.

Figure 12A:
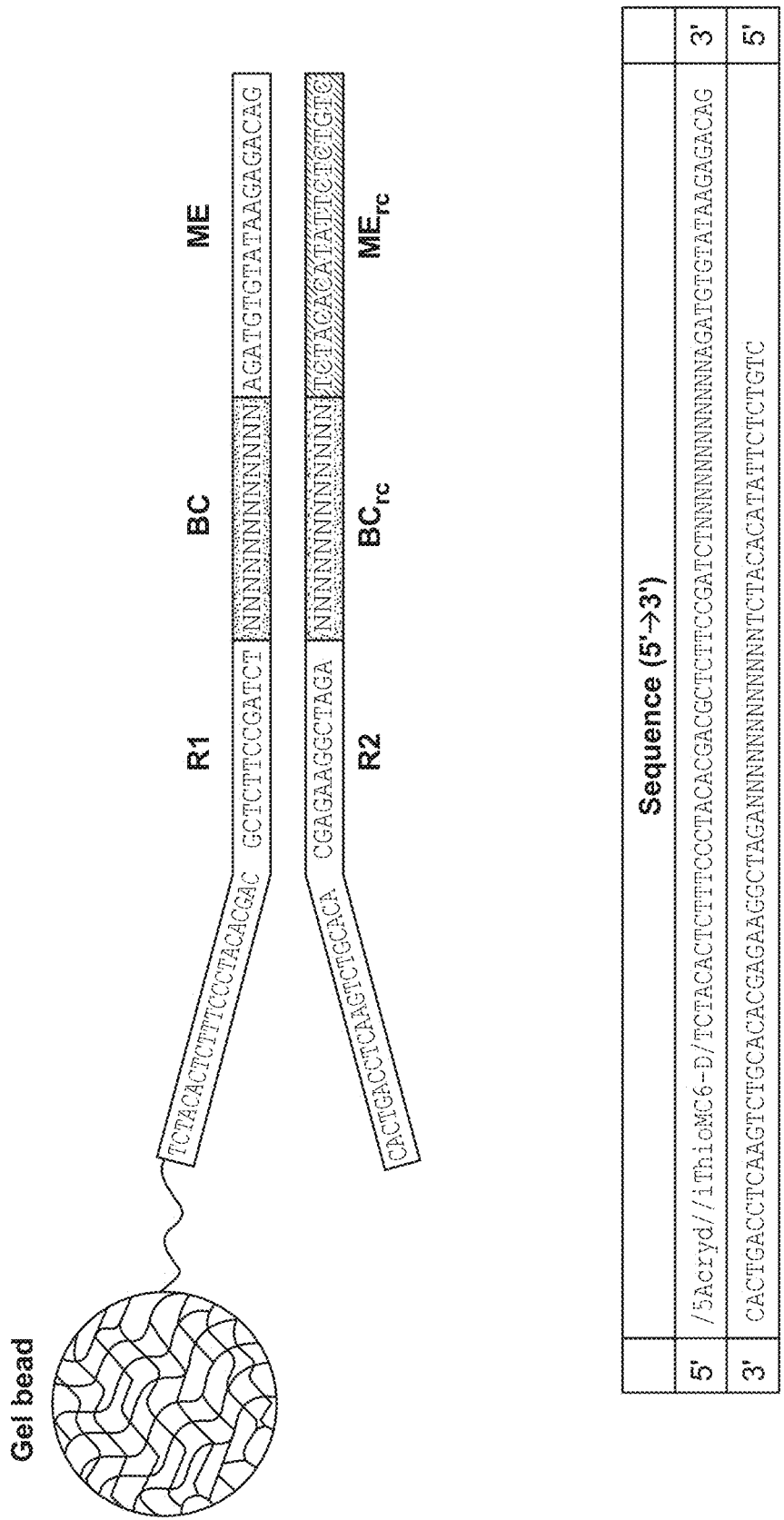
FIGS. 12A-12B illustrate exemplary forked adaptors.

Specifically, a droplet is subjected to conditions such that the forked adaptors are released from the gel bead into the aqueous droplet (e.g., by gel bead depolymerization using a reducing agent, such as DTT). Although the forked adaptors can be prepared in a variety of different configurations, an exemplary forked adaptor is illustrated in FIG. 12A and shows a partially complementary double-stranded oligonucleotide comprising a first oligonucleotide strand releasably attached to a gel bead and a second partially complementary oligonucleotide strand. With continued reference to FIG. 12A, the first strand comprises a transposon end sequence ("mosaic end" or "ME"), a barcode sequence ("BC"), and a sequencing primer sequence ("R1"). The partially complementary second strand comprises: (i) a region fully complementary to the transposon end sequence; (ii) a region fully complementary to the barcode sequence; and (iii) a primer sequence ("R2") partially complementary to the first strand primer sequence.

Figure 12B:
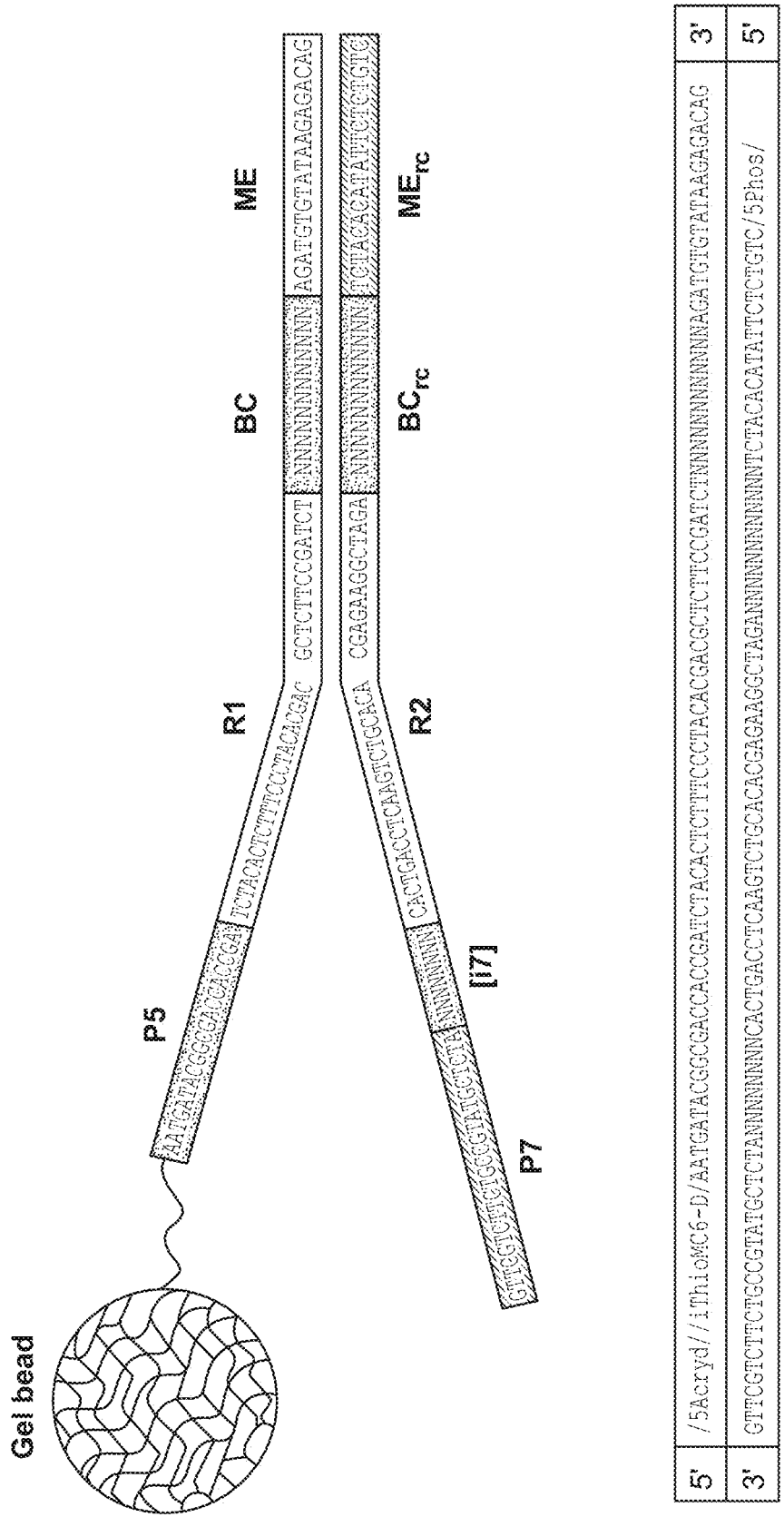

In alternative embodiments (e.g., FIG. 12B), the double-stranded forked adaptor of FIG. 12A further comprises: (a) a first oligonucleotide strand further comprising a P5 sequence releasably attached to the gel bead; and (b) a second partially complementary oligonucleotide strand further comprising an index sequence ("i7") and a P7 sequence.

After the forked adaptors are released from the gel bead, a droplet is then subjected to conditions such that a transposase-nucleic acid complex is formed comprising a transposase molecule and two forked adaptors. See FIG. 11A, step 2. The droplets are then subjected to conditions such that the transposase-nucleic acid complexes integrate the transposon end sequences into the template nucleic acid and fragment the template nucleic acid into double-stranded template nucleic acid fragments flanked by the forked adaptors. See FIG. 11A, step 3. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

Figure 11B:
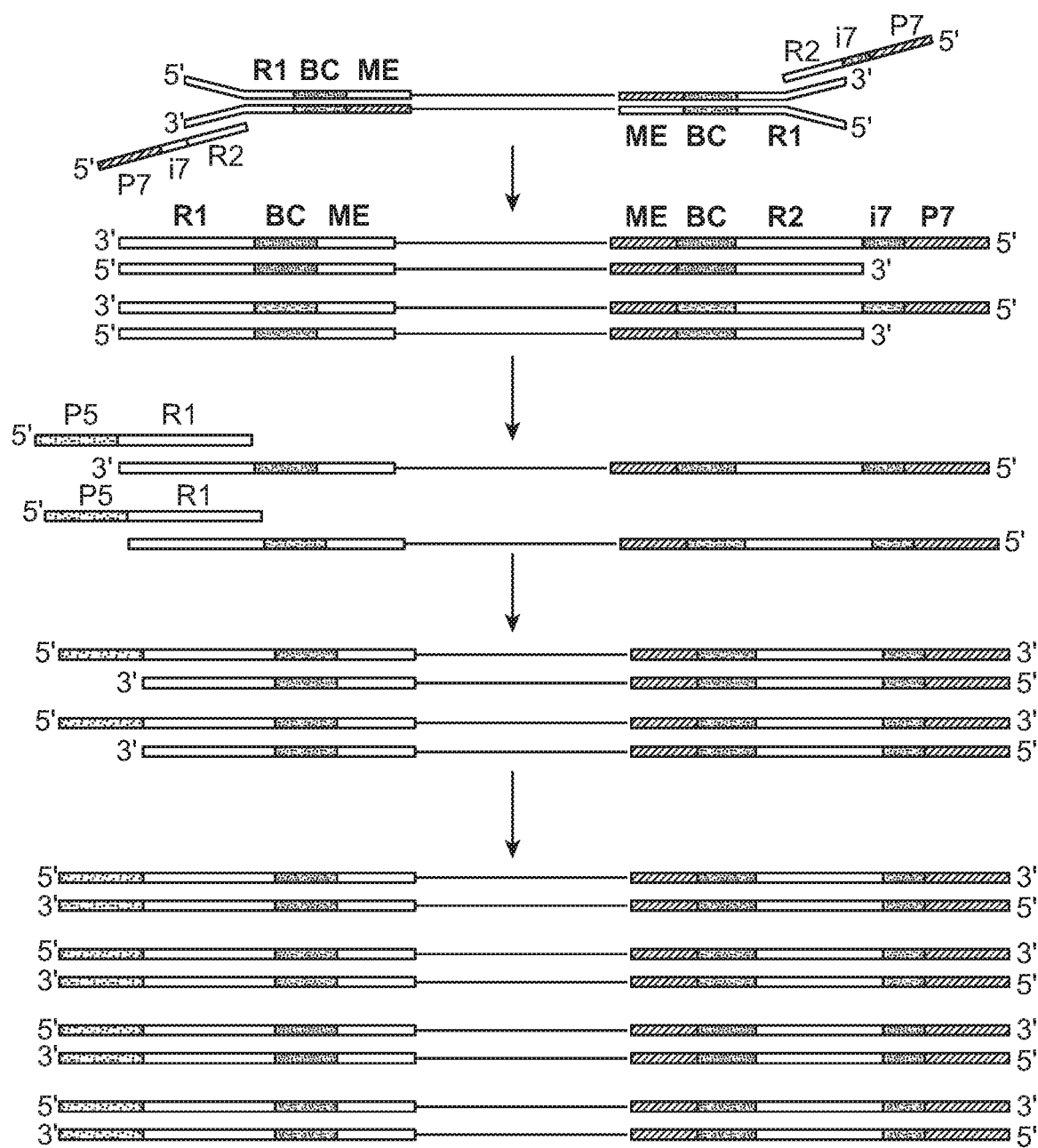

The fragmented double-stranded template nucleic acid fragments are then collected from the droplets and processed in bulk to fill any gaps created from the transposition reaction and to generate a library suitable for next generation high throughput sequencing (e.g., subjecting the fragments, or derivatives thereof, to one or more reactions (e.g., nucleic acid amplification) to add functional sequences to facilitate Illumina sequencing; see FIG. 11B). The fully constructed library is then sequenced according to any suitable sequencing protocol.

Example 2. Generation of Barcoded Nucleic Acid Fragments from Single Cells Using Forked Adaptors and Transposase-Nucleic Acid Complexes A plurality of transposase-nucleic acid complexes, a plurality of cells of interest (or a plurality of nuclei harvested from cells of interest), and a plurality of barcode oligonucleotides are partitioned such that at least some partitions comprise a plurality of transposase-nucleic acid complexes, a single cell (or nucleus), and a plurality of barcode oligonucleotides comprising a sequencing primer sequence and a barcode sequence. In some embodiments, the plurality of barcode oligonucleotides are attached to a gel bead and partitioned such that at least some partitions comprise transposase-nucleic acid complexes, a single cell (or nucleus), and a single gel bead. In alternative embodiments, a plurality of transposase molecules and a plurality of transposon end sequence oligonucleotides are partitioned along with a single cell (or nucleus) and the barcode oligonucleotides and transposase-nucleic acid complexes are generated in the partition.

Figure 13:
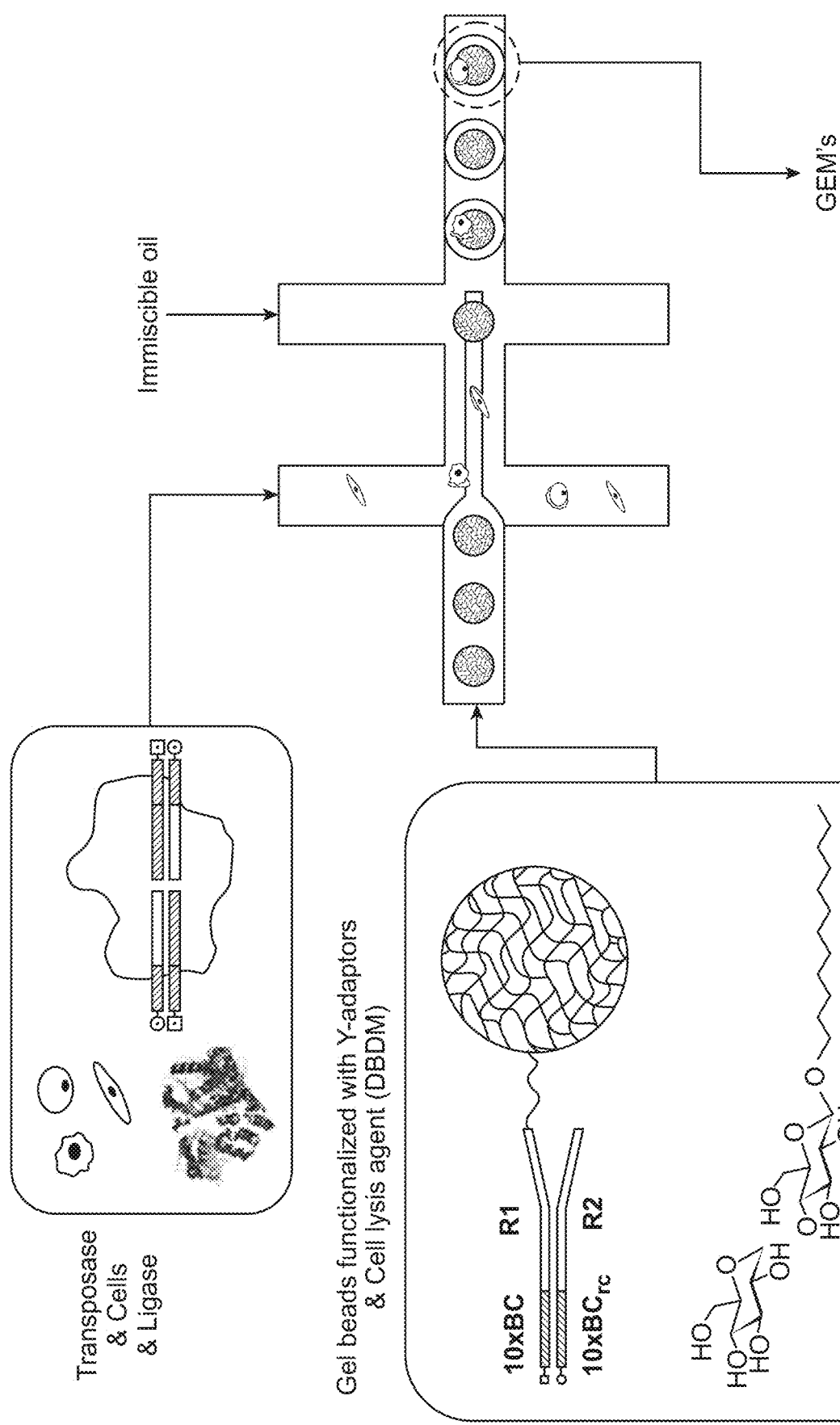
FIG. 13 illustrates an exemplary method to produce droplets wherein at least some of the droplets formed will comprise transposase-nucleic acid complexes, a single cell, and a single gel bead comprising a forked adaptor.

For example, in some embodiments, droplet emulsion partitions are generated as described herein such that at least some of the droplets comprise transposase-nucleic acid complexes, cell lysis reagents, T4 DNA ligase, a single cell, and a single gel bead comprising a plurality of barcoded forked adapter oligonucleotides. See, e.g., FIG. 13.

Figure 14A:
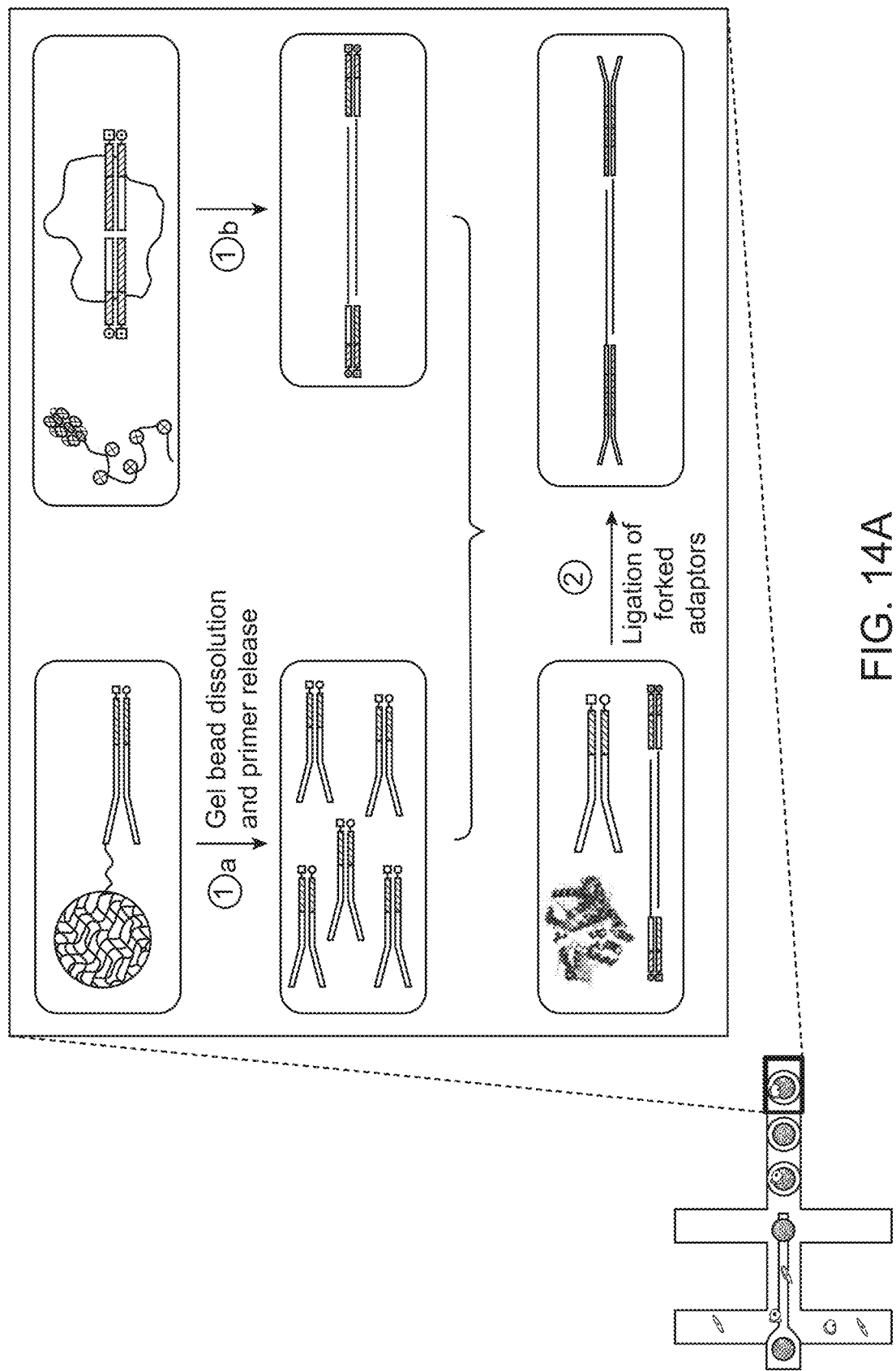
FIGS. 14A-14B illustrate an alternative exemplary method to produce forked adaptor flanked double-stranded template nucleic acid fragments.

An individual transposase-nucleic acid complex comprises a transposase and a pair of double-stranded oligonucleotides each comprising a transposon end sequence (e.g., an ME sequence). See FIGS. 13-15. In some embodiments, the double-stranded transposon-end sequence containing oligonucleotides further comprise a spacer sequence.

After droplet formation, single cells are lysed in a manner that releases template nucleic acid molecules from the nucleus into the aqueous droplet, but that substantially maintains native chromatin organization. Droplets are then generally processed as outlined in FIG. 14A.

Figure 15A:
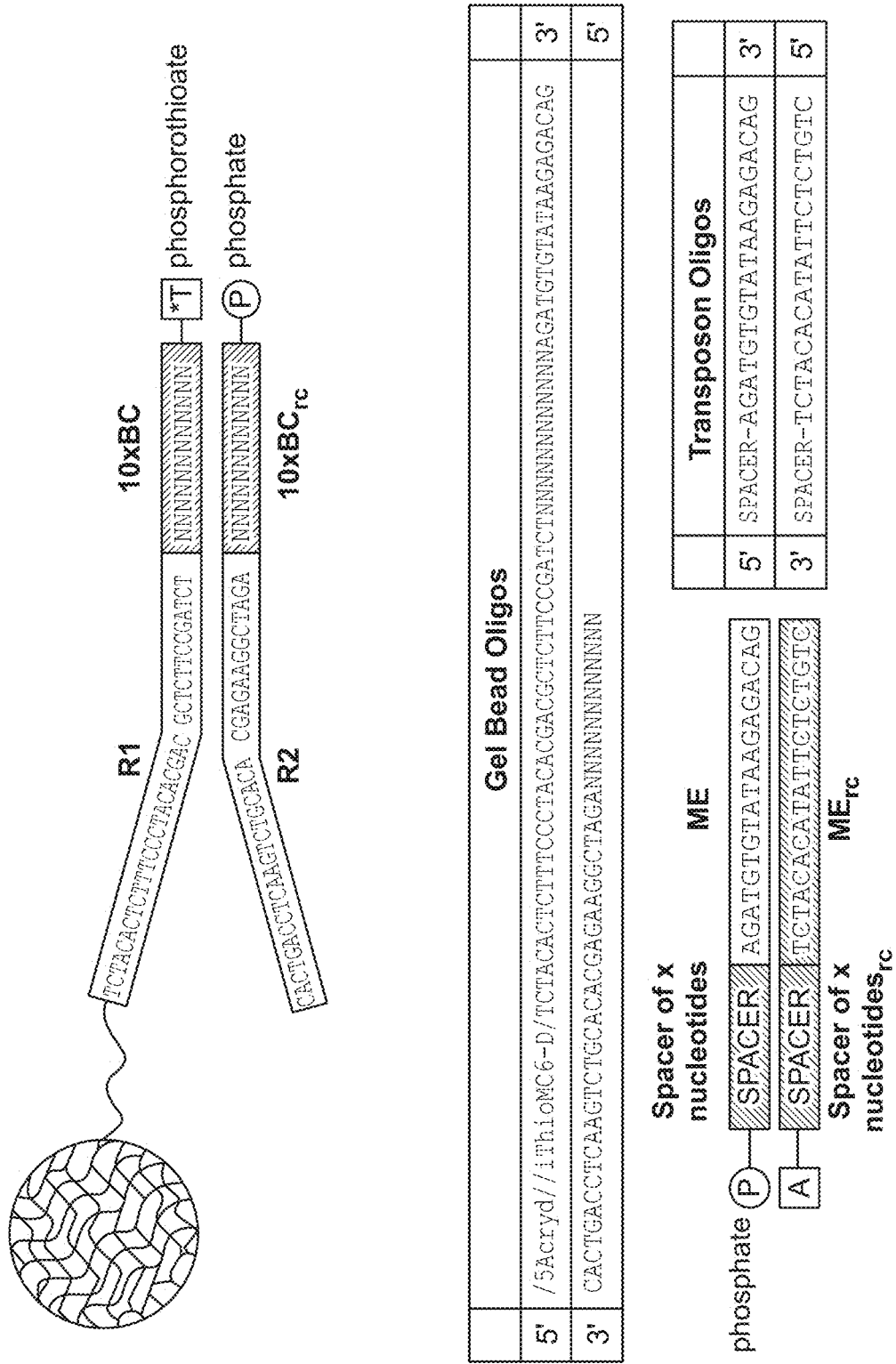
FIGS. 15A-15B illustrate additional exemplary forked adaptors and transposon end sequence containing oligonucleotides.

Specifically, a droplet is subjected to conditions such that the forked adaptors are released from the gel bead into the aqueous droplet (e.g., by gel bead depolymerization using a reducing agent, such as DTT). See FIG. 14A, step 1a. Although the forked adaptors can be prepared in a variety of different configurations, an exemplary forked adaptor is illustrated in FIG. 15A and shows a double-stranded oligonucleotide comprising a first oligonucleotide strand releasably attached to a gel bead and a second partially complementary oligonucleotide strand. With continued reference to FIG. 15A, the first strand comprises a barcode sequence ("BC") and a primer sequence ("R1"). The partially complementary second strand comprises a region fully complementary to the barcode sequence and a primer sequence ("R2") partially complementary to the first strand primer sequence. In some embodiments, the first strand further comprises a phosphorothioate linkage in the terminal nucleotide at the 3' end. In other embodiments, the first strand comprises phosphorothioate linkages in the last 3-5 nucleotides at the 3' end. In still other embodiments, the first strand comprises phosphorothioate linkages throughout the first strand.

In alternative embodiments (e.g., FIG. 15B), the double-stranded forked adaptor described in FIG. 15A further comprises a first oligonucleotide strand further comprising a P5 adapter sequence releasably attached to the gel bead; and (b) a second partially complementary oligonucleotide strand further comprising an index primer ("i7") and an adaptor sequence different than the first strand ("P7").

After the forked adaptors are released from the gel bead, a droplet is then subjected to conditions such that the transposase-nucleic acid complexes integrate the transposon end sequences into the template nucleic acid and fragment the template nucleic acid into double-stranded template nucleic acid fragments flanked by transposon end sequences. See FIG. 14A, step 1b. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell. The forked adaptors are then ligated onto the ends of the double-stranded stranded template nucleic acid fragments. See FIG. 14A, step 2.

Figure 14B:
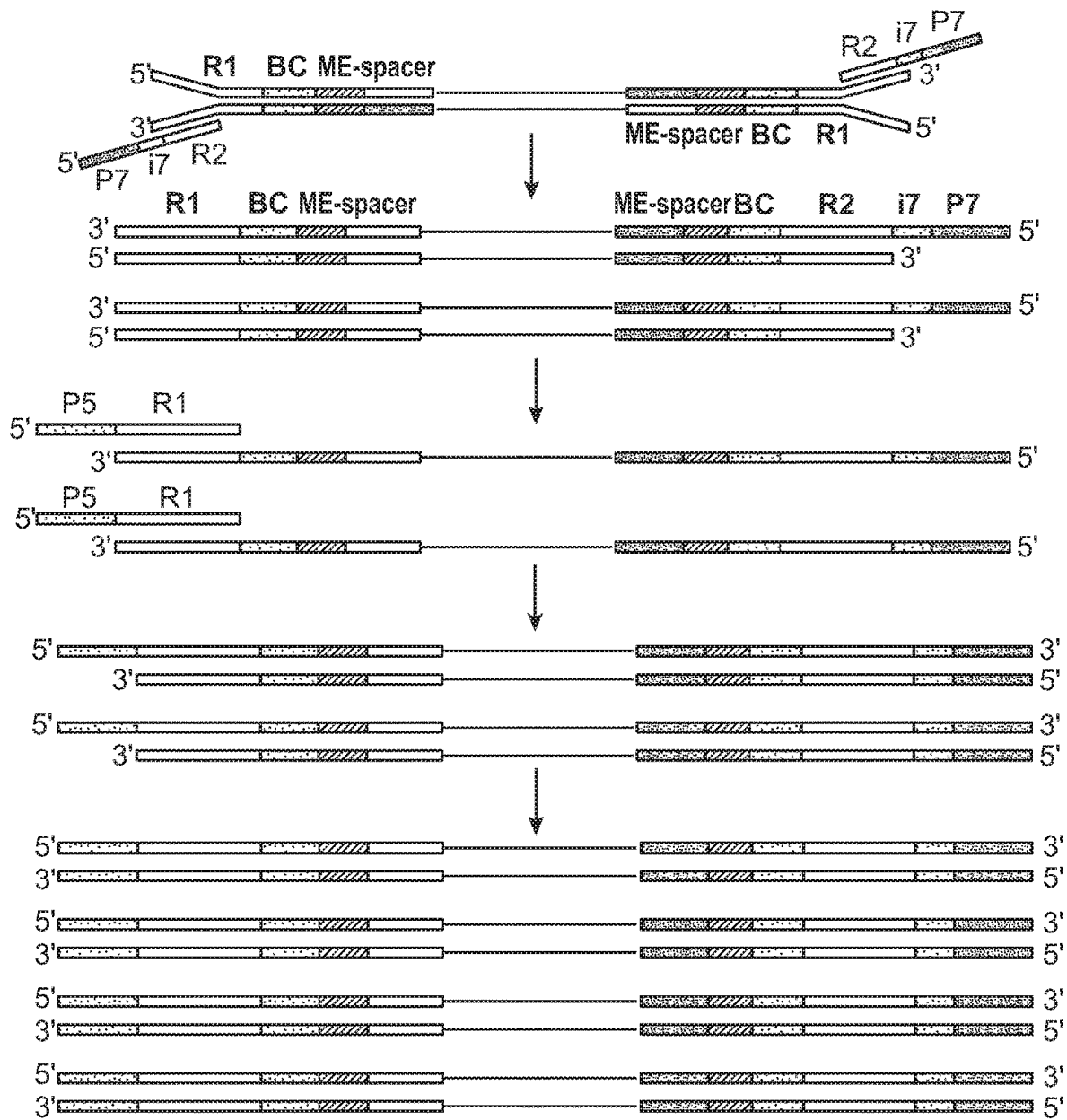
Figure 15B:
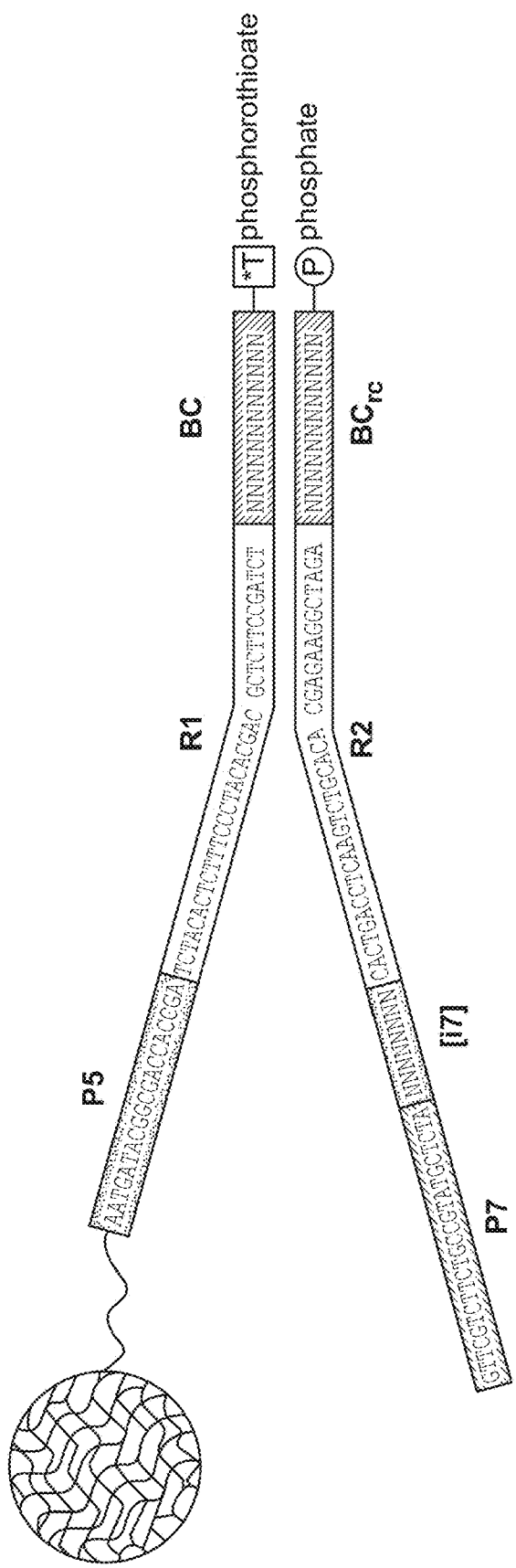

The fragmented double-stranded template nucleic acid fragments are then collected from the droplets and processed in bulk to fill any gaps created from the transposition reaction and to generate a library suitable for next generation high throughput sequencing (e.g., subjecting the fragments, or derivatives thereof, to one or more reactions (e.g., nucleic acid amplification) to add functional sequences to facilitate Illumina sequencing; see FIG. 14B). The fully constructed library is then sequenced according to any suitable sequencing protocol. In some embodiments, custom sequencing primers directed against the spacer-ME sequence are utilized to avoid sequencing the barcode-spacer-ME region of the library.

Example 3. Generation of Barcoded Nucleic Acid Fragments from Single Cells Using Adaptors Comprising a T7 Promoter Sequence A plurality of transposase molecules, a plurality of cells of interest (or a plurality of nuclei harvested from cells of interest), and a plurality of barcode oligonucleotides are partitioned such that at least some partitions comprise a plurality of transposase molecules, a single cell (or nucleus), and a plurality of barcode oligonucleotides comprising a T7 promoter sequence, a sequencing primer sequence, a barcode sequence, and a transposon end sequence. In some embodiments, the plurality of barcode oligonucleotides are attached to a gel bead and partitioned such that at least some partitions comprise transposase molecules, a single cell (or nucleus), and a single gel bead.

Figure 16:
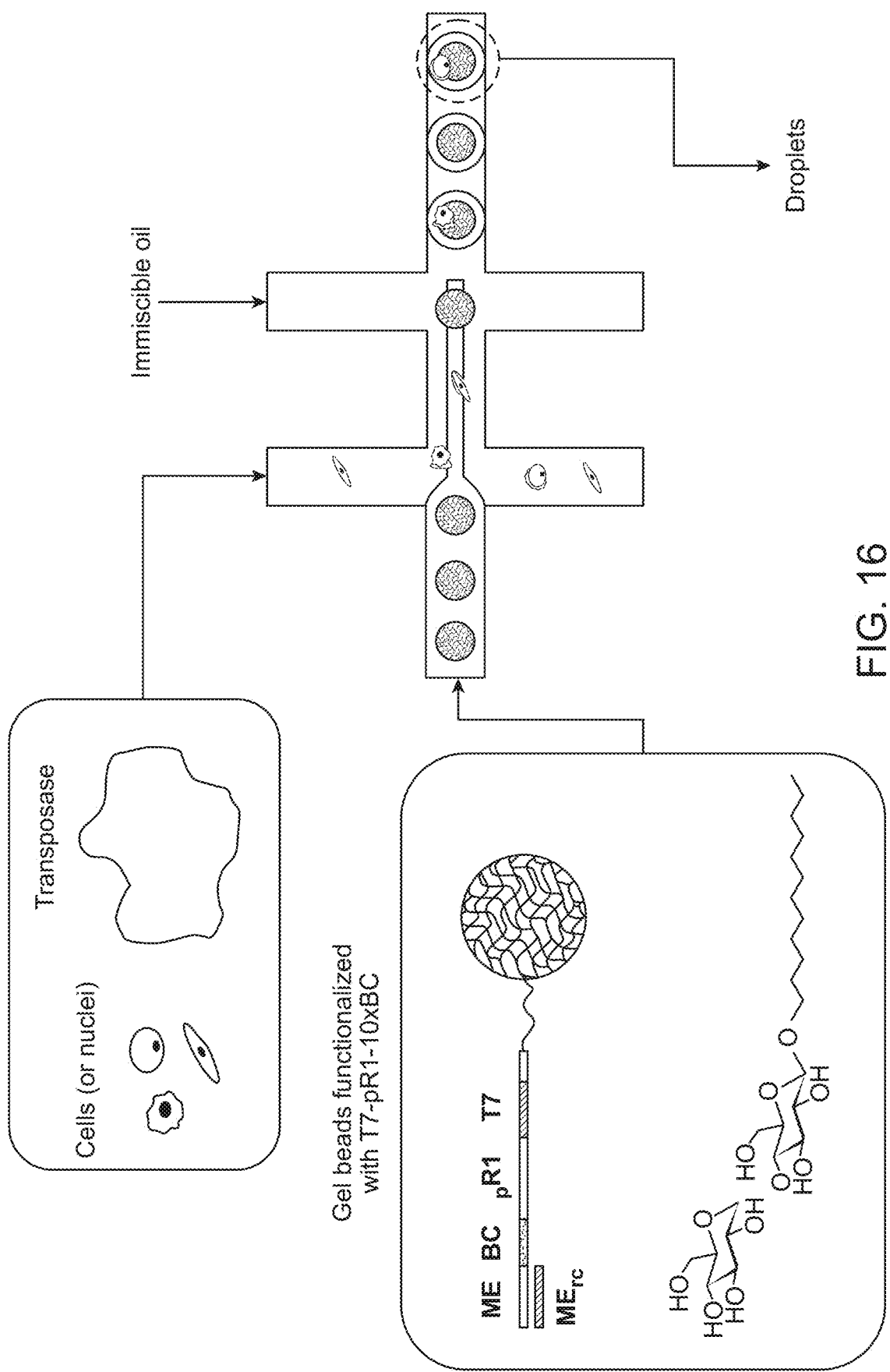
FIG. 16 illustrates an exemplary method to produce droplets wherein at least some of the droplets formed will comprise transposase molecules, a single cell, and a single gel bead comprising a T7-containing adaptor.
Figure 17:
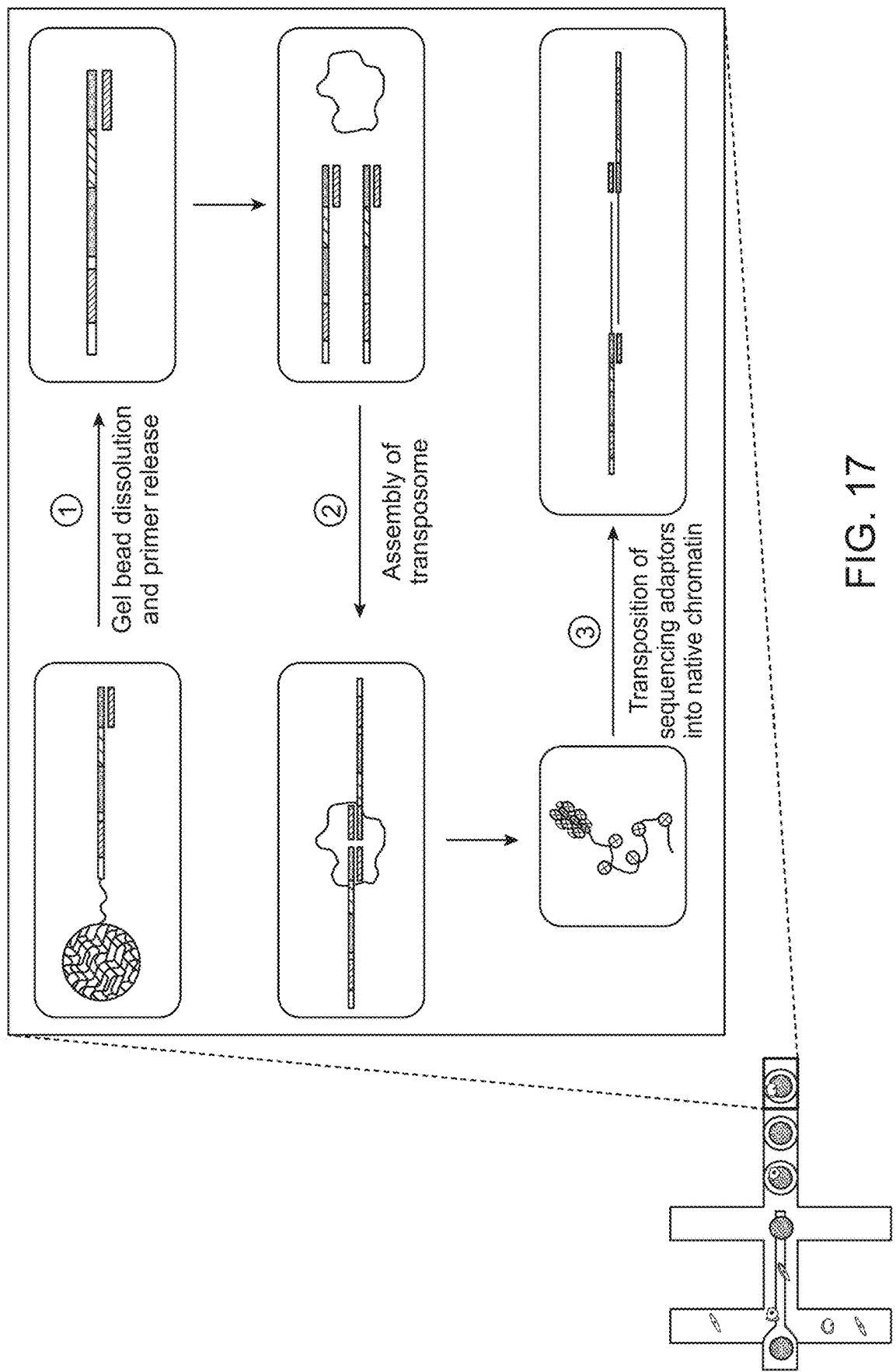
FIG. 17 illustrates an exemplary method to produce T7-containing adaptor flanked double-stranded template nucleic acid fragments.

For example, in some embodiments, droplet emulsion partitions are generated as previously described such that at least some droplets that comprise transposase molecules, cell lysis reagents, a single cell, and a single gel bead comprising partially double-stranded T7 promoter oligonucleotide adaptors. See, e.g., FIG. 16. The cells are then lysed in a manner that releases template nucleic acid molecules from the nucleus into the aqueous droplet, but that substantially maintains native chromatin organization. Droplets are then generally processed as outlined in FIG. 17.

Figure 18:
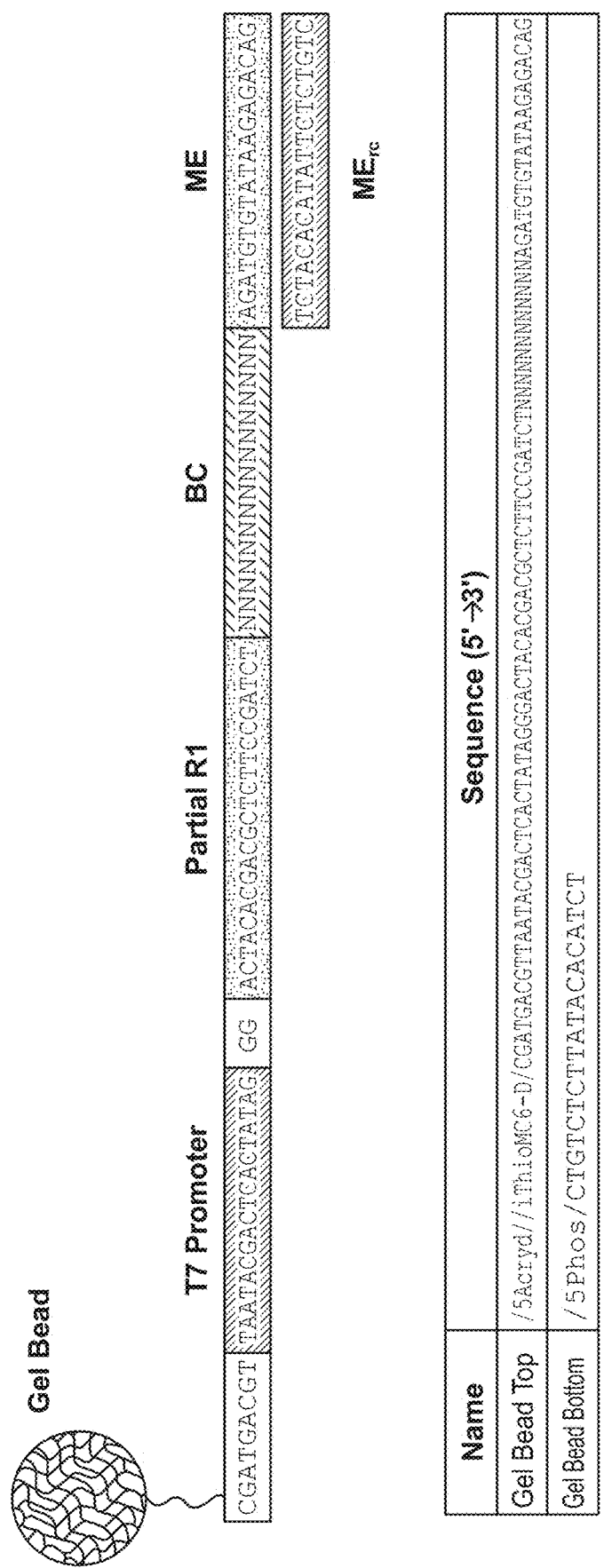
FIG. 18 illustrates an exemplary T7-containing barcoded adaptor.

Specifically, a droplet is subjected to conditions such that the partially double-stranded adaptors are released from the gel bead into the aqueous droplet (e.g., by gel bead depolymerization using a reducing agent, such as DTT). See FIG. 17, step 1. Although the partially double-stranded adaptors can be prepared in a variety of different configurations, an exemplary partially double-stranded adaptor is illustrated in FIG. 18 and shows a partially double-stranded oligonucleotide comprising a first oligonucleotide strand releasably attached to a gel bead and a second, shorter complementary oligonucleotide strand. With continued reference to FIG. 18, the first strand comprises a transposon end ("mosaic end" or "ME") sequence, a barcode sequence ("BC"), a partial sequencing primer sequence ("pR1" or "Partial R1"), and a T7 promoter sequence while the second oligonucleotide strand comprises a sequence fully complementary to the transposon end sequence.

After the partially double-stranded adaptors are released from the gel bead, a droplet is then subjected to conditions such that a transposase-nucleic acid complex is formed comprising a transposase molecule and two partially double-stranded oligonucleotides adaptors. See FIG. 17, step 2. The droplets are then subjected to conditions such that the transposase-nucleic acid complexes integrate the adaptors into the template nucleic acid and produce double-stranded template nucleic acid fragments flanked by the partially double-stranded adaptors. See FIG. 17, step 3. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

The fragmented double-stranded template nucleic acid fragments are then collected from the droplets and processed in bulk to fill any gaps created from the transposition reaction. RNA is generated from the double-stranded template nucleic acid fragments using an in vitro transcription reaction and T7 RNA polymerase. RNA is collected and purified, followed by first and second strand cDNA synthesis. Double-stranded cDNA molecules are then further processed (including fragmentation and adaptor insertion by, e.g., a second transposase-mediated fragmentation) to generate a library suitable for next generation high throughput sequencing (e.g., subjecting the fragments, or derivatives thereof, to one or more reactions (e.g., nucleic acid amplification) to add functional sequences to facilitate Illumina sequencing). The fully constructed library is then sequenced according to any suitable sequencing protocol.

Example 4. Generation of Barcoded Nucleic Acid Fragments from Single Cells Using Transposition of Sequencing Adaptors Followed by Random Priming and Extension A plurality of transposase molecules, a plurality of cells of interest (or a plurality of nuclei harvested from cells of interest), and a plurality of barcode oligonucleotides are partitioned such that at least some partitions comprise a plurality of transposase molecules, a single cell (or nucleus), and a plurality of barcode oligonucleotides comprising a sequencing primer sequence, a barcode sequence, and a transposon end sequence. In some embodiments, the plurality of barcode oligonucleotides are attached to a gel bead and partitioned such that at least some partitions comprise transposase molecules, a single cell (or nucleus), and a single gel bead.

Figure 19:
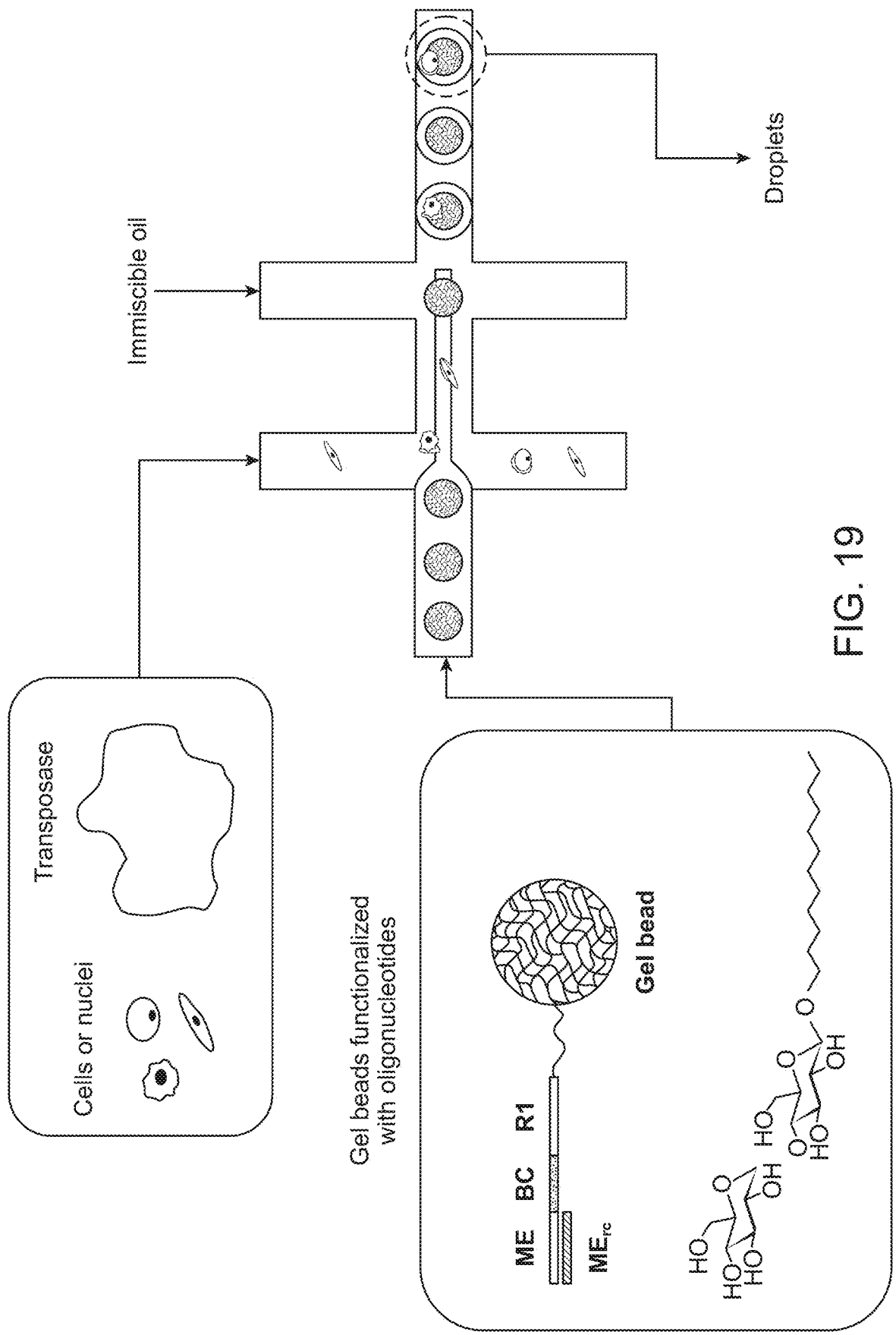
FIG. 19 illustrates an exemplary method to produce droplets wherein at least some of the droplets formed will comprise transposase molecules, a single cell, and a single gel bead comprising a barcoded adaptor.
Figure 20:
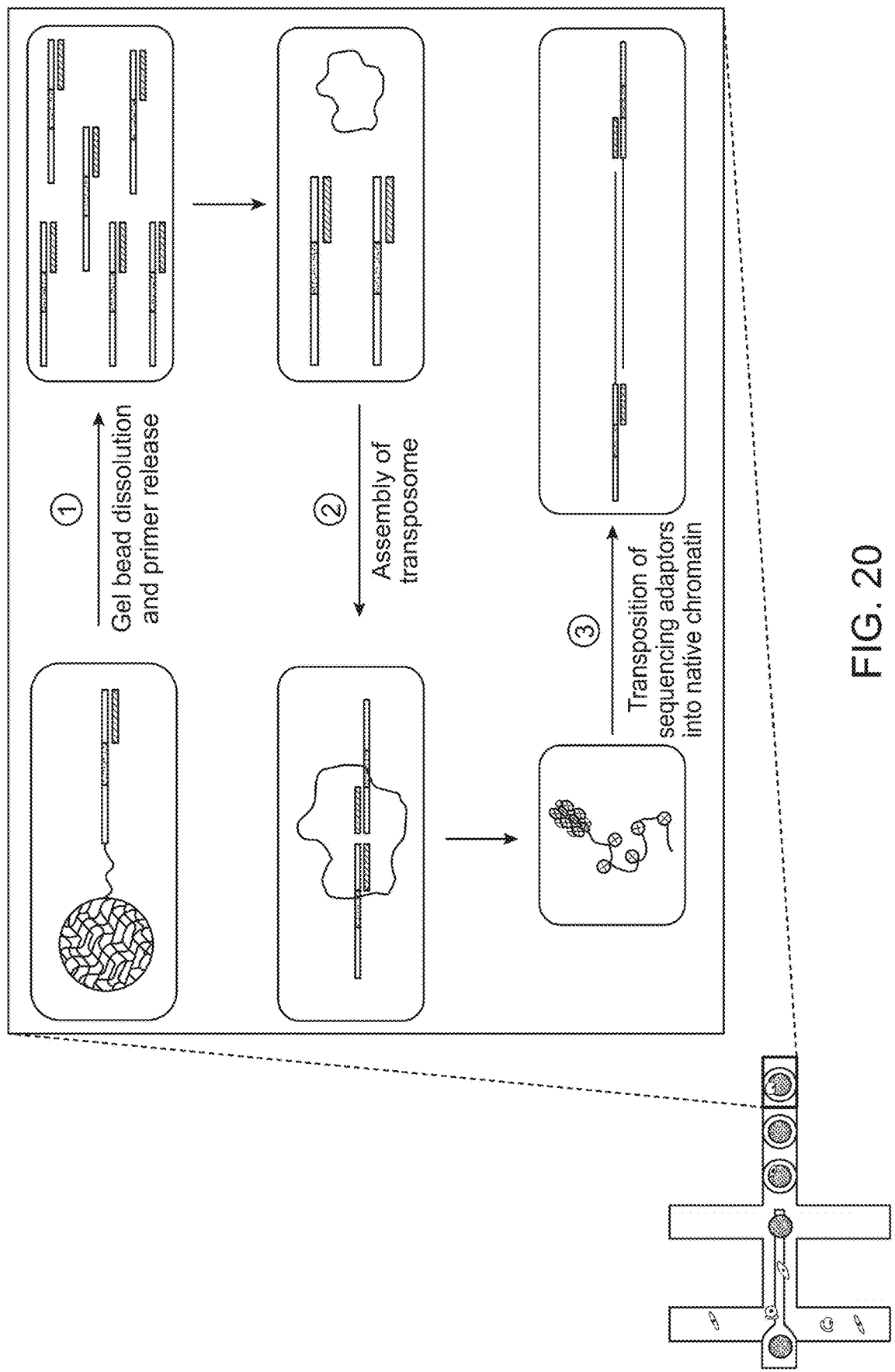
FIG. 20 illustrates an exemplary scheme for producing barcoded, adapter-flanked nucleic acid fragments.

For example, in some embodiments, droplet emulsion partitions are generated as previously described such that at least some droplets that comprise transposase molecules, cell lysis reagents, a single cell, and a single gel bead comprising partially double-stranded barcoded oligonucleotide adaptors. See, e.g., FIG. 19. The cells are then lysed in a manner that releases template nucleic acid molecules from the nucleus into the aqueous droplet, but that substantially maintains native chromatin organization. Droplets are then generally processed as outlined in FIG. 20.

Figure 21:
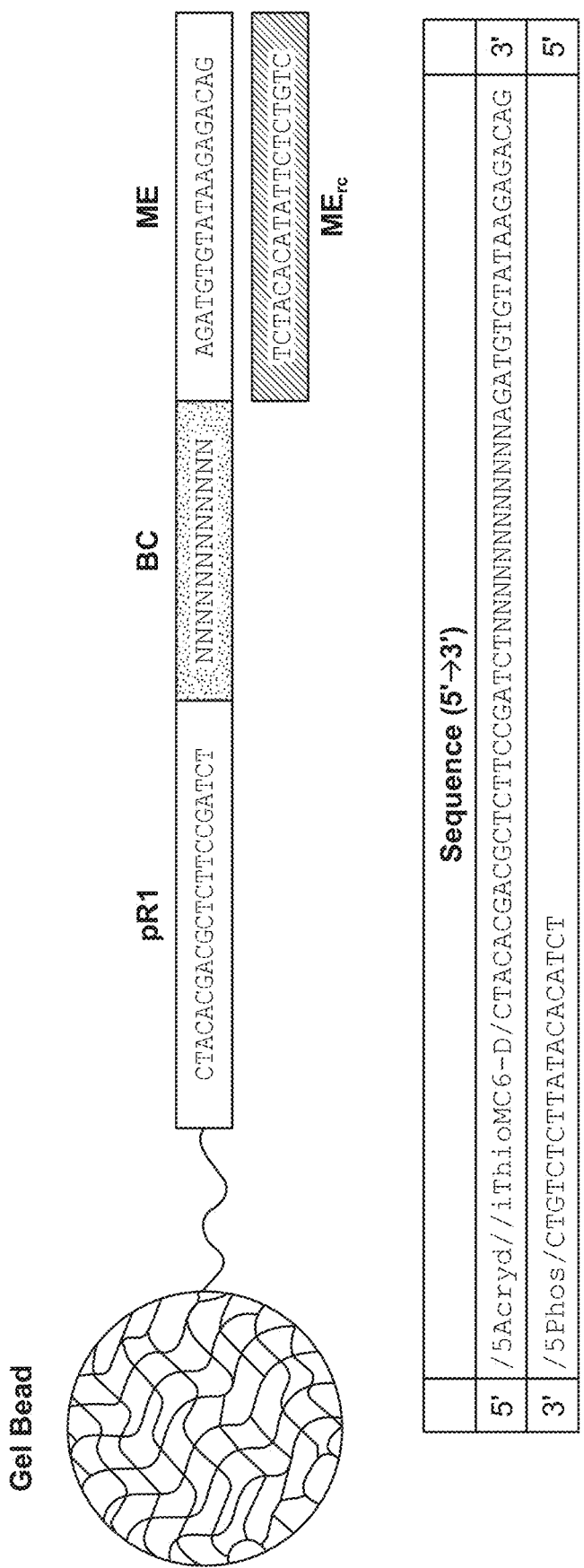
FIG. 21 illustrates an exemplary partially double-stranded barcode oligonucleotide releasably attached to a gel bead.

Specifically, a droplet is subjected to conditions such that the partially double-stranded adaptors are released from the gel bead into the aqueous droplet (e.g., by gel bead depolymerization using a reducing agent, such as DTT). See FIG. 20, step 1. Although the partially double-stranded adaptors can be prepared in a variety of different configurations, an exemplary partially double-stranded adaptor is illustrated in FIG. 21 and shows a partially double-stranded oligonucleotide comprising a first oligonucleotide strand releasably attached to a gel bead and a second, shorter complementary oligonucleotide strand. With continued reference to FIG. 21, the first strand comprises a transposon end ("mosaic end" or "ME") sequence, a barcode sequence ("BC"), and a partial sequencing primer sequence ("pR1" or "Partial R1") while the second oligonucleotide strand comprises a sequence fully complementary to the transposon end sequence.

After the partially double-stranded adaptors are released from the gel bead, a droplet is then subjected to conditions such that a transposase-nucleic acid complex is formed comprising a transposase molecule and two partially double-stranded oligonucleotides. See FIG. 20, step 2. The droplets are then subjected to conditions such that the transposase-nucleic acid complexes integrate the adaptors into the template nucleic acid and produce double-stranded template nucleic acid fragments flanked by the partially double-stranded adaptors. See FIG. 20, step 3. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

Figure 22:
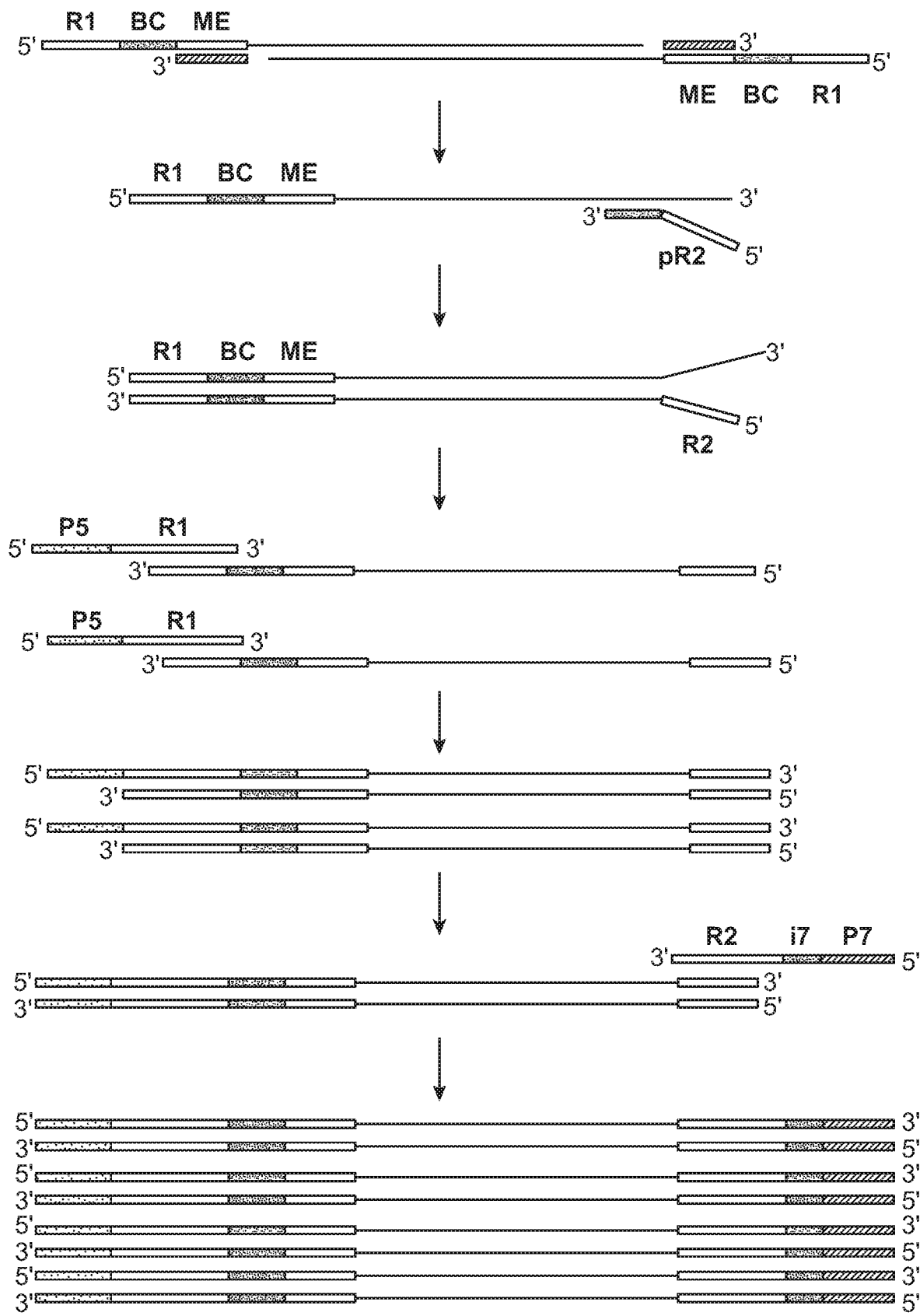
FIG. 22 illustrates a random priming extension reaction scheme.

The fragmented double-stranded template nucleic acid fragments are then collected from the droplets and processed in bulk to generate a library suitable for next generation high throughput sequencing. In some embodiments, for example, double-stranded template nucleic acid fragments are processed in bulk in a random priming extension reaction. See, e,g, FIG. 22. The random extension primer has a sequence of random nucleotides (N-mer) and, for example, can be attached to second PCR handle (e.g., partial R2 sequence, see FIG. 22). The random extension primers are annealed to the double-stranded template nucleic acid fragments, or derivatives thereof, and extended (e.g., FIG. 22). Reactions can then be cleaned-up and extension products subjected to one or more reactions (e.g., nucleic acid amplification) to add functional sequences to facilitate Illumina sequencing (e.g., FIG. 22). The fully constructed library is then sequenced according to any suitable sequencing protocol.

Example 5. Generation of Barcoded Nucleic Acid Fragments from Single Cells Using Transposase-Nucleic Acid Complexes and Barcoded Adaptors In some embodiments, artificial transposons are designed to insert sequences of interest into a target DNA molecule (e.g., open chromatin). For example, an artificial transposon oligonucleotide comprising a barcode sequence and an adapter sequence is flanked by a transposon end sequence on each end of the oligonucleotide (see, e.g., FIG. 23). A plurality of transposase molecules, a plurality of cells of interest (or a plurality of nuclei harvested from cells of interest), and a plurality of artificial transposon oligonucleotides are partitioned such that at least some partitions comprise a plurality of artificial transposon oligonucleotides, a plurality of transposase molecules, and a single cell (or nucleus). In some embodiments, the plurality of artificial transposon oligonucleotides are attached to a gel bead and partitioned such that at least some partitions comprise a plurality of transposase molecules, a single cell (or nucleus), and a single gel bead. In other embodiments, a plurality of transposon nucleic acid complexes comprising an artificial transposon oligonucleotide comprising a barcode sequence and an adapter sequence flanked by transposon end sequenced are partitioned such that at least some partitions comprise a plurality of transposon nucleic acid complexes and a single cell (or nucleus). In some embodiments, the plurality of artificial transposon oligonucleotides are attached to a gel bead and partitioned such that at least some partitions comprise a single cell (or nucleus) and a single gel bead.

For example, in some embodiments, droplet emulsion partitions are generated as previously described such that at least some droplets that comprise transposase molecules, cell lysis reagents, a single cell, and a single gel bead. The cells are then lysed to release template nucleic acid molecules from the nucleus into the aqueous droplet. Droplets are then generally processed as outlined in FIG. 23.

Figure 23:
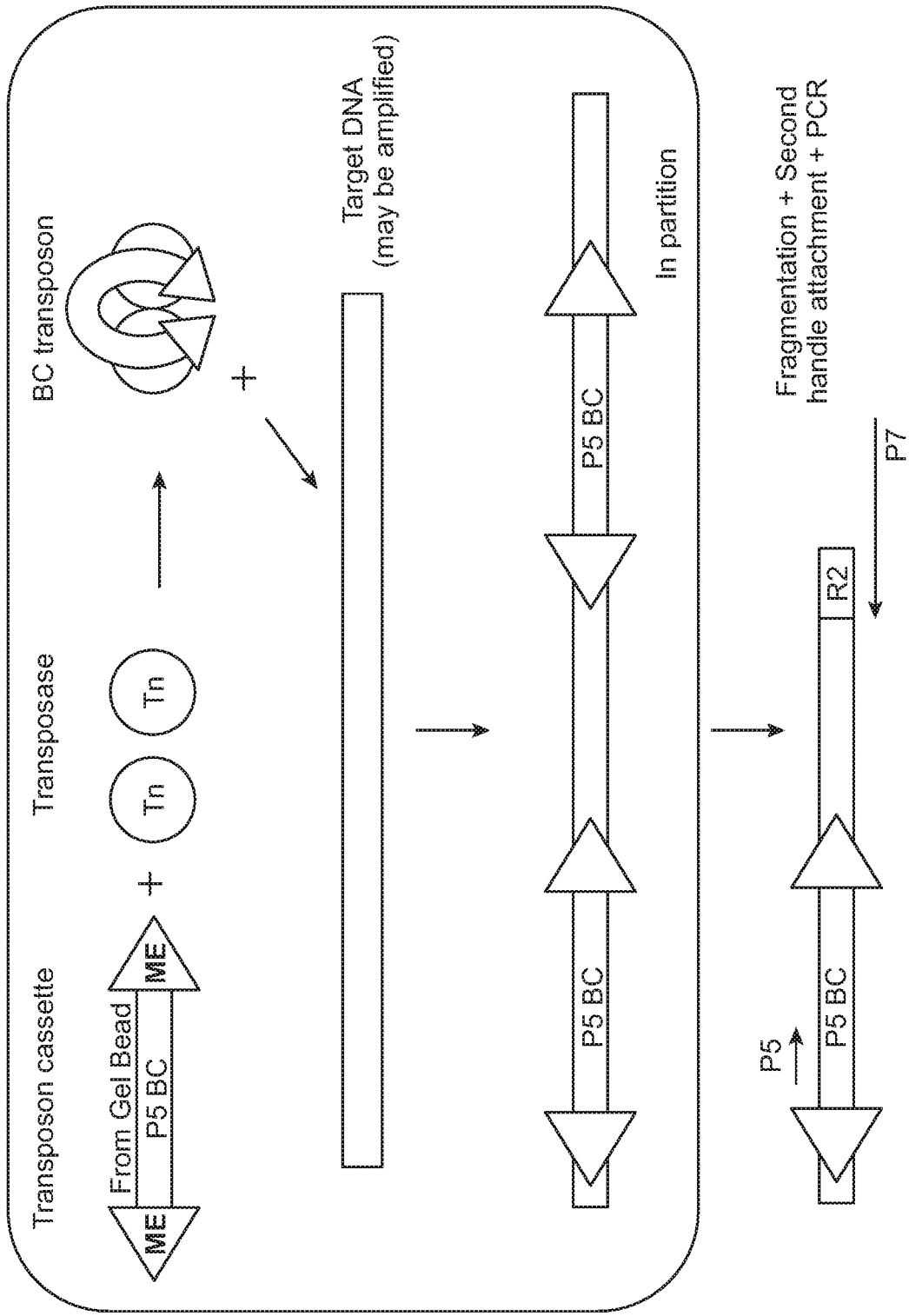
FIG. 23 illustrates an exemplary method of inserting barcodes into a template nucleic acid.

Specifically, a droplet is subjected to conditions such that the barcoded adaptors are released from the gel bead into the aqueous droplet (e.g., by gel bead depolymerization using a reducing agent, such as DTT). Although the barcoded adaptors can be prepared in a variety of different configurations, an exemplary barcoded adaptor is illustrated in FIG. 23 and is a double-stranded oligonucleotide releasably attached to a gel bead, wherein the barcoded adaptor comprises a pair of transposon end ("mosaic end" or "ME") sequences flanking a barcode sequence ("BC") and an adaptor sequence ("P5").

After the barcoded adaptors are released from the gel bead, a droplet is then subjected to conditions such that a transposase-nucleic acid complex is formed comprising a transposase molecule and a barcoded adaptor comprising a pair of transposon end sequences. See FIG. 23. The droplets are then subjected to conditions such that the transposase-nucleic acid complexes integrate the barcoded adaptors into the template nucleic acid. See FIG. 23. In alternative embodiments, cells (or nuclei) are permeabilized/permeable and the transposase-nucleic acid complexes enter the nucleus to perform the transposition reaction. Cells are then lysed to release the transposon-containing template nucleic acid fragments.

The barcode-transposed template nucleic acids are then collected from the droplets and processed in bulk to fragment the barcode-transposed template nucleic acids and to generate a library suitable for next generation high throughput sequencing (e.g., subjecting the fragments, or derivatives thereof, to one or more reactions (e.g., nucleic acid amplification) to add functional sequences to facilitate Illumina sequencing). The fully constructed library is then sequenced according to any suitable sequencing protocol.

Example 6. Generation of Barcoded Nucleic Acid Fragments from Single Cells Using Gel Bead-Functionalized Transposase-Nucleic Acid Complexes A plurality of transposase nucleic acid complexes and a plurality of cells of interest (or a plurality of nuclei harvested from cells of interest) are partitioned such that at least some partitions comprise a single cell (or nucleus) and a plurality of transposase nucleic acid complexes comprising a transposase molecule and a barcode oligonucleotide comprising a sequencing primer sequence, a barcode sequence, and a transposon end sequence (see, e.g., FIGS. 24A-B and 25A-B). In some embodiments, the plurality of transposase nucleic acid complexes are attached to a gel bead (see, e.g., FIGS. 24A-B and 26) and partitioned such that at least some partitions comprise a single cell (or nucleus) and a single gel bead.

For example, in some embodiments, droplet emulsion partitions are generated as previously described such that at least some droplets comprise cell lysis reagents, a single cell, and a single gel bead functionalized with a transposase-nucleic acid complex. The cells are then lysed in a manner that releases template nucleic acid molecules from the nucleus into the aqueous droplet, but that substantially maintains native chromatin organization.

Figure 24A:
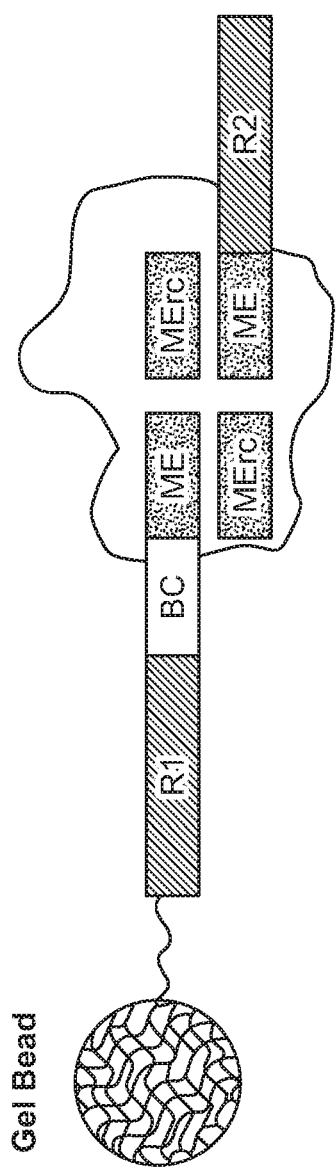
FIGS. 24A-B illustrate an exemplary transposase-nucleic acid complex showing a transposase, a first partially double-stranded oligonucleotide releasably attached to a gel bead, the first partially double-stranded oligonucleotide comprising a transposon end sequence, a barcode sequence, and a first primer sequence and a second partially double-stranded oligonucleotide comprising a transposon end sequence and a second primer sequence.
Figure 24B:
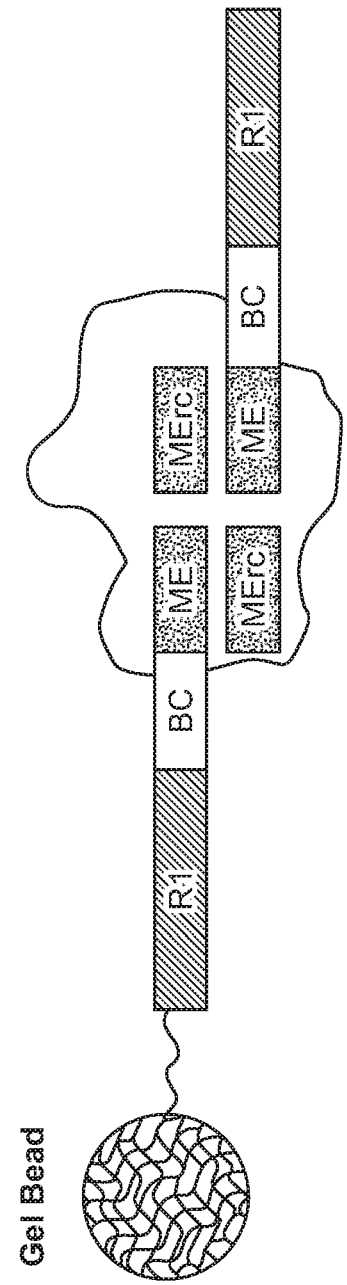
Figure 25A:
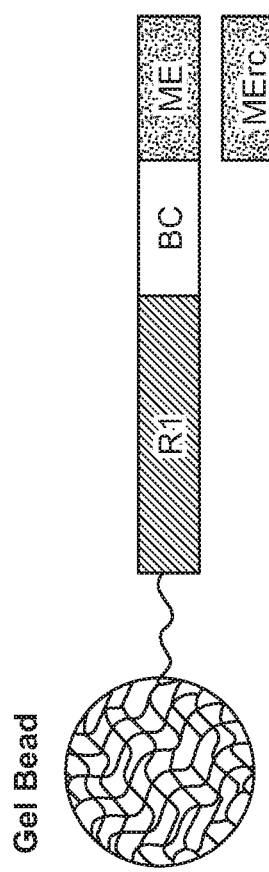
FIGS. 25A-B illustrates an exemplary barcode oligonucleotides.
Figure 25B:
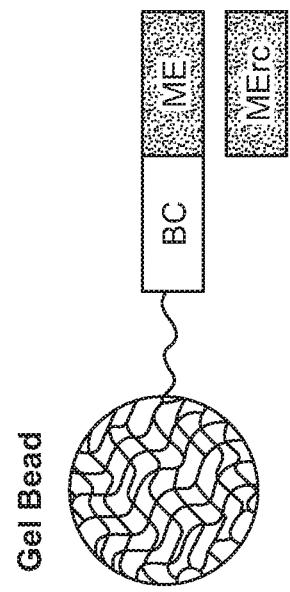

Droplets are then subjected to conditions such that the transposase-nucleic acid complexes are released from the gel bead into the aqueous droplet (e.g., by gel bead depolymerization using a reducing agent, such as DTT). Although the transposase-nucleic acid complexes can be prepared in a variety of different configurations, a transposase-nucleic acid complex is illustrated in FIG. 24A and shows a complex comprising a transposase, a first partially double-stranded oligonucleotide, and a second partially double-stranded oligonucleotide. Continuing with the embodiment of FIG. 24A, the first partially double-stranded oligonucleotide comprises: (a) a first strand releasably attached to a gel bead, wherein the first strand comprises a transposon end sequence ("ME"), a barcode sequence ("BC"), and a first sequencing primer sequence ("R1"); and (b) a second strand complementary to the transposon end sequence of the first oligonucleotide strand. With continued reference to FIG. 24A, the second partially double-stranded oligonucleotide comprises: (a) a first oligonucleotide strand comprising a transposon end sequence ("ME") and a second primer sequence ("R2"); and (b) a second strand complementary to the transposon end sequence. See also FIG. 24B, which comprises an identical first partially double-stranded oligonucleotide as the above described embodiment and a second partially double-stranded oligonucleotide comprising: (a) a first oligonucleotide strand comprising a transposon end sequence ("ME"), a barcode sequence ("BC"), and the first primer sequence ("R1"); and (b) a second strand complementary to the transposon end sequence of the second oligonucleotide strand.

Figure 26:
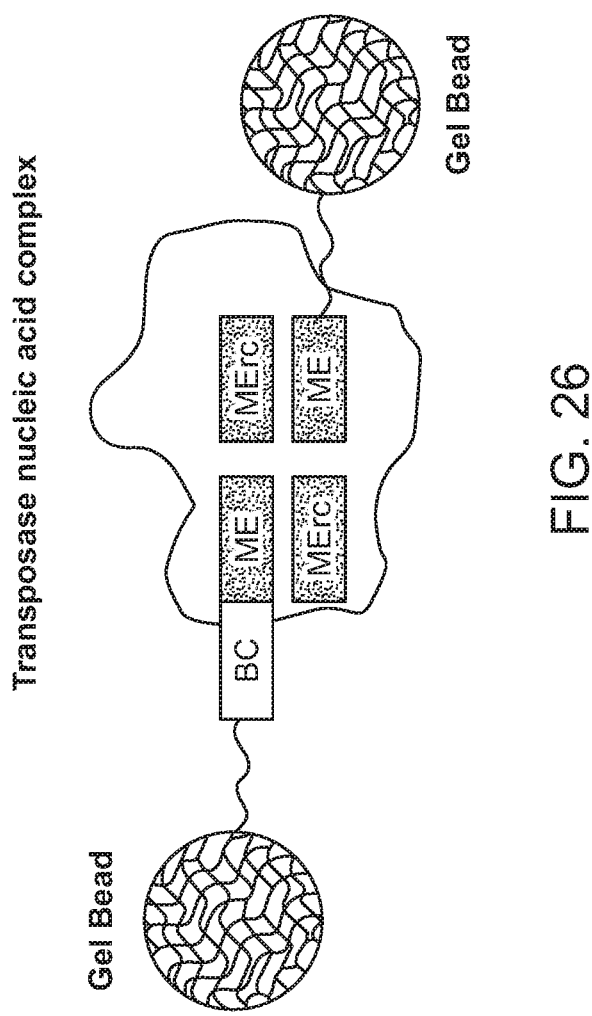
FIG. 26 illustrates an exemplary transposase-nucleic acid complex showing a transposase, a first double-stranded oligonucleotide comprising a barcode sequence and a transposon end sequence releasably attached to a first gel bead and a second double-stranded oligonucleotide comprising a transposon end sequence releasably attached to a second gel bead.

Alternatively, gel-bead functionalized transposase-nucleic acid complexes are prepared as illustrated in FIG. 26, which shows a complex comprising a transposase, a first partially double-stranded oligonucleotide and a second double-stranded oligonucleotide. In this embodiment, the first partially double-stranded oligonucleotide comprises: (a) a first strand releasably attached to a gel bead, wherein the first strand comprises a transposon end sequence ("ME") and a barcode sequence ("BC") and (b) a second strand complementary to the transposon end sequence of the first oligonucleotide strand while the second double-stranded oligonucleotide comprises: (a) a first strand releasably attached to a gel bead, wherein the first strand comprises a transposon end sequence ("ME) and (b) a second strand complementary to the first oligonucleotide strand. Alternative embodiments of FIG. 26 comprise additional functional sequences, such as a sequencing primer sequence (e.g., R1 and/or R2) or an adapter sequence (e.g., P5 and/or P7).

In other embodiments, droplets are partitioned such that at least some droplets comprise cell lysis reagents, a plurality of transpose molecules, a single cell, and a single gel bead comprising a barcode oligonucleotide comprising a barcode sequence ("BC") and a transposon end sequence ("ME"). See, e.g., FIGS. 25A-B. Droplets are then subjected to conditions such that transposase nucleic acid complexes comprising a transposase molecule and a barcode oligonucleotide are formed in the partition.

After the transposase-nucleic acid complex is released from the gel bead (or is formed in the partition in embodiments such as FIG. 25A-B), a droplet is then subjected to conditions such that the transposase-nucleic acid complexes integrate the transposon end sequences into the template nucleic acid and fragments the template nucleic acid into double-stranded template nucleic acid fragments flanked by first and second partially double-stranded oligonucleotides. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell.

Figure 27:
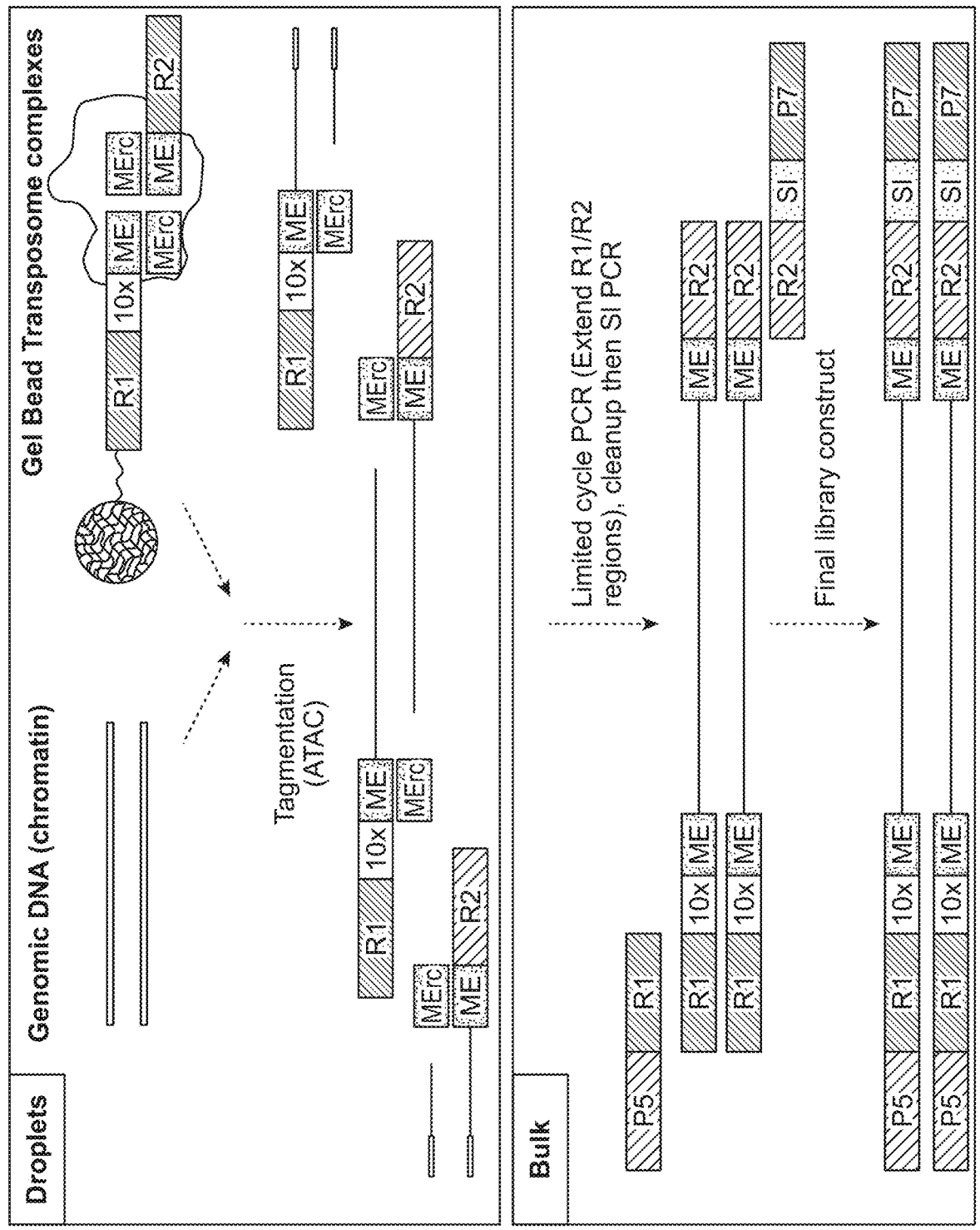
FIG. 27 illustrates an exemplary method to produce barcoded nucleic acid fragments suitable for next generation sequencing.

The fragmented double-stranded template nucleic acid fragments are then collected from the droplets and processed in bulk to fill any gaps created from the transposition reaction and to generate a library suitable for next generation high throughput sequencing (e.g., subjecting the fragments, or derivatives thereof, to one or more reactions (e.g., nucleic acid amplification) to add functional sequences to facilitate Illumina sequencing; see, e.g., FIG. 27). The fully constructed library is then sequenced according to any suitable sequencing protocol.

Example 7. Generation of Barcoded Nucleic Acid Fragments from Single Cells Using Transposase-Nucleic Acid Complexes and Barcoded Adaptors (Two-Step Approach)

Figure 28A:
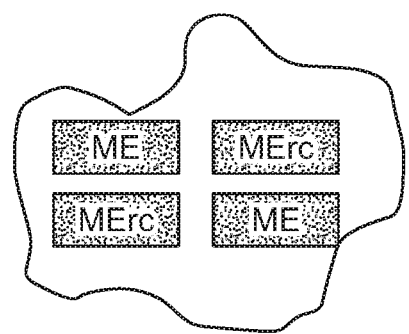
FIGS. 28A-B illustrate an exemplary transposase-nucleic acid complex and an exemplary barcoded adaptor releasably attached to a gel bead.
Figure 28B:
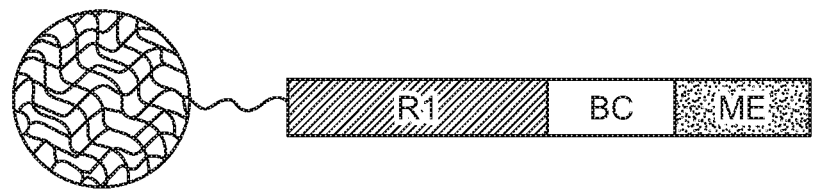

A plurality of transposase nucleic acid complexes and a plurality of cells of interest (or a plurality of nuclei harvested from cells of interest) are partitioned such that at least some partitions comprise a single cell (or nucleus), a plurality of transposase nucleic acid complexes comprising a transposon end sequence, and a plurality of barcoded oligonucleotides comprising a barcode sequence and a sequencing primer sequence (see, e.g., FIGS. 28A-B). In some embodiments, the plurality of barcode oligonucleotides further comprise a transposon end sequence. In some embodiments, the plurality of barcode oligonucleotides are attached to a gel bead (see, e.g., FIG. 28B) and partitioned such that at least some partitions comprise a plurality of transposase nucleic acid complexes, a single cell (or nucleus), and a single gel bead.

For example, in some embodiments, droplet emulsion partitions are generated as previously described such that at least some droplets that comprise a transposase-nucleic acid complex comprising a transposase and a pair of double-stranded oligonucleotides, cell lysis reagents, a single cell, and a single gel bead comprising a barcoded adaptor. Although the transposase-nucleic acid complexes can be prepared in a variety of different configurations, a transposase-nucleic acid complex is illustrated in FIG. 28A and shows a complex comprising a transposase, a first double-stranded oligonucleotide comprising a transposon end ("mosaic end" or "ME") sequence, and a second double-stranded oligonucleotide comprising a transposon end ("mosaic end" or "ME") sequence.

The cells are lysed in a manner that releases template nucleic acid molecules from the nucleus into the aqueous droplet, but that substantially maintains native chromatin organization. Droplets are then subjected to conditions such that the barcoded adaptors are released from the gel bead into the aqueous droplet. Although the barcoded adaptors can be prepared in a variety of different configurations, an exemplary barcoded adaptor is illustrated in FIG. 28B and shows a single-stranded oligonucleotide comprising a transposon end ("mosaic end" or "ME") sequence, a barcode sequence ("BC"), and a primer sequence ("R1") releasably attached to a gel bead.

After the barcoded adaptors are released from the gel bead, a droplet is then subjected to conditions such that the transposase-nucleic acid complexes integrate the transposon end sequences into the template nucleic acid and fragment the template nucleic acid into double-stranded template nucleic acid fragments. In alternative embodiments, cells (or nuclei) are permeabilized/permeable and the transposase-nucleic acid complexes enter the nucleus to fragment the template nucleic acid. Cells are then lysed to release the fragmented double-stranded template nucleic acid fragments. Because the transposase-nucleic acid complex can only act on a nucleosome-free template, the fragmented double-stranded template nucleic acid fragments are representative of genome-wide areas of accessible chromatin in a single cell. After transposition and fragmentation, a PCR reaction is performed to fill any gaps created from the transposition reaction and to add the barcoded adaptors to the ends of the fragmented double-stranded template nucleic acid fragments.

The fragmented double-stranded template nucleic acid fragments are then collected from the droplets and processed in bulk to generate a library suitable for next generation high throughput sequencing (e.g., subjecting the fragments, or derivatives thereof, to one or more reactions (e.g., nucleic acid amplification) to add functional sequences to facilitate Illumina sequencing). The fully constructed library is then sequenced according to any suitable sequencing protocol.

Example 8. Generation of Barcoded Nucleic Acid Fragments Using Transposase-Nucleic Acid Complexes Assembled in a Single Reaction Step Traditional tube-based implementations of Tn5-based tagmentation systems typically rely upon sample processing steps that take place in two independent reactions to generate the final transposase-fragmented nucleic acid sample. For example, in Reaction #1, oligonucleotide adaptors containing the Tn5 transposon end sequences and the Tn5 transposase enzyme are incubated to form a transposase-nucleic acid complex. Typically, magnesium (or other divalent cations) are omitted from the reaction buffer to keep the transposases catalytically inactive. In Reaction #2, the transposase-nucleic acid complex from Reaction #1 is combined with a target double-stranded DNA and an appropriate reaction buffer containing magnesium (or other divalent cations) to activate the transposase-nucleic acid complex and cause fragmentation of the target DNA and ligation of the adapter oligonucleotide sequences. While the above-described serial reaction workflow is straightforward, implementing a tagmentation reaction within a single reaction or reaction vessel ("one-pot reaction") can be complicated.

A one-pot transposition reaction was performed on 50,000 HEK293T cells and compared to a traditional two-step tagmentation reaction. Sequencing libraries were prepared from each reaction type and sequenced on an Illumina sequencer. Sequencing data is presented in Table 1 below and demonstrates comparable sequencing metrics between the traditional and one-pot tagmentation methods.

TABLE 1

| Results from One-Pot Sequencing Reactions | | |
|---|---|---|
| Sequencing metrics | Traditional | One-pot |
| Total gb | 43 | 31 |
| Library complexity | 1.1 | 0.52 |
| Median insert size | 160 | 180 |
| Unmapped fraction | 0.014 | 0.034 |
| Non-nuclear read fraction | 0.53 | 0.26 |
| Fraction of fragments on target | 0.57 | 0.81 |
| Mean duplication rate | 1.5 | 1.8 |
| Percent reads gt 10 bp soft clipped | 0.25 | 0.17 |

The transposition methods described herein can be utilized in a one-pot reaction as described above. These one-pot reactions can be done either in bulk or in discrete partitions, such as a well or droplet.

Example 9. Generation of Barcoded Nucleic Acid Fragments Using Bulk Tagmentation and Barcoding by Ligation in Droplets (Variant 1)

Intact nuclei are harvested in bulk from cells in a cell population of interest in a manner that substantially maintains native chromatin organization (e.g., using IGEPAL CA-630 mediated cell lysis). Nuclei are then incubated in the presence of a transposase-nucleic acid complex comprising a transposase molecule and two partially double-stranded adaptor oligonucleotides. See, e.g., FIG. 29A. Alternatively, cells are permeabilized, allowing the transposase-nucleic acid complex to gain access to the nucleus. The first adapter oligonucleotide comprises a double stranded transposon end sequence (ME) and a single stranded Read1 sequencing primer sequence (R1) while the second adapter oligonucleotide comprises a double stranded transposon end sequence (ME) and a single stranded Read2 sequencing primer sequence (R2). See FIG. 29A. In some embodiments, the R1 and/or R2 sequencing primer in the first and/or second adapter oligonucleotide comprises a TruSeq R1 and/or R2 sequence, or a portion thereof. The transposase-nucleic acid complexes integrate the adaptors into the template nucleic acid and produce template nucleic acid fragments flanked by the partially double-stranded adaptors. See FIG. 29C. Because the transposase-nucleic acid complex can only act on a nucleosome-free template, the fragmented template nucleic acid fragments are representative of genome-wide areas of accessible chromatin. In some embodiments, the transposase molecules are inactivated prior to further processing steps.

Nuclei (or cells) comprising the adapter-flanked template nucleic acid fragments are then partitioned into a plurality of droplets such that at least some droplets comprise (1) a single nucleus (or cell) comprising the adapter-flanked template nucleic acid fragments; and (2) a plurality of partially double-stranded barcode oligonucleotide molecules comprising a doubled stranded barcode sequence (BC), a doubled stranded P5 adapter sequence (P5), and a single stranded sequence complementary to the Read 1 sequence (R1rc). See FIG. 29B. In some embodiments, the partially double-stranded barcode oligonucleotide molecules are attached to a gel bead and partitioned such that at least some droplets comprise (1) a single nucleus (or cell) and (2) a single gel bead. In addition to the aforementioned components, in some embodiments, the plurality of droplets further comprises reagents (e.g., enzymes and buffers) that facilitate the reactions described below.

Single nucleus containing droplets are then subjected to conditions to release the adapter-flanked template nucleic acid fragments from the nuclei (e.g., cell lysis). In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). After release from single nuclei, the adapter-flanked template nucleic acid fragments are subjected to conditions to phosphorylate the 5' end of the Read1 sequence (e.g., using T4 polynucleotide kinase) for subsequent ligation steps. After phosphorylation, the barcode oligonucleotide molecules are ligated onto the adapter-flanked template nucleic acid fragments using a suitable DNA ligase enzyme (e.g., T4 or *E. coli* DNA ligase) and the complementary Read1 sequences in the barcode oligonucleotides and the adapter-flanked template nucleic acid fragments. See FIG. 29C.

After barcode ligation, gaps remaining from the transposition reaction are filled to produce barcoded, adapter-flanked template nucleic acid fragments. See FIG. 29C. The barcoded, adapter-flanked template nucleic acid fragments are then released from the droplets and processed in bulk to complete library preparation for next generation high throughput sequencing (e.g., to add sample index (SI) sequences (e.g., i7) and/or further adapter sequences (e.g., P7)). In alternative embodiments, the gap filling reaction is completed in bulk after barcoded, adapter-flanked template nucleic acid fragments have been released from the droplets. The fully constructed library is then sequenced according to a suitable next-generation sequencing protocol (e.g., Illumina sequencing).

Example 10. Generation of Barcoded Nucleic Acid Fragments Using Tagmentation and Barcoding by Ligation in Droplets Cells from a cell population of interest (or nuclei from cells in a cell population of interest) are partitioned into a plurality of droplets such that at least some droplets comprise (1) a single cell (or a single nucleus) comprising a template nucleic acid; and (2) a plurality of partially double-stranded barcode oligonucleotide molecules comprising a doubled stranded barcode sequence (BC), a doubled stranded P5 adapter sequence (P5), and a single stranded sequence complementary to a Read 1 sequence (R1rc) (e.g., FIG. 29B). In some embodiments, the partially double-stranded barcode oligonucleotide molecules are attached to a gel bead and partitioned such that at least some droplets comprise (1) a single cell (or a single nucleus) and (2) a single gel bead. In addition to the aforementioned components, in some embodiments, the plurality of droplets further comprises reagents (e.g., enzymes and buffers) that facilitate the reactions described below.

Figure 29A:
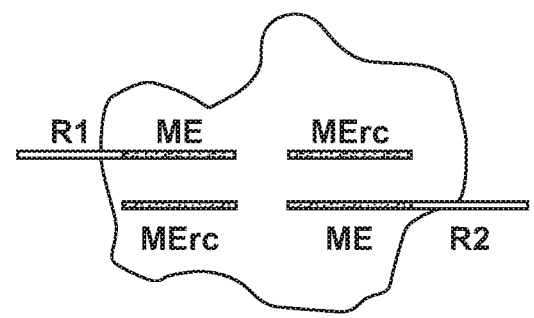
FIGS. 29A-D illustrate an exemplary transposase-nucleic acid complex and an exemplary barcoded adaptor, which can be releasably attached to a gel bead.
Figure 29B:
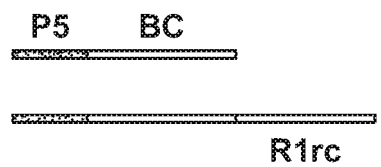
Figure 29C:
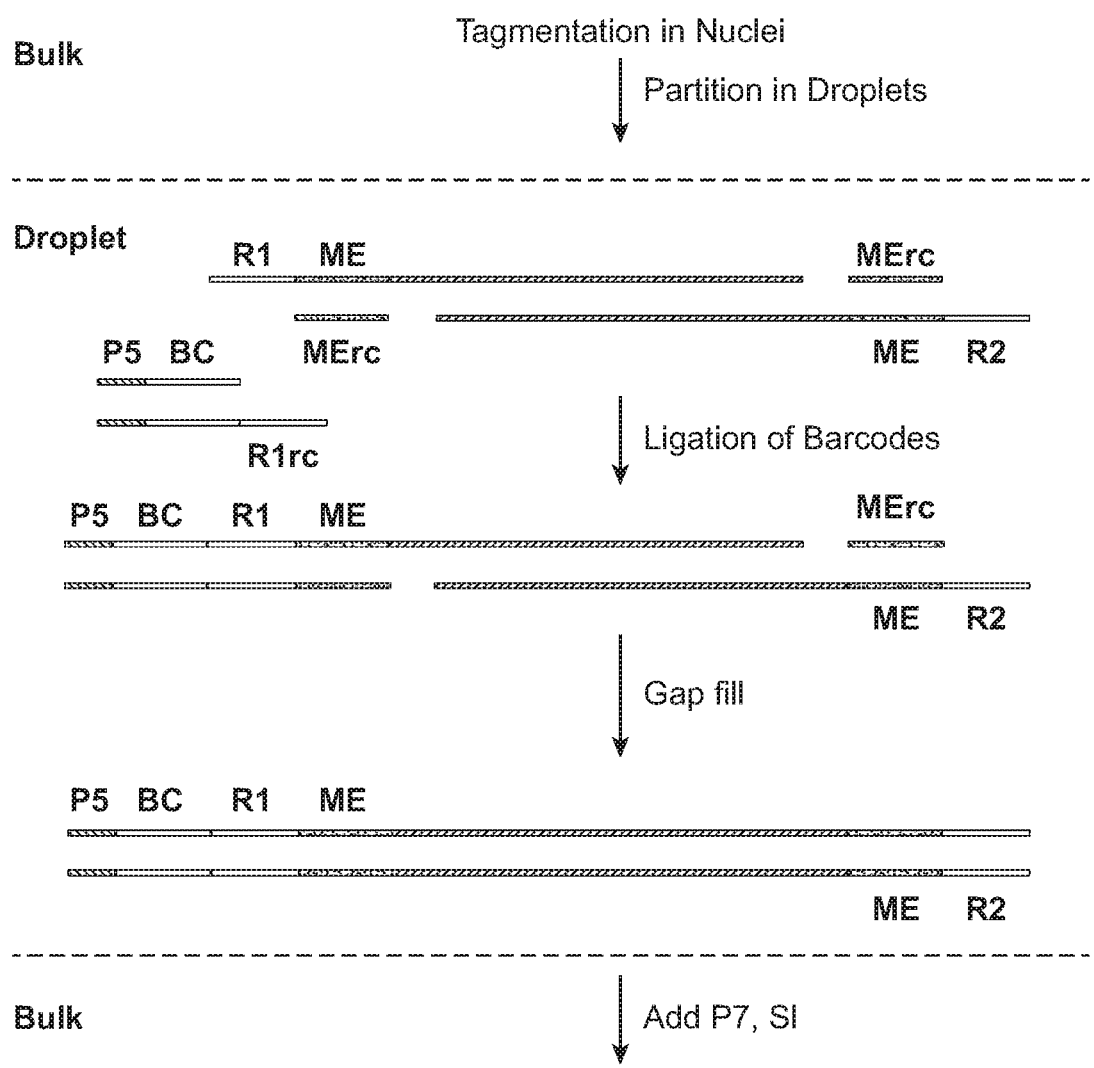
Figure 29D:
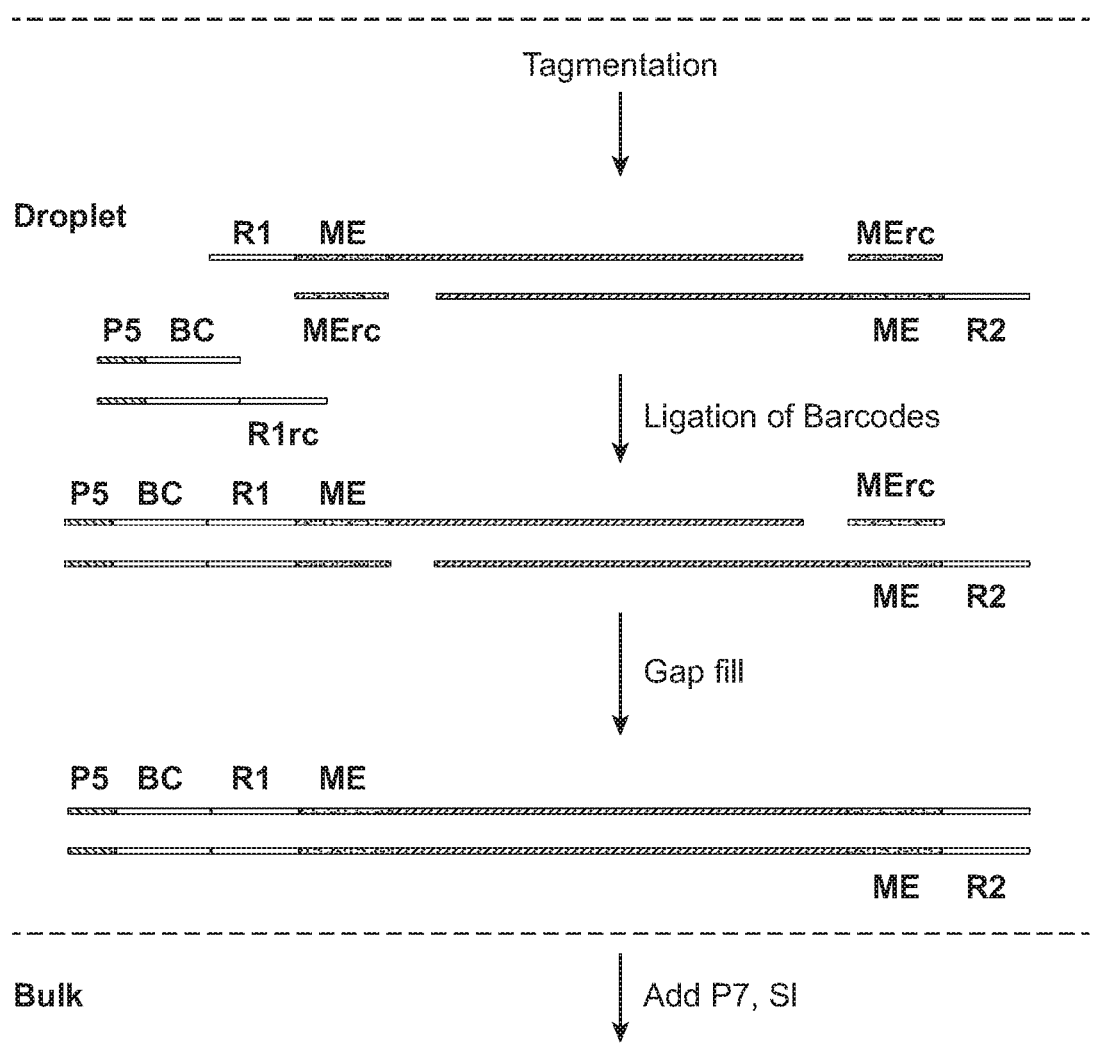

After partitioning into droplets, the single cells (or nuclei) are lysed to release the template genomic DNA in a manner that substantially maintains native chromatin organization. Droplets are then subjected to conditions to generate a transposase-nucleic acid complex as described in Example 9 and shown in FIG. 29A. Alternatively, in some embodiments, a plurality of pre-formed transposase-nucleic acid complexes as shown in FIG. 29A are partitioned into the plurality of droplets. Droplets are then subjected to conditions such that the transposase-nucleic acid complexes integrate the first and second adapter sequences into the template nucleic acid to generate double-stranded adapter-flanked template nucleic acid fragments. See FIG. 29D. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed after transposition to release the double-stranded adapter-flanked template nucleic acid fragments.

Samples are then processed generally as described in Example 9. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). In some embodiments, the transposase molecules are inactivated (e.g., by heat inactivation) prior to further processing steps. The adapter-flanked template nucleic acid fragments are subjected to conditions to phosphorylate the 5' end of the Read1 sequence (e.g., using T4 polynucleotide kinase) of the adapter-flanked template nucleic acid fragments. After phosphorylation, the barcode oligonucleotide molecules are ligated onto the adapter-flanked template nucleic acid fragments using a suitable DNA ligase enzyme (e.g., T4, 9° N, or *E. coli* DNA ligase) and the complementary Read1 sequences in the barcode oligonucleotides and the adapter-flanked template nucleic acid fragments. See FIG. 29C.

After barcode ligation, gaps remaining from the transposition reaction are filled to produce barcoded, adapter-flanked template nucleic acid fragments. See FIG. 29C. The barcoded, adapter-flanked template nucleic acid fragments are then released from the droplets and processed in bulk to complete library preparation for next generation high throughput sequencing (e.g., to add sample index (SI) sequences (e.g., i7) and/or further adapter sequences (e.g., P7)). In alternative embodiments, the gap filling reaction is completed in bulk after barcoded, adapter-flanked template nucleic acid fragments have been released from the droplets. The fully constructed library is then sequenced according to a suitable next-generation sequencing protocol (e.g., Illumina sequencing).

Example 11. Generation of Barcoded Nucleic Acid Fragments Using Bulk Tagmentation and Barcoding by Linear Amplification in Droplets Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei (or permeabilized cells) are then incubated in the presence of a transposase-nucleic acid complex as described in Example 9. See FIG. 29A.

Figures 30A, 30B:
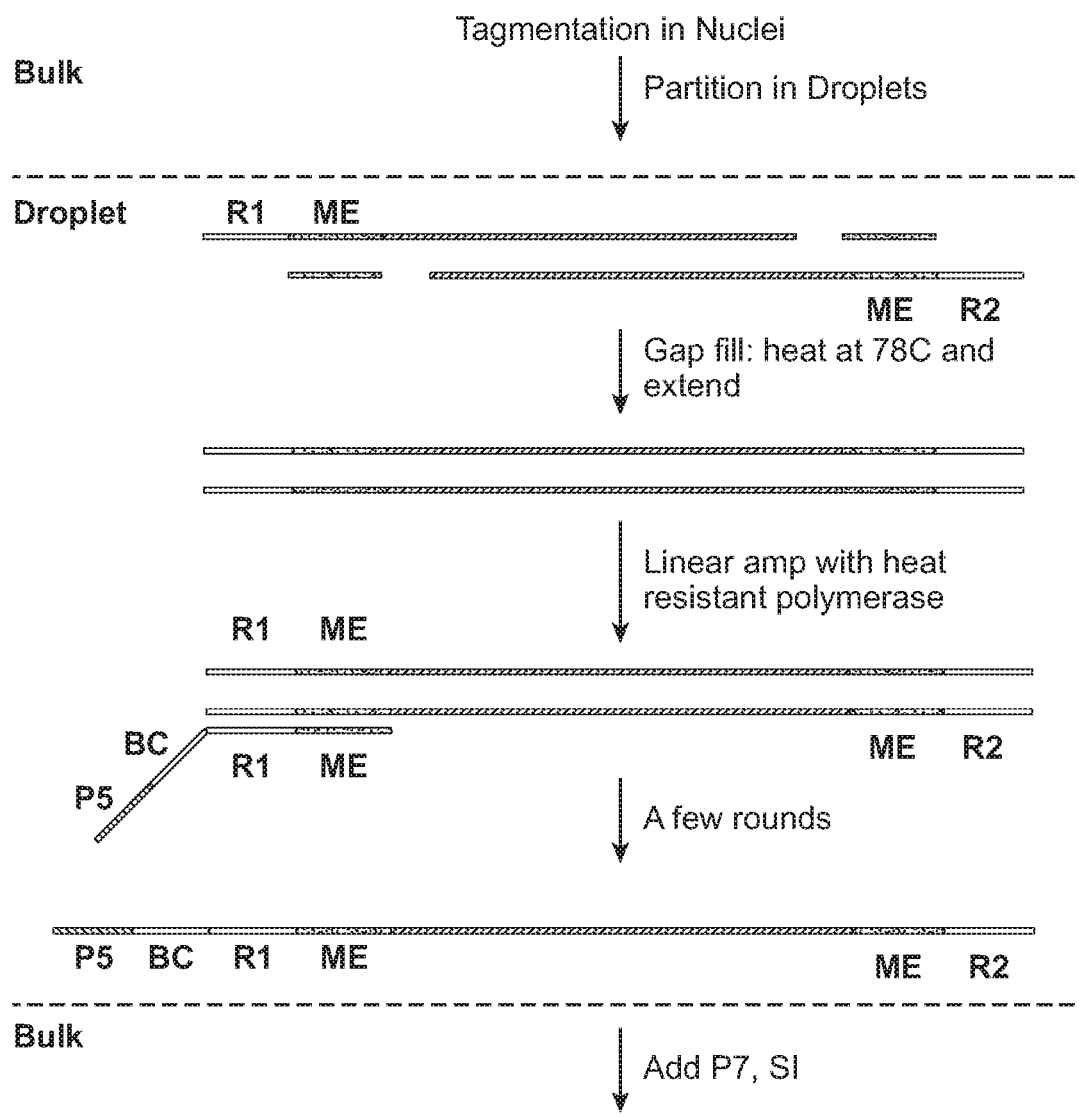
FIGS. 30A-B illustrate an exemplary barcode oligonucleotide (FIG. 30A) and combination bulk/in-partition barcoding scheme (FIG. 30B).

Nuclei (or cells) comprising the adapter-flanked template nucleic acid fragments are then partitioned into a plurality of droplets such that at least some droplets comprise (1) a single nucleus (or cell) comprising the adapter-flanked template nucleic acid fragments; and (2) a plurality of single-stranded barcode oligonucleotide molecules comprising a transposon end sequence (ME), a Read1 sequence (R1), or a portion thereof, a barcode sequence (BC), and a P5 adapter sequence (P5). See FIG. 30A. In some embodiments, the single-stranded barcode oligonucleotide molecules are attached to a gel bead and partitioned such that at least some droplets comprise (1) a single nucleus (or cell) comprising the adapter-flanked template nucleic acid fragments and (2) a single gel bead. In addition to the aforementioned components, in some embodiments, the plurality of droplets further comprises reagents (e.g., enzymes and buffers) that facilitate the reactions described below.

Single nucleus containing droplets are then subjected to conditions to release the adapter-flanked template nucleic acid fragments from the nuclei. After the adapter-flanked template nucleic acid fragments are released, gaps from the transposition reaction are filled with a suitable enzyme. See FIG. 30B. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). Gap-filled adapter-flanked template nucleic acid fragments are then subjected to a linear amplification reaction using the single-stranded barcode oligonucleotide molecules as primers to produce barcoded, adapter-flanked template nucleic acid fragments. See FIG. 30B.

The barcoded, adapter-flanked template nucleic acid fragments are then released from the droplets and processed in bulk to complete library preparation for next generation high throughput sequencing (e.g., to add sample index (SI) sequences (e.g., i7) and/or further adapter sequences (e.g., P7)). The fully constructed library is then sequenced according to a suitable next-generation sequencing protocol (e.g., Illumina sequencing).

Example 12. Generation of Barcoded Nucleic Acid Fragments Using Tagmentation and Barcoding by Linear Amplification in Droplets Cells from a cell population of interest (or intact nuclei from cells in a cell population of interest) are partitioned into a plurality of droplets such that at least some droplets comprise (1) a single cell (or a single nucleus) comprising a template nucleic acid; and (2) a plurality of single-stranded barcode oligonucleotide molecules comprising a transposon end sequence (ME), a Read1 sequence (R1), a barcode sequence (BC), and a P5 adapter sequence (P5). See, e.g., FIG. 30A. In some embodiments, the single-stranded barcode oligonucleotide molecules are attached to a gel bead and partitioned such that at least some droplets comprise (1) a single cell (or a single nucleus) and (2) a single gel bead. In addition to the aforementioned components, in some embodiments, the plurality of droplets further comprises reagents (e.g., enzymes and buffers) that facilitate the reactions described below.

After partitioning into droplets, the single cells (or nuclei) are lysed to release the template genomic DNA in a manner that substantially maintains native chromatin organization. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). Droplets are then subjected to conditions to generate a transposase-nucleic acid complex as described in Example 9 and shown in FIG. 29A. Alternatively, in some embodiments, a plurality of pre-formed transposase-nucleic acid complexes as shown in FIG. 29A are partitioned into the plurality of droplets. Droplets are then subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Figure 31:
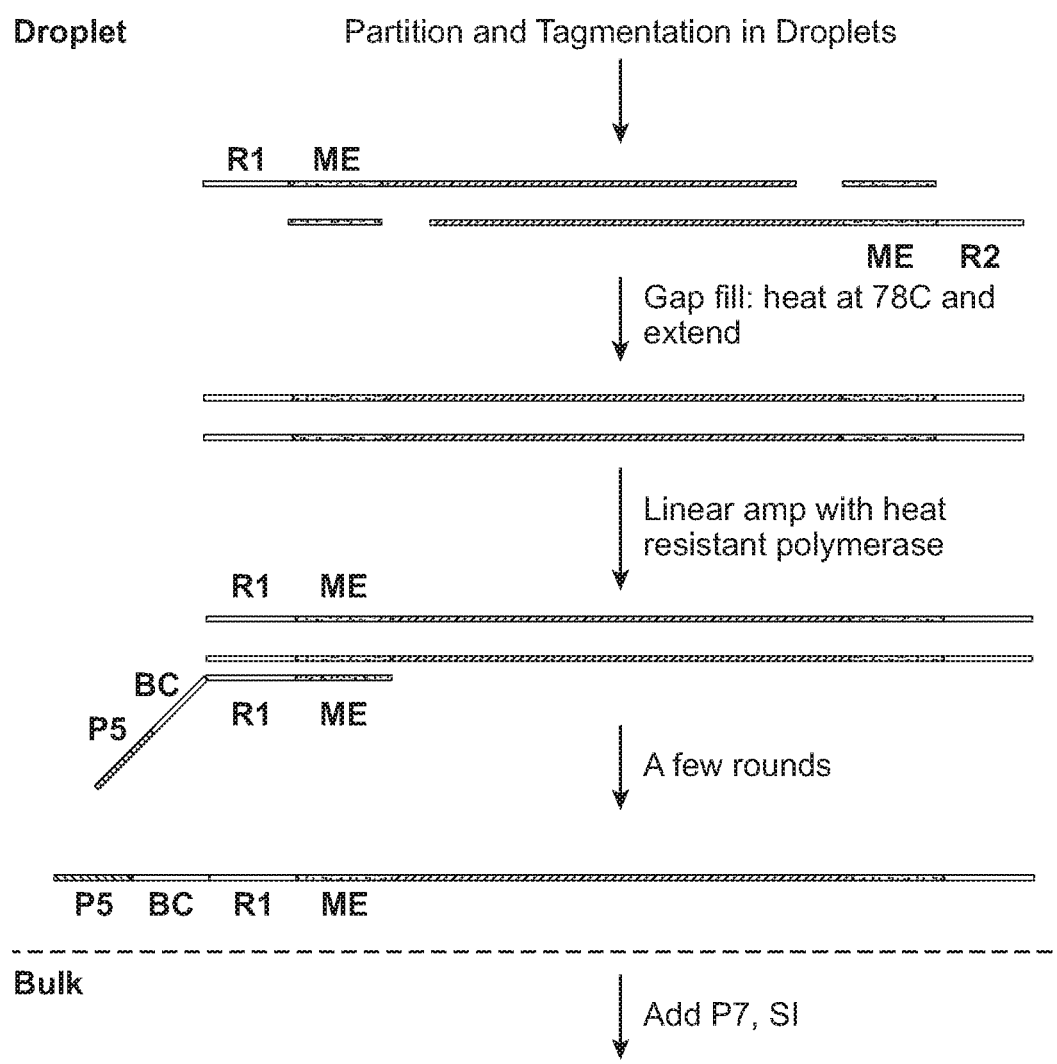
FIG. 31 illustrates an exemplary in-partition transposition and barcoding scheme.

Samples are then processed generally as described in Example 11. After tagmentation, gaps from the transposition reaction are filled with a suitable gap-filling enzyme. See FIG. 31. Gap-filled adapter-flanked template nucleic acid fragments are then subjected to a linear amplification reaction using the single-stranded barcode oligonucleotide molecules as primers to produce barcoded, adapter-flanked template nucleic acid fragments. See FIG. 31.

The barcoded, adapter-flanked template nucleic acid fragments are then released from the droplets and processed in bulk to complete library preparation for next generation high throughput sequencing (e.g., to add sample index (SI) sequences (e.g., i7) and/or further adapter sequences (e.g., P7)). The fully constructed library is then sequenced according to a suitable next-generation sequencing protocol (e.g., Illumina sequencing).

Example 13. Generation of Barcoded Nucleic Acid Fragments Using Bulk Tagmentation and CRISPR/Cas9 Cleavage in Droplets Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei are then incubated in the presence of a transposase-nucleic acid complex as described in Example 9. See FIG. 29A. In some embodiments, after transposition, the transposase is inactivated or dissociated from the adapter-flanked template nucleic acid fragments.

Figure 32A:
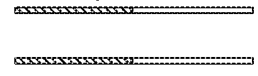
FIGS. 32A-C illustrate an exemplary barcoding scheme.
Figure 32B:
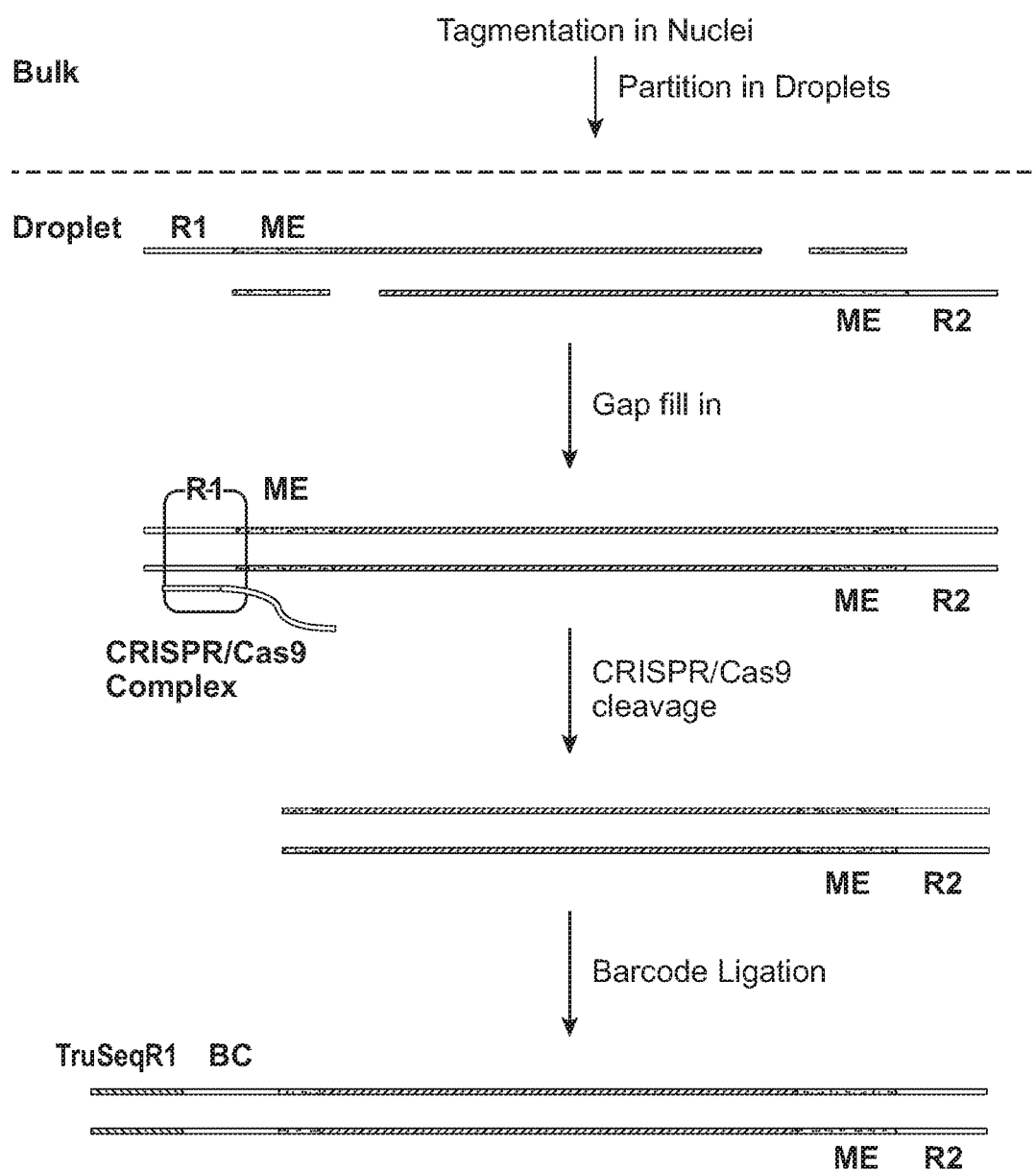

Nuclei (or cells) comprising the adapter-flanked template nucleic acid fragments are then partitioned into a plurality of droplets such that at least some droplets comprise (1) a single nucleus comprising the adapter-flanked template nucleic acid fragments; (2) a plurality of double-stranded barcode oligonucleotide molecules comprising a barcode sequence (BC) and a TruSeqR1 sequencing primer sequence (e.g., FIG. 32A); and (3) a plurality of CRISPR/Cas9 complexes comprising a Cas9 nuclease and a synthetic guide RNA (gRNA) that targets the Read1/ME adapter sequence in the adapter-flanked template nucleic acid fragments. See FIG. 32B. In some embodiments, the double-stranded barcode oligonucleotide molecules are attached to a gel bead and partitioned such that at least some droplets comprise (1) a single nucleus; (2) a single gel bead; and (3) a plurality of CRISPR/Cas9 complexes. In addition to the aforementioned components, in some embodiments, the plurality of droplets further comprises reagents (e.g., enzymes and buffers) that facilitate the reactions described below.

Single nucleus containing droplets are then subjected to conditions to release the adapter-flanked template nucleic acid fragments from the nuclei. After the adapter-flanked template nucleic acid fragments are released, gaps from the transposition reaction are filled with a suitable gap-filling enzyme. Gap-filled adapter-flanked template nucleic acid fragments are then subjected to Cas9-mediated cleavage of the R1/ME adaptor, or some portion thereof. See FIG. 32B. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The barcode oligonucleotides are then ligated onto the R1 adapter-cleaved ends of the template nucleic acid fragments to produce barcoded, adapter-flanked template nucleic acid fragments. See FIG. 32B.

The barcoded, adapter-flanked template nucleic acid fragments are then released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a second CRISPR/Cas9 mediated cleavage event using a synthetic guide RNA (gRNA) that targets the Read2/ME adapter sequence is performed either in the partition or in bulk after release from the partition. The fully constructed library is then sequenced according to any suitable sequencing protocol.

Figure 32C:
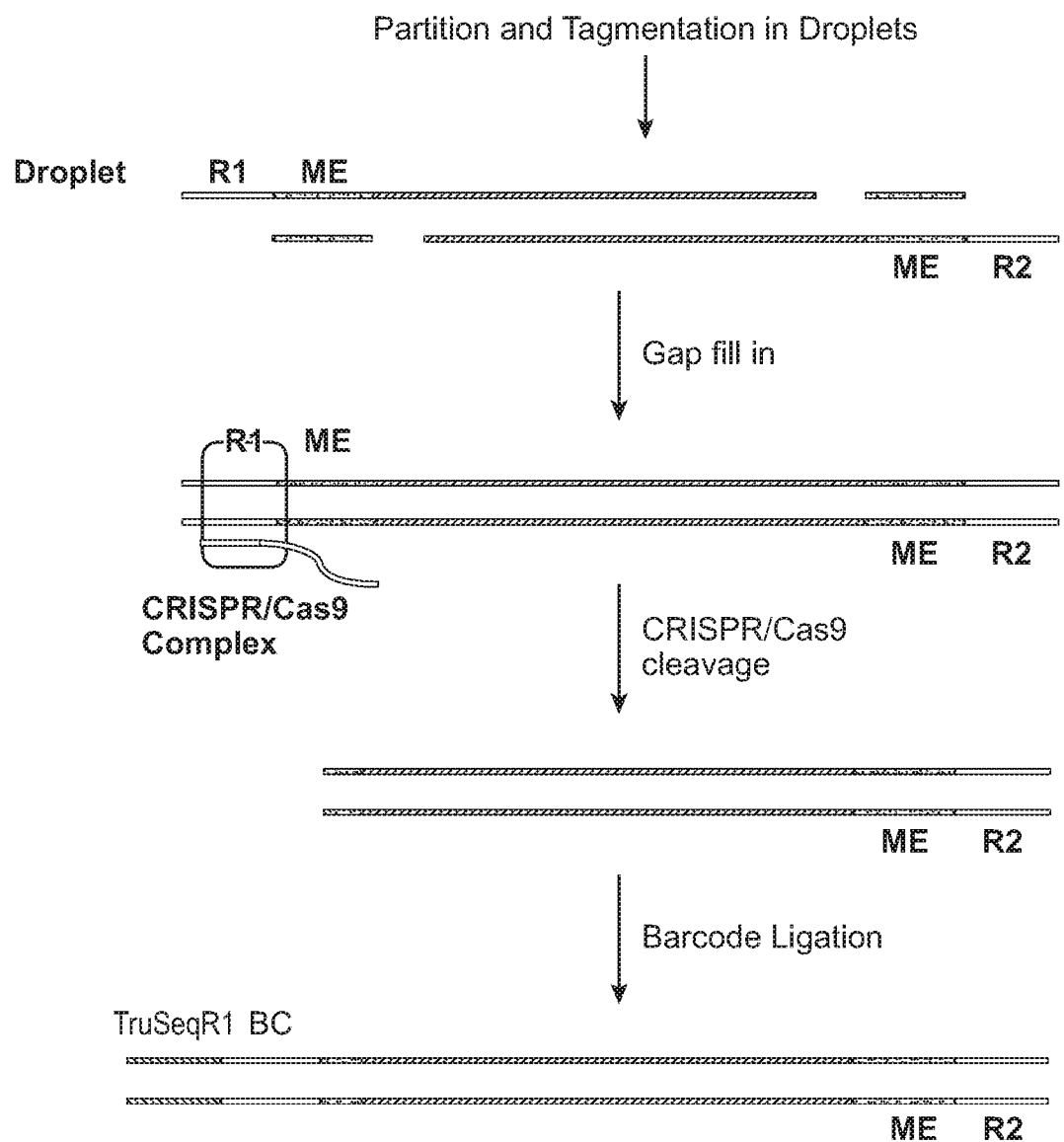

Example 14. Generation of Barcoded Nucleic Acid Fragments Using Tagmentation and CRISPR/Cas9 Cleavage in Droplets Cells from a cell population of interest (or intact nuclei from cells in a cell population of interest) are partitioned into a plurality of droplets such that at least some droplets comprise (1) a single cell (or a single nucleus) comprising a template nucleic acid; (2) a plurality of double-stranded barcode oligonucleotide molecules comprising a barcode sequence (BC) and a TruSeqR1 sequencing primer sequence (e.g., FIG. 32A); and (3) a plurality of CRISPR/Cas9 complexes comprising a Cas9 nuclease and a synthetic guide RNA (gRNA) that targets the Read1/ME adapter sequence in the adapter-flanked template nucleic acid fragments. See, e.g., FIG. 32C. In some embodiments, the double-stranded barcode oligonucleotide molecules are attached to a gel bead and partitioned such that at least some droplets comprise (1) a single cell (or single nucleus); (2) a single gel bead; and (3) a plurality of CRISPR/Cas9 complexes. In addition to the aforementioned components, in some embodiments, the plurality of droplets further comprises reagents (e.g., enzymes and buffers) that facilitate the reactions described below.

After partitioning into droplets, the single cells (or nuclei) are lysed to release the template genomic DNA in a manner that substantially maintains native chromatin organization. Droplets are then subjected to conditions to generate a transposase-nucleic acid complex as described in Example 9 and shown in FIG. 29A. Alternatively, in some embodiments, a plurality of pre-formed transposase-nucleic acid complexes as shown in FIG. 29A are partitioned into the plurality of droplets. Droplets are then subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Samples are then processed generally as described in Example 13. After tagmentation, gaps from the transposition reaction are filled with a suitable gap-filling enzyme. See FIG. 32C. Gap-filled adapter-flanked template nucleic acid fragments are then subjected to Cas9-mediated cleavage of the R1 adaptor. See FIG. 32C. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The barcode oligonucleotides are then ligated onto the R1 adapter-cleaved ends of the template nucleic acid fragments to produce barcoded, adapter-flanked template nucleic acid fragments. See FIG. 32C.

The barcoded, adapter-flanked template nucleic acid fragments are then released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a second CRISPR/Cas9 mediated cleavage event using a synthetic guide RNA (gRNA) that targets the Read2/ME adapter sequence is performed either in the partition or in bulk after release from the partition. The fully constructed library is then sequenced according to any suitable sequencing protocol.

Example 15. Generation of Barcoded Nucleic Acid Fragments Using Bulk Tagmentation and CRISPR/Cas9 Cleavage in Droplets Using Y-Adapters Nuclei are harvested in bulk from cells in a cell population of interest in a manner that substantially maintains native chromatin organization. Alternatively, cells are permeabilized, allowing the transposase-nucleic acid complex to gain access to the nucleus. Nuclei are then incubated in the presence of a transposase-nucleic acid complex as described in Example 9. See FIG. 29A. In some embodiments, after transposition, the transposase is inactivated or dissociated from the adapter-flanked template nucleic acid fragments.

Figure 33A:
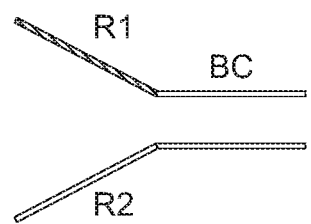
FIGS. 33A-C illustrate an exemplary barcoding scheme.
Figure 33B:
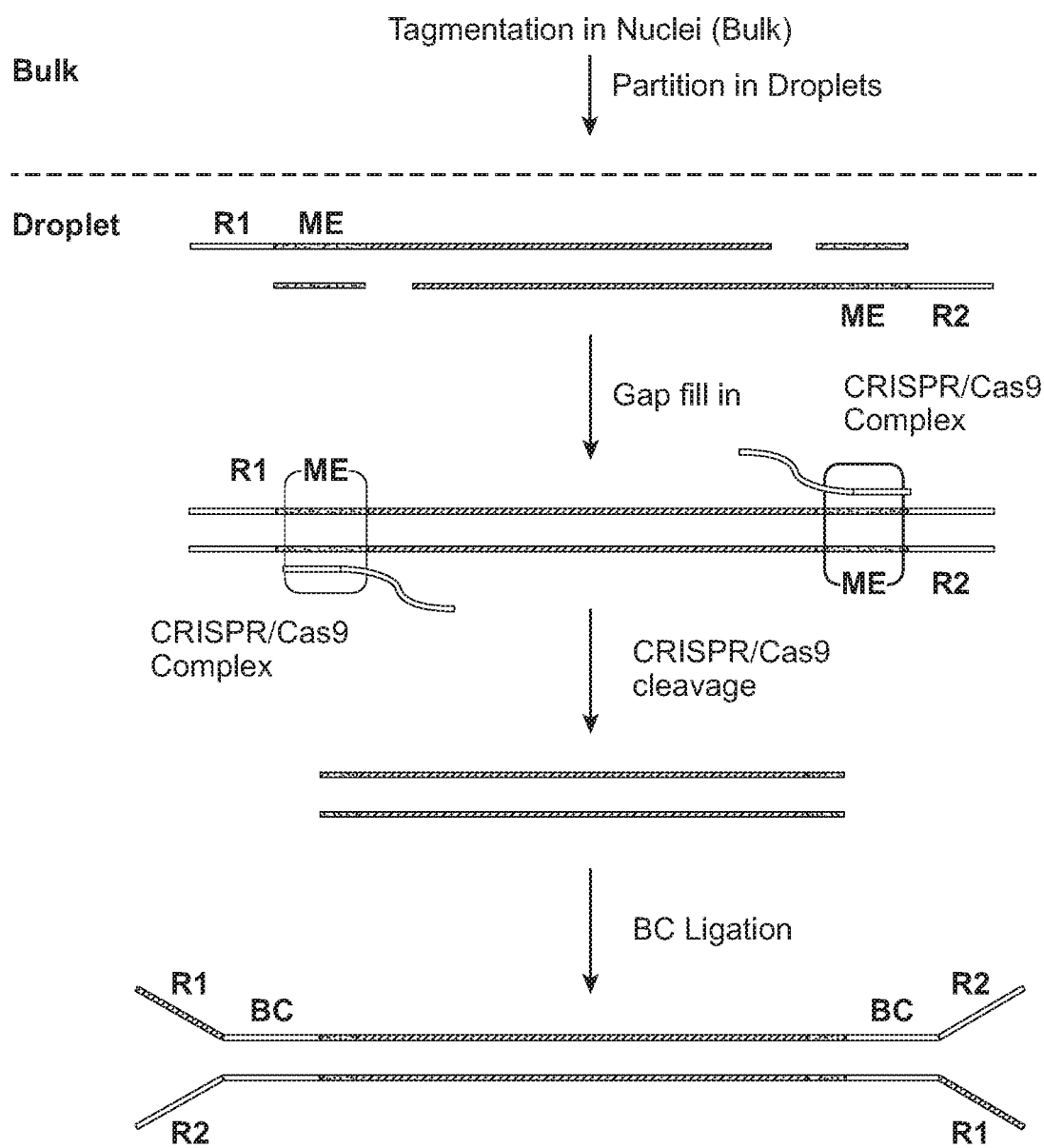
Figure 33C:
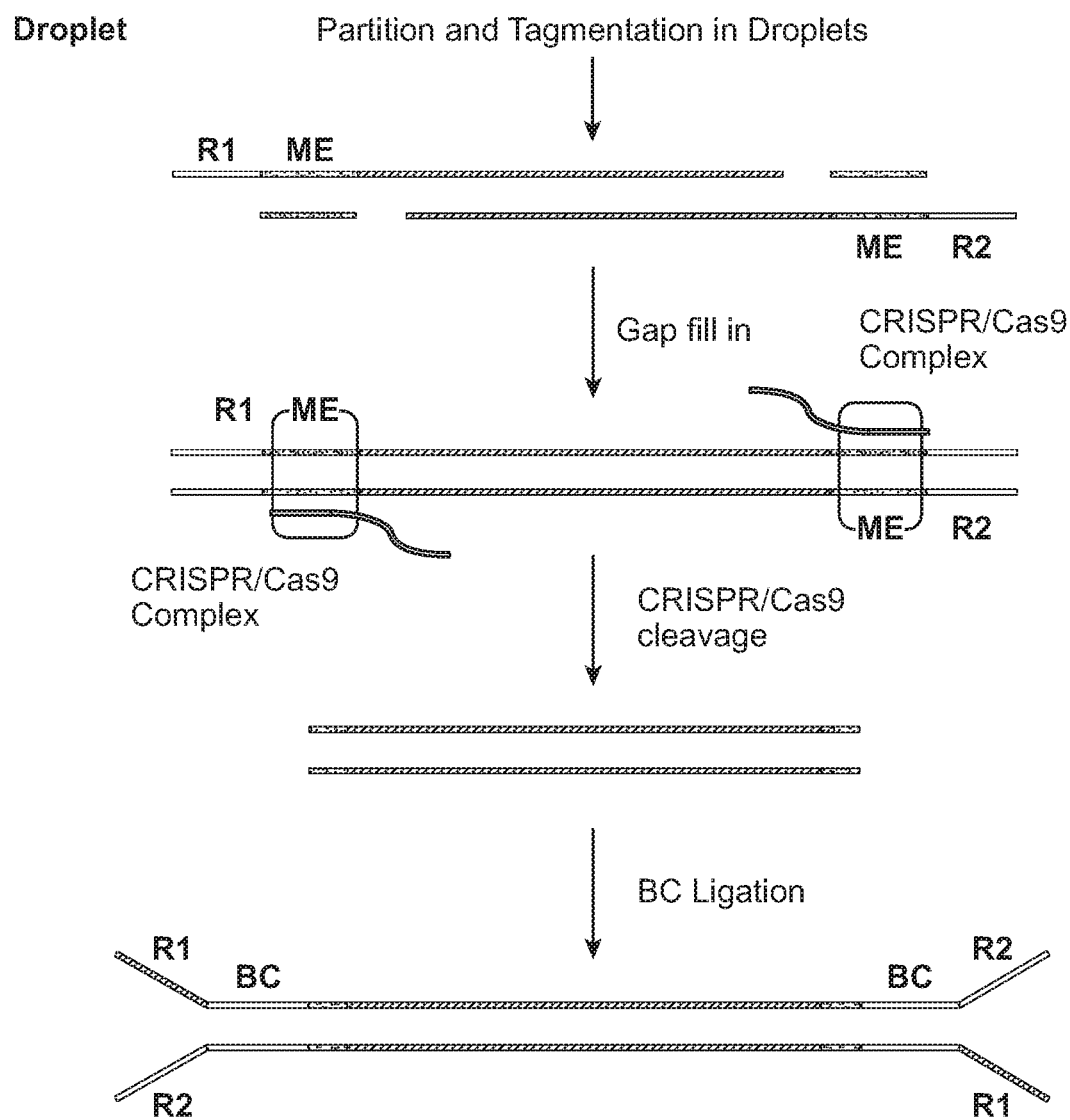

Nuclei (or cell) comprising the adapter-flanked template nucleic acid fragments are then partitioned into a plurality of droplets such that at least some droplets comprise (1) a single nucleus comprising the adapter-flanked template nucleic acid fragments; (2) a plurality of Y-adaptor barcode oligonucleotide molecules comprising a barcode sequence (BC), a Read1 sequencing primer sequence (R1), and a Read2 sequencing primer sequence (R2), e,g., FIG. 33A; (3) a first plurality of CRISPR/Cas9 complexes comprising a Cas9 nuclease and a synthetic guide RNA (gRNA) that targets the Read1/ME adapter sequence in the adapter-flanked template nucleic acid fragments; and (4) a second plurality of CRISPR/Cas9 complexes comprising a Cas9 nuclease and a synthetic guide RNA (gRNA) that targets the Read2/ME adapter sequence in the adapter-flanked template nucleic acid fragments. See FIG. 33. In some embodiments, the Y-adaptor barcode oligonucleotide molecules are attached to a gel bead (e.g., FIG. 15A) and partitioned such that at least some droplets comprise (1) a single nucleus; (2) a single gel bead; (3) the first plurality of CRISPR/Cas9 complexes; and (4) the second plurality of CRISPR/Cas9 complexes. In addition to the aforementioned components, in some embodiments, the plurality of droplets further comprises reagents (e.g., enzymes and buffers) that facilitate the reactions described below.

Single nucleus containing droplets are then subjected to conditions to release the adapter-flanked template nucleic acid fragments from the nuclei. After the adapter-flanked template nucleic acid fragments are released, gaps from the transposition reaction are filled with a suitable gap-filling enzyme. Gap-filled adapter-flanked template nucleic acid fragments are then subjected to Cas9-mediated cleavage of the R1 and R2 adaptors, or a portion thereof. See FIG. 33B. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The Y-adaptor barcode oligonucleotides are then ligated onto the R1/R2 adapter-cleaved ends of the template nucleic acid fragments to produce barcoded, adapter-flanked template nucleic acid fragments. See FIG. 33B.

The barcoded, adapter-flanked template nucleic acid fragments are then released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). The fully constructed library is then sequenced according to any suitable sequencing protocol.

Example 16. Generation of Barcoded Nucleic Acid Fragments Using Tagmentation and CRISPR/Cas9 Cleavage in Droplets Using Y-Adapters Cells from a cell population of interest (or intact nuclei from cells in a cell population of interest) are partitioned into a plurality of droplets such that at least some droplets comprise (1) a single cell (or a single nucleus) comprising a template nucleic acid; (2) a plurality of Y-adaptor barcode oligonucleotide molecules comprising a barcode sequence (BC), a Read1 sequencing primer sequence (R1), and a Read2 sequencing primer sequence (R2) (e.g., FIG. 33A); (3) a first plurality of CRISPR/Cas9 complexes comprising a Cas9 nuclease and a synthetic guide RNA (gRNA) that targets the Read1/ME adapter sequence in the adapter-flanked template nucleic acid fragments; and (4) a second plurality of CRISPR/Cas9 complexes comprising a Cas9 nuclease and a synthetic guide RNA (gRNA) that targets the Read2/ME adapter sequence in the adapter-flanked template nucleic acid fragments. See FIG. 33C. In some embodiments, the Y-adaptor barcode oligonucleotide molecules are attached to a gel bead and partitioned such that at least some droplets comprise (1) a single cell (or single nucleus); (2) a single gel bead; (3) the first plurality of CRISPR/Cas9 complexes; and (4) the second plurality of CRISPR/Cas9 complexes. In addition to the aforementioned components, in some embodiments, the plurality of droplets further comprises reagents (e.g., enzymes and buffers) that facilitate the reactions described below.

After partitioning into droplets, the single cells (or nuclei) are lysed to release the template genomic DNA in a manner that substantially maintains native chromatin organization. Droplets are then subjected to conditions to generate a transposase-nucleic acid complex as described in Example 9 and shown in FIG. 29A. Alternatively, in some embodiments, a plurality of pre-formed transposase-nucleic acid complexes as shown in FIG. 29A are partitioned into the plurality of droplets. Droplets are then subjected to conditions such that the transposase-nucleic acid complexes integrate the first and second adapter sequences into the template nucleic acid to generate double-stranded adapter-flanked template nucleic acid fragments. Because the transposase-nucleic acid complex can only act on nucleosome-free DNA, the adapter-flanked template nucleic acid fragments are representative of genome-wide areas of accessible chromatin in a single cell. Alternatively, in some embodiments, the tagmentation reaction is performed in intact nuclei, and the nuclei are lysed to release the double-stranded adapter-flanked template nucleic acid fragments.

Samples are then processed generally as described in Example 15. After tagmentation, gaps from the transposition reaction are filled with a suitable gap-filling enzyme. See FIG. 33C. Gap-filled adapter-flanked template nucleic acid fragments are then subjected to Cas9-mediated cleavage of the R1 and R2 adaptors, or a portion thereof. See FIG. 33C. In certain embodiments, where barcode oligonucleotides are attached to a gel bead, droplets are subjected to conditions to cause release of the barcode oligonucleotide molecules from the gel bead (e.g., depolymerization of gel beads, for example, using a reducing agent such as DTT). The Y-adaptor barcode oligonucleotides are then ligated onto the R1/R2 adapter-cleaved ends of the template nucleic acid fragments to produce barcoded, adapter-flanked template nucleic acid fragments. See FIG. 33C.

The barcoded, adapter-flanked template nucleic acid fragments are then released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). The fully constructed library is then sequenced according to any suitable sequencing protocol.

Example 17. Generation of Barcoded Nucleic Acid Molecules for ATAC-Seq and Barcoded cDNA from the Same Single Cell Cells from a cell population of interest (or intact nuclei from cells in a cell population of interest) are partitioned into a plurality of droplets such that at least some droplets comprise (1) a single cell (or a single nucleus) comprising template genomic DNA molecules and template RNA molecules; (2) a plurality of first barcoded oligonucleotide molecules comprising a barcode sequence; (3) a plurality of transposase molecules, (4) a plurality of second barcode oligonucleotide molecules comprising a barcode sequence and a capture sequence; and (5) a plurality of reverse transcriptase molecules. In some embodiments, the barcode sequence from the first barcoded oligonucleotide and the barcode sequence from the second barcoded oligonucleotide is the same. In some embodiments, the barcode sequence from the first barcoded oligonucleotide and the barcode sequence from the second barcoded oligonucleotide are different.

In some embodiments, the plurality of first barcoded oligonucleotides and the plurality of second barcoded oligonucleotides are attached to a gel bead and partitioned such that at least some droplets comprise (1) a single cell (or single nucleus); (2) a single gel bead comprising the first and second plurality of barcoded oligonucleotides; (3) a plurality of transposase molecules; and (4) a plurality of reverse transcriptase molecules. In other embodiments, the plurality of first barcoded oligonucleotides are attached to a first gel bead while the plurality of second barcoded oligonucleotides are attached to a second gel bead and partitioned such that at least some droplets comprise (1) a single cell (or single nucleus); (2) a single first gel bead; (2) a single second gel bead; (3) a plurality of transposase molecules; and (4) a plurality of reverse transcriptase molecules.

Figure 34:
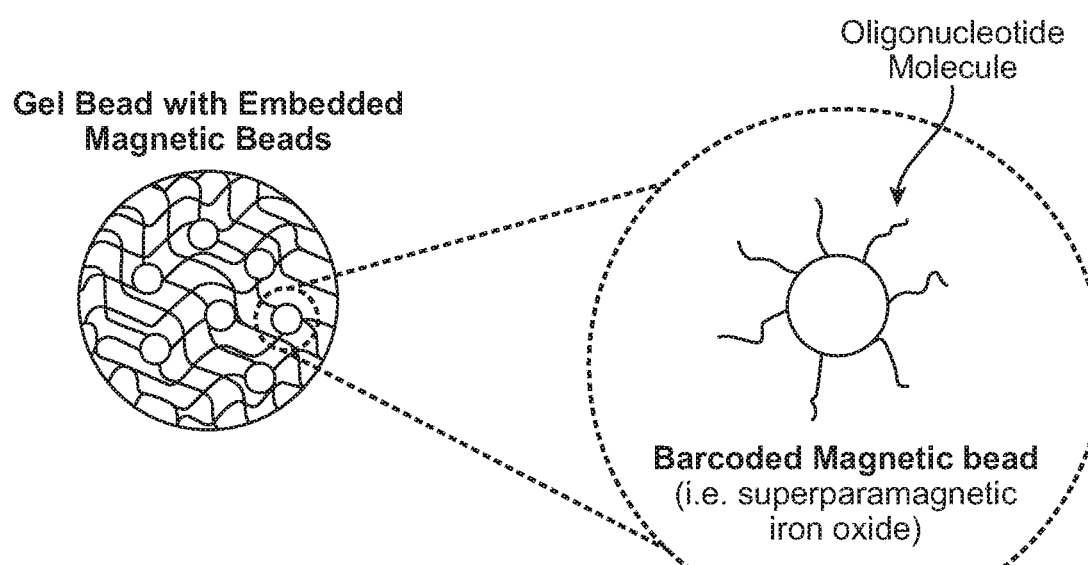
FIG. 34 illustrates barcoded magnetic beads which can be embedded within a gel bead comprising a barcoded oligonucleotide.

In certain embodiments, the plurality of first barcoded oligonucleotides are attached to a gel bead while the plurality of second barcoded oligonucleotides are attached to a plurality of magnetic beads, wherein the plurality of magnetic beads are embedded within the gel bead. Continuing these embodiments, the gel bead is partitioned such that at least some droplets comprise: (1) a single cell (or single nucleus); (2) a single gel bead comprising (i) a plurality of first barcoded oligonucleotides attached to the single gel bead; and (ii) a plurality of magnetic particles embedded within the single gel bead, wherein the magnetic particles comprise the second barcode oligonucleotide attached thereto; (3) a plurality of transposase molecules; and (4) a plurality of reverse transcriptase molecules. See, e.g., FIG. 34. Similarly, in other embodiments, the second barcode oligonucleotides are attached to the gel bead while the first oligonucleotides are attached to a plurality of magnetic particles embedded within the gel bead. See, e.g., FIG. 34. In addition to the aforementioned components, in some embodiments, the plurality of droplets further comprise reagents (e.g., enzymes and buffers) that facilitate the reactions described herein.

The first barcoded oligonucleotide and related nucleic acid processing steps can take on the structure of any of the aforementioned Examples and may include additional components as described therein. For instance, in some embodiments, the first barcoded oligonucleotide comprises a barcode sequence and a transposon end sequence (e.g., a ME sequence) and is, for example, (1) a forked adapter such as those described in Example 1, FIGS. 12A-B; (2) a T7-containing oligonucleotide such as those described in Example 3, FIG. 18; or (3) a barcoded oligonucleotide such as those described in (i) Example 7, FIG. 28B; (ii) Example 11, FIGS. 30A-B; and (iii) Example 12, FIG. 31. In other embodiments, the first barcoded oligonucleotide comprises a barcode sequence and is, for example, (1) a forked adapter such as those described in Example 2, FIGS. 15A-B or Examples 15-16, FIGS. 33A-C; or (2) a barcoded oligonucleotide such as those described in Examples 9 and 10, FIGS. 29A-C or Examples 13-14, FIGS. 32A-C. The capture sequence on the second barcoded oligonucleotide can be, for example, an oligo(dT) sequence, a random primer sequence (e.g., a random hexamer), or a gene-specific sequence.

After partitioning into droplets, the single cells (or nuclei) are lysed to release template genomic DNA and template RNA (e.g., cytoplasmic mRNA or nuclear mRNA) in a manner that substantially maintains native chromatin organization of the genomic DNA. In certain embodiments, where barcode oligonucleotides are attached to a gel bead, droplets are subjected to conditions to cause release of barcode oligonucleotide molecules from the gel bead (e.g., depolymerization of gel beads, for example, using a reducing agent such as DTT). Droplets are then subjected to conditions to generate a transposase-nucleic acid complex as described in the aforementioned examples. Alternatively, in some embodiments, a plurality of pre-formed transposase-nucleic acid complexes are partitioned into the plurality of droplets. Droplets are then subjected to conditions such that the transposase-nucleic acid complexes generate double-stranded template genomic DNA fragments. As described above, the transposition reaction can take on the structure of any of the aforementioned Examples to generate double-stranded template genomic DNA fragments flanked by a wide variety of functional sequences and suitable for a number of downstream processing steps. For example, as described herein, in some embodiments, the transposition reaction directly integrates the barcode sequence into the template genomic DNA fragments (e.g., Example 1) while, in other embodiments, the barcode sequence is added to template genomic DNA fragments subsequent to the transposition reaction (such as by ligation, e.g., Example 2). Because the transposase-nucleic acid complex can only act on nucleosome-free DNA, the template genomic DNA fragments are representative of genome-wide areas of accessible chromatin in a single cell. Alternatively, in some embodiments, the transposition reaction is performed in intact nuclei, and the nuclei are lysed to release the adapter-flanked template genomic DNA fragments. Alternatively, in some embodiments, the transposition reaction is performed in bulk in intact nuclei and a single nucleus comprising template genomic DNA fragments is partitioned and processed as described above. In some embodiments, gaps from the transposition reaction are filled in-droplet with a suitable gap-filling enzyme. In other embodiments, a gap-filling reaction is performed in bulk after the double-stranded, barcoded adapter-flanked DNA fragments have been released from the partition.

Droplets are then subjected to conditions to generate single-stranded, barcoded cDNA molecules from the template RNA using the capture sequence from the second barcode oligonucleotide to prime the reverse transcription reaction (e.g., an oligo (dT) sequence). In some embodiments, second strand cDNA is produced (e.g., through a template switching oligonucleotide or through random priming) to generate double-stranded, barcoded cDNA molecules. In some embodiments, the template switching oligonucleotide also comprises a barcode sequence such that both the 5' and 3' end of the cDNA comprise a barcode sequence. The barcode sequence on the 5' and 3' end can be the same barcode sequence or the 5' end can have a different barcode sequence than the 3' end. In other embodiments, the plurality of second barcode oligonucleotide molecules are omitted and replaced with plurality of second oligonucleotide molecules comprising a capture sequence and no barcode sequence. Continuing with these embodiments, first strand cDNA molecules are generated using the capture sequence while second strand cDNA is generated through use of a barcoded template switching oligonucleotide to barcode the 5' end of the template RNA. In some embodiments, an in-droplet amplification reaction, such as linear amplification, is performed on the adapter-flanked DNA fragments, the barcoded cDNA molecules, or both the adapter-flanked DNA fragments and the barcoded cDNA molecules. In some embodiments, a barcode oligonucleotide is directly ligated onto the template RNA.

The barcoded, adapter-flanked DNA fragments and the barcoded cDNA molecules are then released from the droplets and processed in bulk to complete library preparation for next generation high throughput sequencing (e.g., subjecting the fragments, or derivatives thereof, to one or more reactions (e.g., nucleic acid amplification) to add functional sequences to facilitate Illumina sequencing). In some embodiments, a first portion of the released emulsion comprising the adapter-flanked DNA fragments and the barcoded cDNA is taken and processed in bulk to complete library preparation for the barcoded, adapter-flanked DNA fragments while a second portion of the released emulsion is taken and processed in bulk to complete library preparation for the barcoded cDNA molecules. In other embodiments, a first portion of the droplets comprising the barcoded, adapter-flanked DNA fragments and the barcoded cDNA molecules is taken and processed in bulk to complete library preparation for the barcoded, adapter-flanked DNA fragments while a second portion of the droplets comprising the barcoded, adapter-flanked DNA fragments and the barcoded cDNA molecules is taken and processed in bulk to complete library preparation for the barcoded cDNA molecules. In embodiments that utilize a magnetic bead, the barcoded template molecules attached thereto can be magnetically separated and further processed to complete library preparation. The fully constructed library or libraries are then sequenced according to a suitable next-generation sequencing protocol (e.g., Illumina sequencing).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A partition comprising:
   (i) a cell or cell nucleus comprising:
      a) a plurality of adapter-flanked template deoxyribonucleic acid (DNA) fragments; and
      b) a template ribonucleic acid (RNA) molecule;
   (ii) one or more first barcode oligonucleotide molecules comprising a first barcode sequence and a sequence complementary to an adapter sequence of the plurality of adapter-flanked template deoxyribonucleic acid (DNA) fragments;
   (iii) one or more second barcode oligonucleotide molecules comprising a second barcode sequence and a functional sequence; and
   (iv) a plurality of reverse transcriptase molecules.

2. The partition of claim 1, wherein the cell or cell nucleus is a permeabilized cell or cell nucleus.

3. The partition of claim 1, wherein said first barcode sequence is different from said second barcode sequence.

4. The partition of claim 1, wherein said first barcode oligonucleotide molecule and said second barcode oligonucleotide molecule comprise a common barcode sequence.

5. The partition of claim 1, wherein: (i) the one or more first barcode oligonucleotide molecules; (ii) the one or more second barcode oligonucleotide molecules; or (iii) the one or more first barcode oligonucleotide molecules and the one or more second barcode oligonucleotide molecules are attached to a solid or semi-solid support.

6. The partition of claim 5, wherein each barcoded oligonucleotide molecule is releasable from the solid or semi-solid support upon application of a stimulus.

7. The partition of claim 6, wherein the stimulus is a chemical or enzymatic stimulus and wherein the partition comprises the stimulus.

8. The partition of claim 5, wherein the solid or semi-solid support comprises a bead.

9. The partition of claim 8, wherein the bead is a gel bead.

10. The partition of claim 9, wherein the gel bead is degradable upon application of a stimulus.

11. The partition of claim 10, wherein the stimulus is a chemical or enzymatic stimulus and wherein the partition comprises the stimulus.

12. The partition of claim 1, which is a well.

13. The partition of claim 1, which is an aqueous droplet in an emulsion.

14. The partition of claim 1, wherein the functional sequence is complementary to a sequence of the template RNA molecule.

15. The partition of claim 1, wherein the functional sequence is a poly-T sequence.

16. The partition of claim 1, wherein the functional sequence comprises a template switching oligonucleotide sequence that facilitates a template switching reaction from a cDNA generated from the template RNA molecule.

17. A partition comprising:
  (i) a cell nucleus comprising a plurality of tagged nucleic acid fragments, wherein the plurality of tagged fragments comprises, from 5' to 3', a first adapter sequence, a sequence of genomic deoxyribonucleic acid (DNA) from the cell nucleus, and a second adapter sequence;
  (ii) a plurality of template ribonucleic acid (RNA) molecules from the cell nucleus;
  (iii) a bead comprising, attached thereto:
    (a) one or more first barcode oligonucleotide molecules comprising a first barcode sequence and a sequence complementary to the first or the second adapter; and
    (b) one or more second barcode oligonucleotide molecules comprising a second barcode sequence and a functional sequence;
  and
  (iv) a plurality of reverse transcriptase molecules.

18. The partition of claim 17, wherein each barcoded oligonucleotide molecule comprises a labile bond capable of releasing the barcoded oligonucleotide molecule from the bead upon application of a stimulus.

19. The partition of claim 18, wherein the stimulus is a chemical or enzymatic stimulus and wherein the partition comprises the stimulus.

20. The partition of claim 17, wherein the bead is a gel bead.

21. The partition of claim 20, wherein the gel bead is degradable upon application of a stimulus.

22. The partition of claim 21, wherein the stimulus is a chemical or enzymatic stimulus and wherein the partition comprises the stimulus.

23. The partition of claim 17, which is a well.

24. The partition of claim 17, which is an aqueous droplet in an emulsion.

25. The partition of claim 17, wherein the functional sequence is complementary to a sequence of the template RNA molecule.

26. The partition of claim 17, wherein the functional sequence is a poly-T sequence.

27. The partition of claim 17, wherein the functional sequence comprises a template switching oligonucleotide sequence that facilitates a template switching reaction from a cDNA generated from the template RNA molecule.

28. The partition of claim 19, wherein the labile bond is a disulfide bond and the stimulus is a reducing agent.

29. The partition of claim 17, wherein said first barcode sequence is different from said second barcode sequence.

30. The partition of claim 17, wherein said first barcode oligonucleotide molecule and said second barcode oligonucleotide molecule comprise a common barcode sequence.

* * * * *